US011833229B2

(12) United States Patent
Rösch et al.

(10) Patent No.: US 11,833,229 B2
(45) Date of Patent: Dec. 5, 2023

(54) LABELING PRECURSORS WITH SQUARIC ACID COUPLING

(71) Applicant: SCV—SpezialChemikalienVertrieb GmbH, Berlin (DE)

(72) Inventors: Frank Rösch, Zornheim (DE); Lukas Greifenstein, Mainz (DE); Nils Engelbogen, Kiel (DE); Ralf Bergmann, Dresden (DE)

(73) Assignee: SCV Spezial-Chemikalien-Vertriebs GmbH, Berlin (DE)

( * ) Notice: Subject to any disclaimer, the term of this patent is extended or adjusted under 35 U.S.C. 154(b) by 0 days.

(21) Appl. No.: 17/745,100

(22) Filed: May 16, 2022

(65) Prior Publication Data

US 2022/0331456 A1  Oct. 20, 2022

Related U.S. Application Data

(63) Continuation of application No. 17/287,692, filed as application No. PCT/EP2019/078614 on Oct. 21, 2019.

(51) Int. Cl.
*A61K 51/04* (2006.01)
*A61K 47/54* (2017.01)

(52) U.S. Cl.
CPC .......... *A61K 51/0497* (2013.01); *A61K 47/54* (2017.08); *A61K 51/0478* (2013.01); *A61K 51/0482* (2013.01)

(58) Field of Classification Search
CPC ................ A61K 51/0497; A61K 47/54; A61K 51/0478; A61K 51/0482
USPC ....................................................... 424/1.65
See application file for complete search history.

(56) References Cited

U.S. PATENT DOCUMENTS

| 10,441,607 B1 * | 10/2019 | Azhdarinia | ........ A61K 49/0021 |
| 2011/0092806 A1 | 4/2011 | Port et al. | |
| 2017/0327520 A1 * | 11/2017 | Rösch | .................. A61K 31/675 |
| 2021/0038749 A1 * | 2/2021 | Haberkorn | ........... A61K 49/106 |

FOREIGN PATENT DOCUMENTS

| WO | 2013107820 A1 | 7/2013 |
| WO | 2015055318 A1 | 4/2015 |
| WO | 2016058056 A1 | 4/2016 |
| WO | 2016058704 A1 | 4/2016 |

OTHER PUBLICATIONS

Banerjee et al. Oncotarget 2011, 2, 1344-1253. (Year: 2011).*
Wurm et al. Chem. Soc. Rev. 2013, 42, 8220-8236. (Year: 2013).*
Donovan et al., "Method for measuring the logarithm of the octanol-water partition coefficient by using short octadecyl-poly(vinyl alcohol) high-performance liquid chromatography columns" Journal of Chromatography A, 2002, vol. 952, pp. 47-61.
Jansen et al., "Extended Structure-Activity Relationship and Pharmacokinetic Investigation of (4-Quinolinoyl)glycyl-2-cyanopyrrolidine Inhibitors of Fibroblast Activation Protein (FAP)" Journal of Medicinal Chemistry, 2014, vol. 7, pp. 3053-3074.
International Search Report, PCT/EP2019/078614.

* cited by examiner

*Primary Examiner* — Michael G. Hartley
*Assistant Examiner* — Sean R Donohue
(74) *Attorney, Agent, or Firm* — ProPat, LLC; Cathy Moore

(57) ABSTRACT

The invention relates to a marking precursor incorporating a chelator or fluorination group for radiolabelling with $^{44}$Sc, $^{47}$Sc, $^{55}$Co, $^{62}$Cu, $^{64}$Cu, $^{67}$Cu, $^{66}$Ga, $^{67}$Ga, $^{68}$Ga, $^{89}$Zr, $^{86}$Y, $^{90}$Y, $^{90}$Nb, $^{99m}$Tc, $^{111}$In, $^{135}$Sm, $^{140}$Pr, $^{159}$Gd, $^{149}$Tb, $^{160}$Tb, $^{161}$Tb, $^{165}$Er, $^{166}$Dy, $^{166}$Ho, $^{175}$Yb, $^{177}$Lu, $^{186}$Re, $^{188}$Re, $^{213}$Bi and $^{225}$Ac or with $^{18}$F, $^{131}$I or $^{211}$At, and one or two biological targeting vectors which are coupled to the chelator or fluorinating group via one or more squaric acid groups.

15 Claims, 60 Drawing Sheets

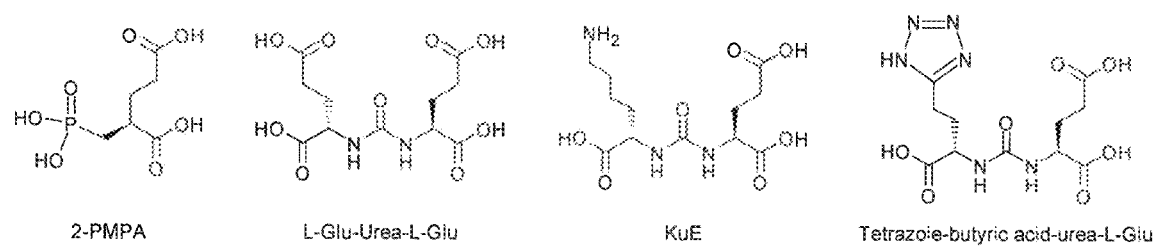
Fig. 1: PSMA inhibitors

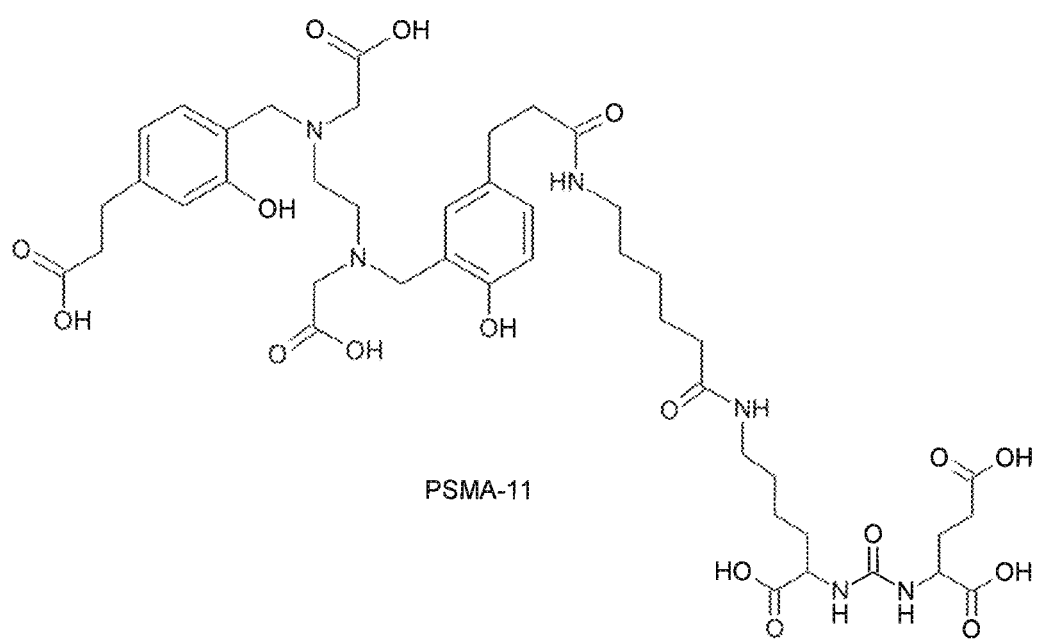
Fig. 2: Labeling precursor PSMA-11

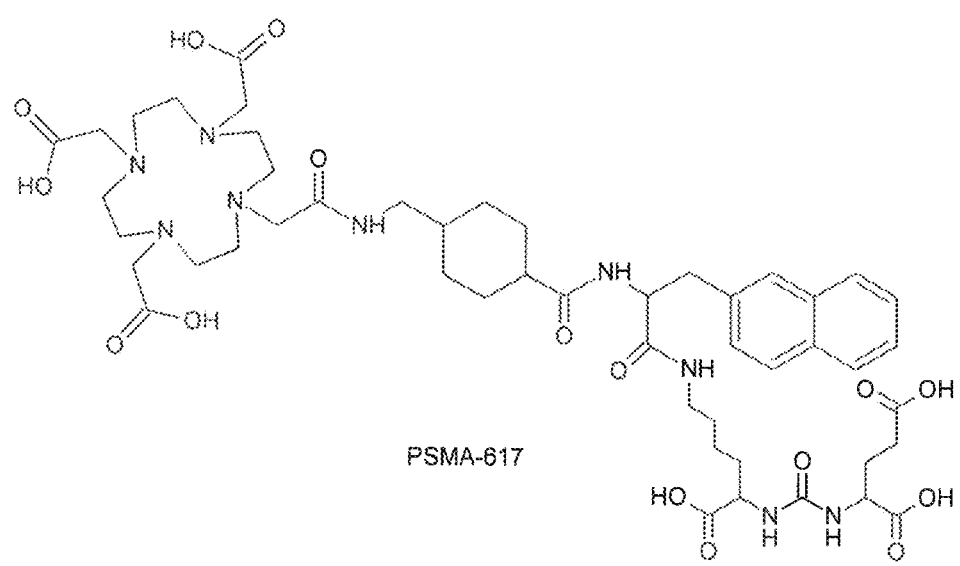
Fig. 3: Labeling precursor PSMA-617

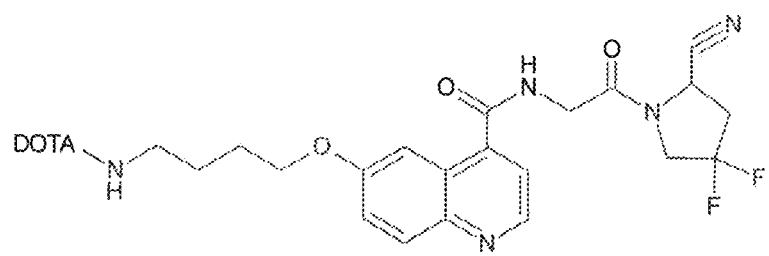
Fig. 4: DOTA-conjugated FAP-labeling precursor

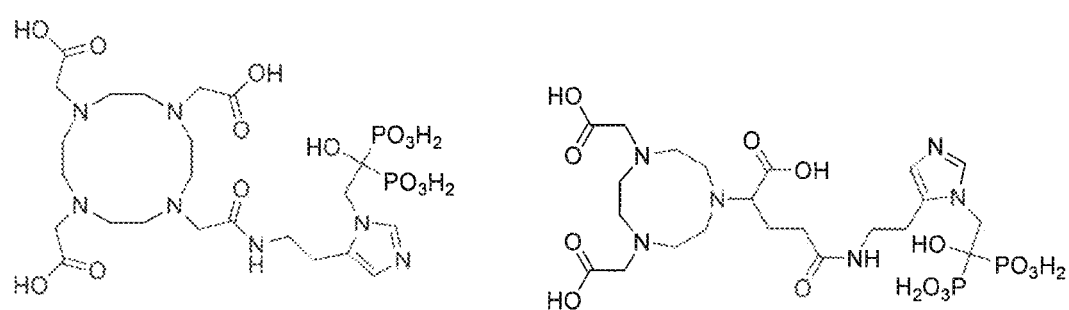
Fig. 5: Tracer DOTA-Zoledronate (left) and NODAGA-Zoledronate (right)

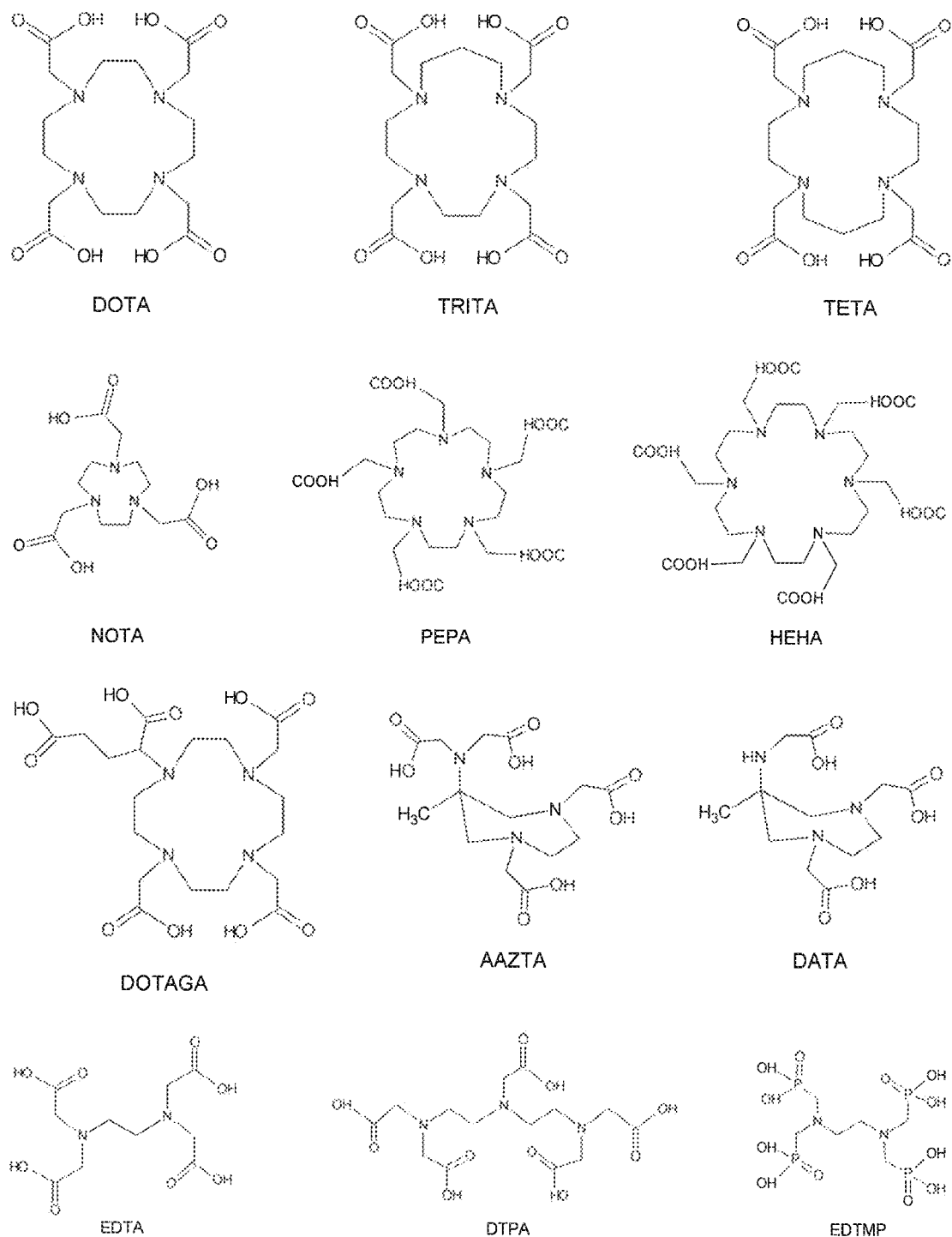
Fig. 6A: Chelators used in the invention

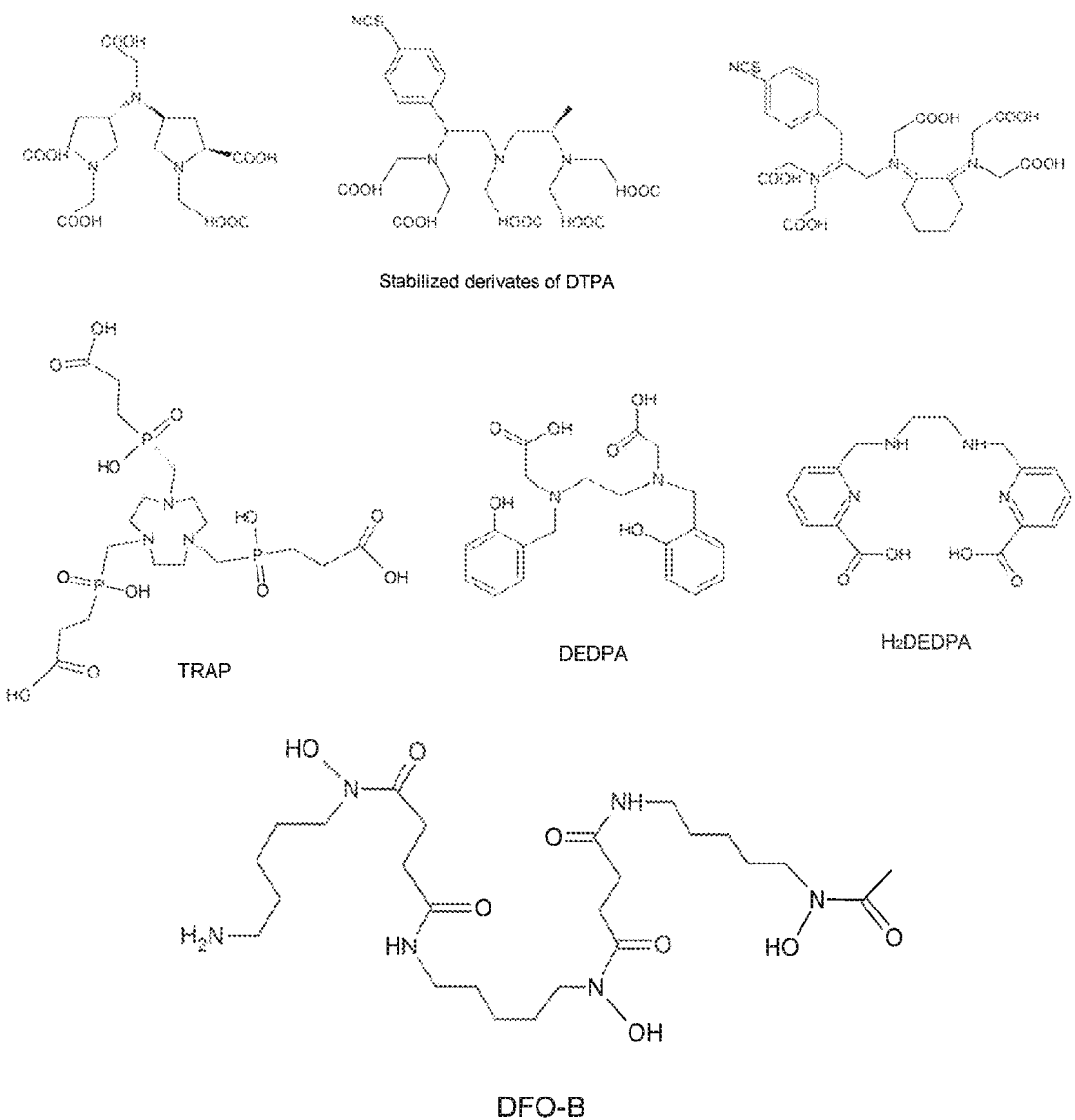
Fig. 6B: Chelators used in the invention

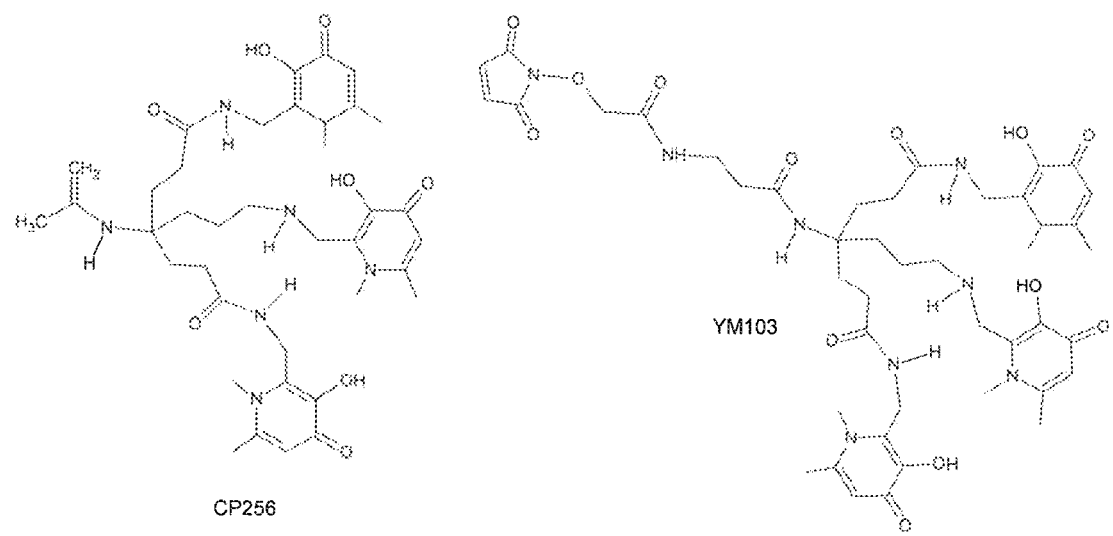
Fig. 6C: Chelators used in the invention

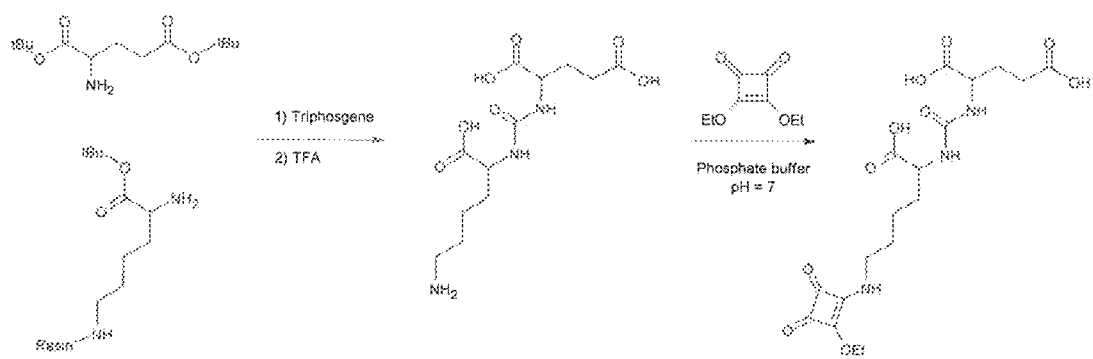
Fig. 7: Synthesis schema for QS-KuE precursor

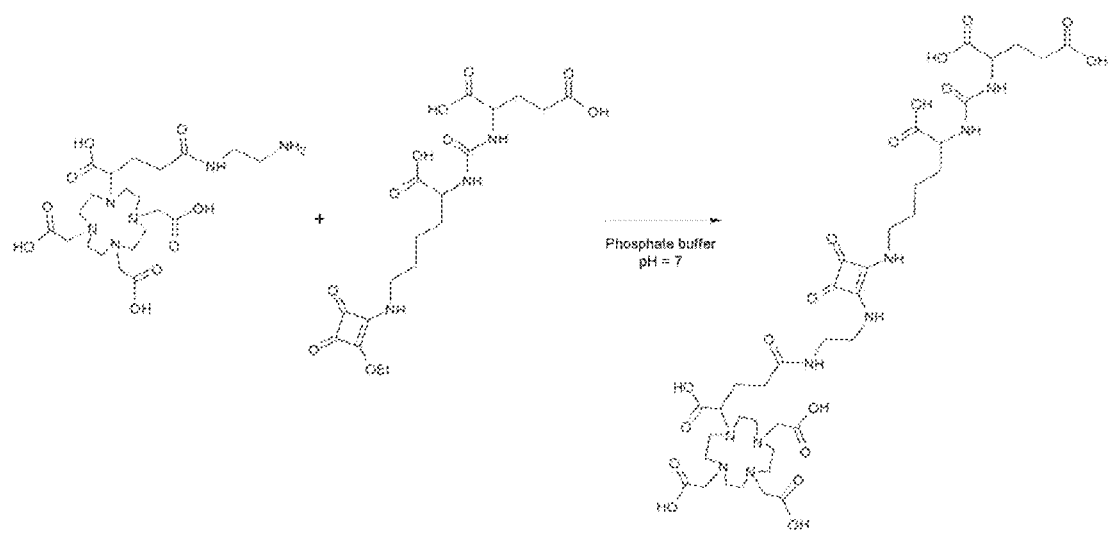
Fig. 8: Coupling of QS-KuE precursor to DOTA

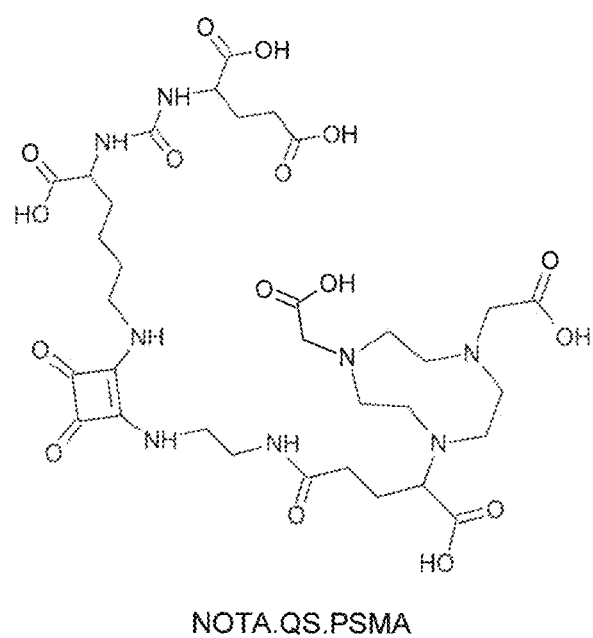
NOTA.QS.PSMA
Fig. 9A: Labeling precursors NOTA.QS.PSMA, AAZTA.QS.PSMA and DATA.QS.PSMA

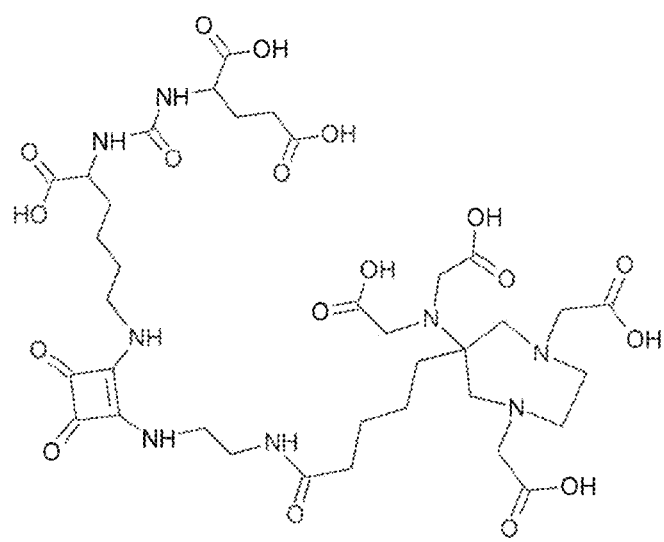
AAZTA.QS.PSMA
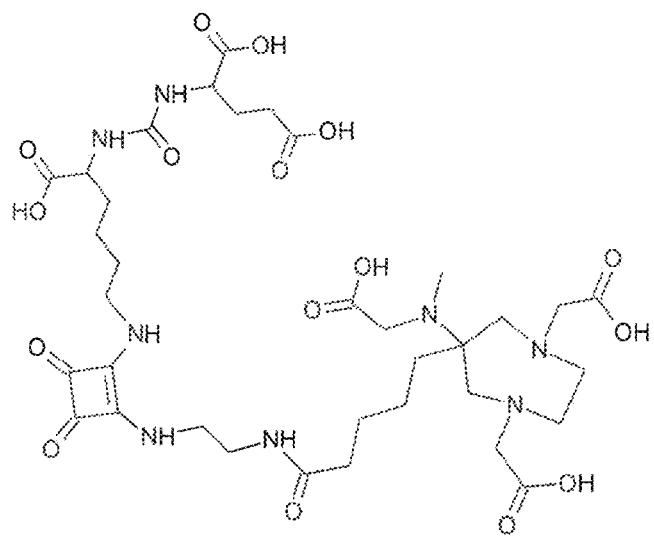
DATA.QS.PSMA
Fig. 9B: Labeling precursors NOTA.QS.PSMA, AAZTA.QS.PSMA and DATA.QS.PSMA

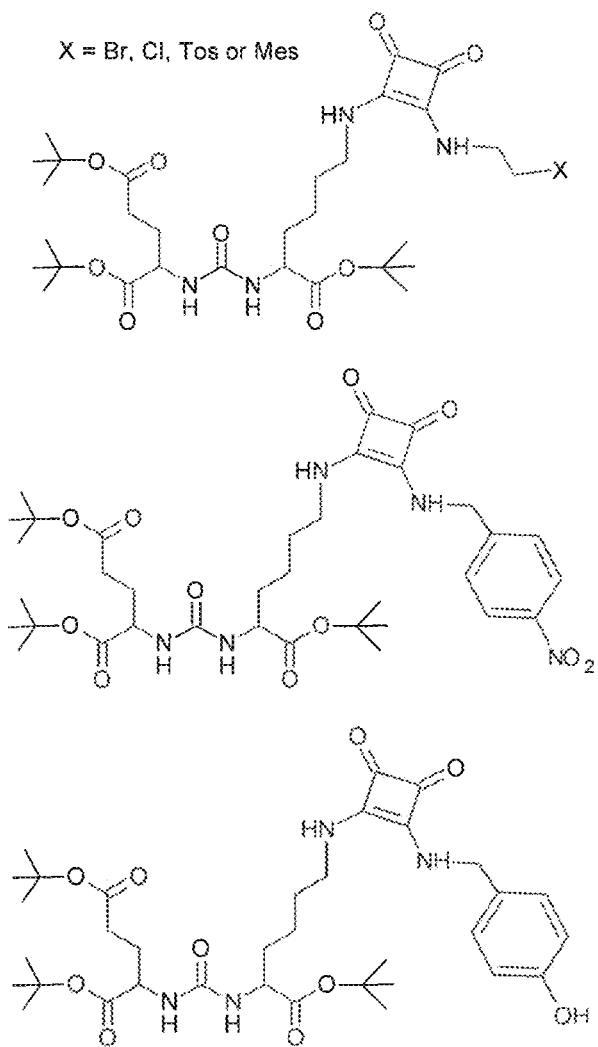
Fig. 10: Squaric acid-conjugated PSMA-labeling precursor for radiohalides

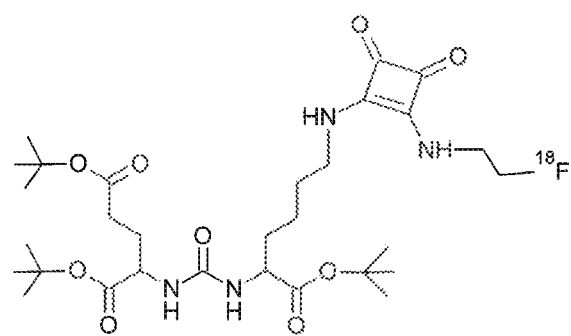
Fig. 11: Squaric acid-conjugated $^{18}$F-radiotracer for PSMA before cleavage of tert-butyl protecting groups

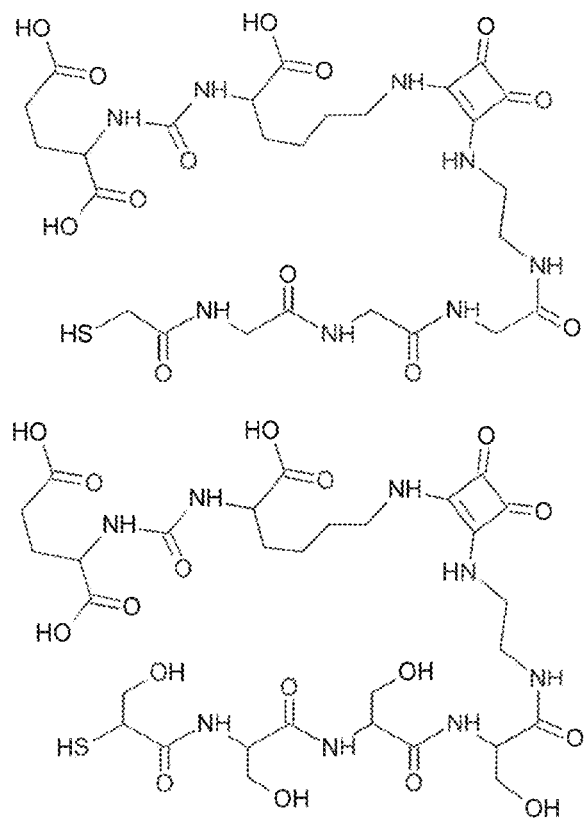
Fig. 12: Squaric acid-conjugated PSMA-labeling precursor for $^{99m}$Tc with aminothiol based chelator of type "N3S"

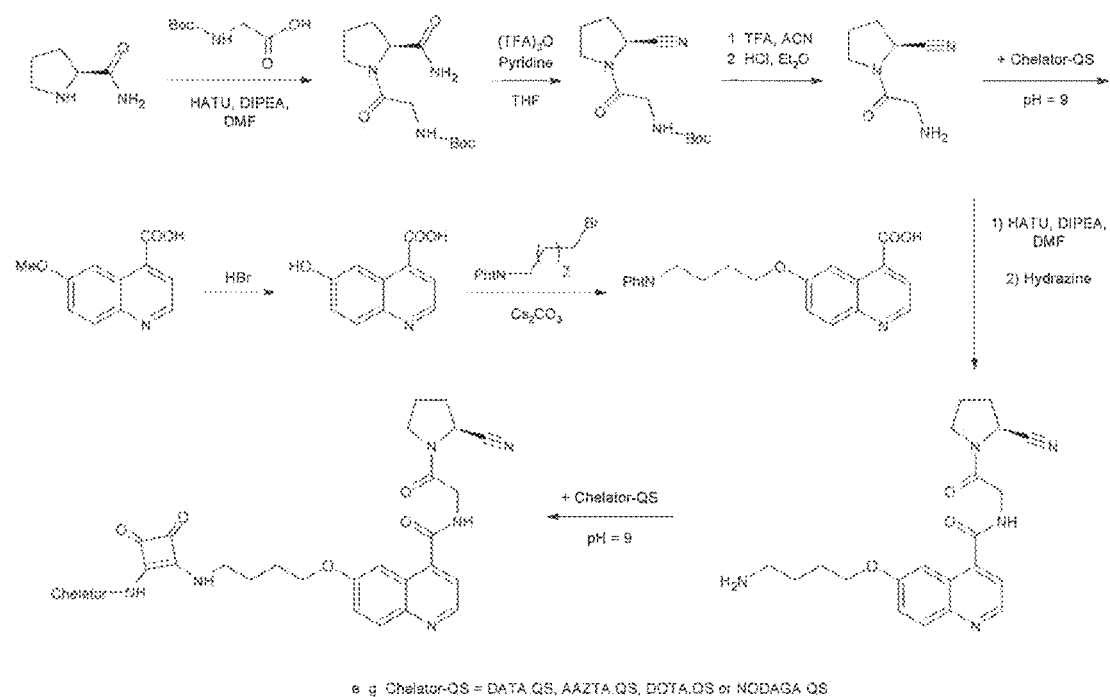
Fig. 13: Synthesis strategy for FAP-labeling precursor

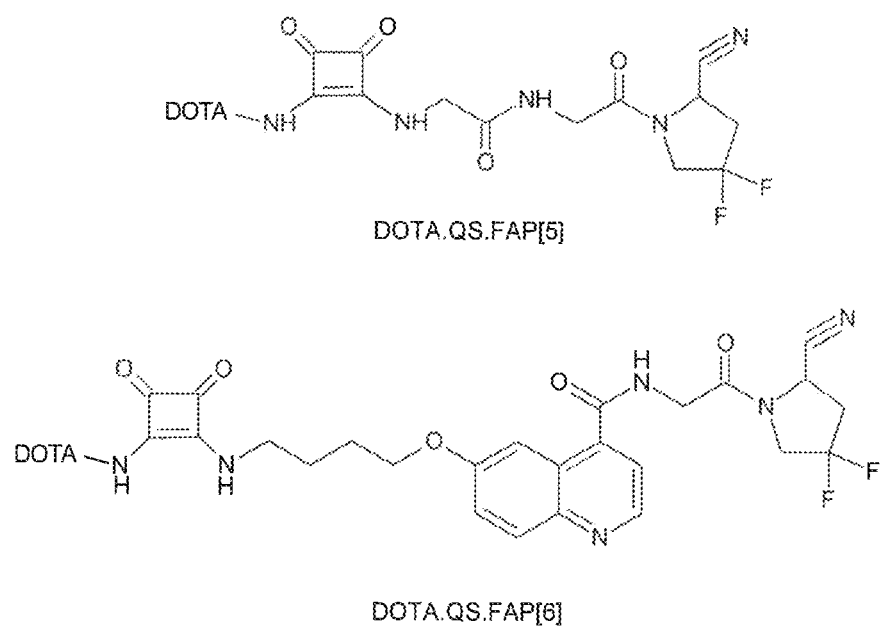
Fig. 14: FAP-labeling precursor with squaric acid-coupling

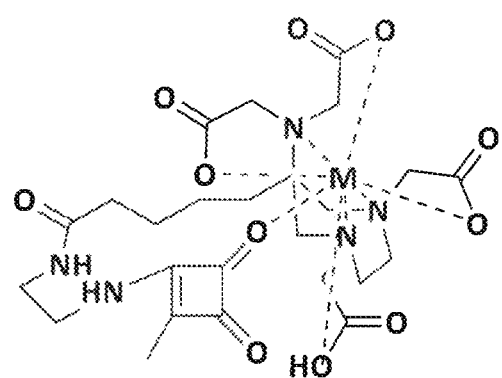
Fig. 15: Coordination by AAZTA.QS

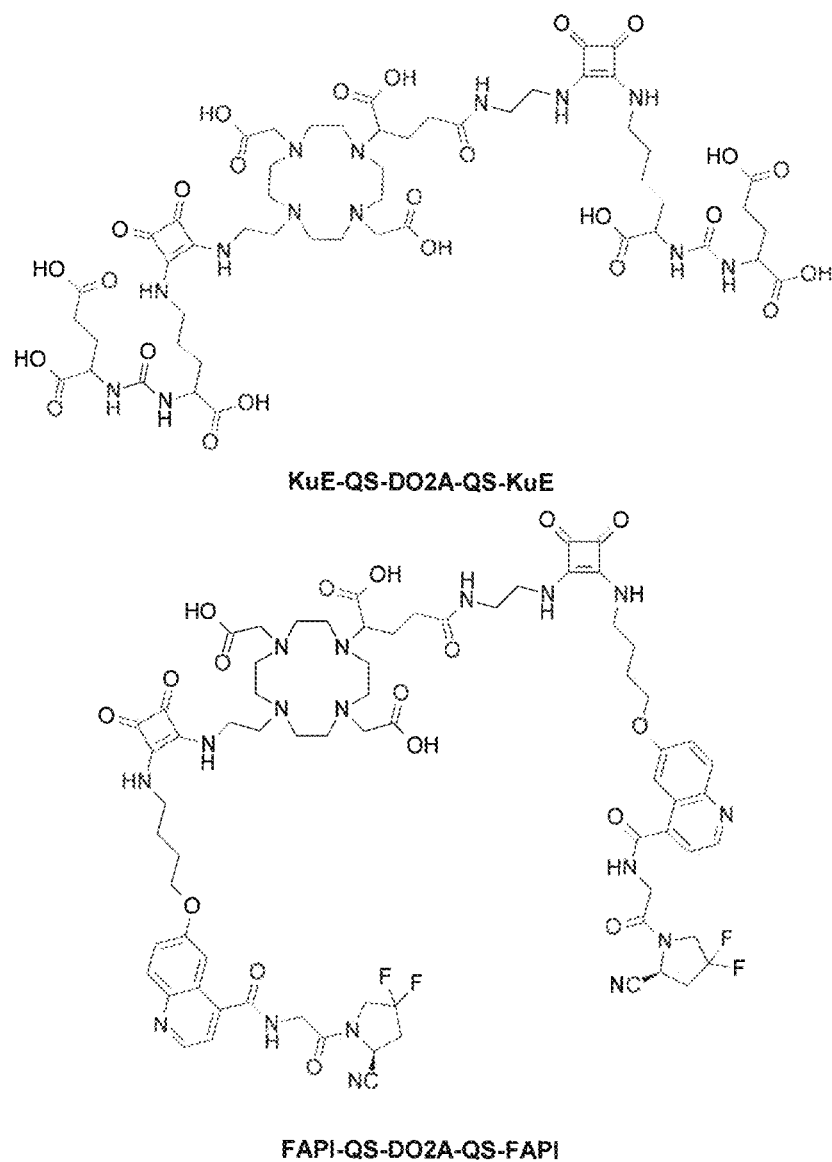
Fig. 16: Dimeric labeling precursor

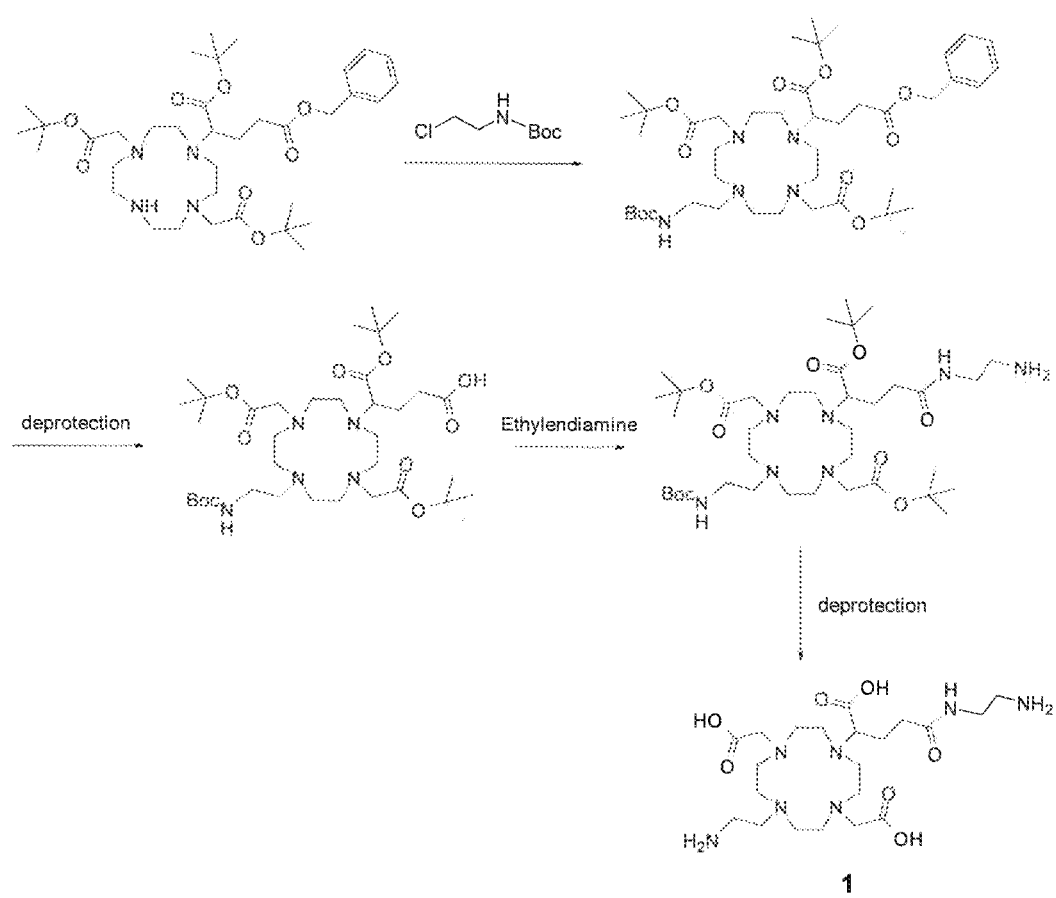
Fig. 17: Synthesis of DOA2 with two amine groups

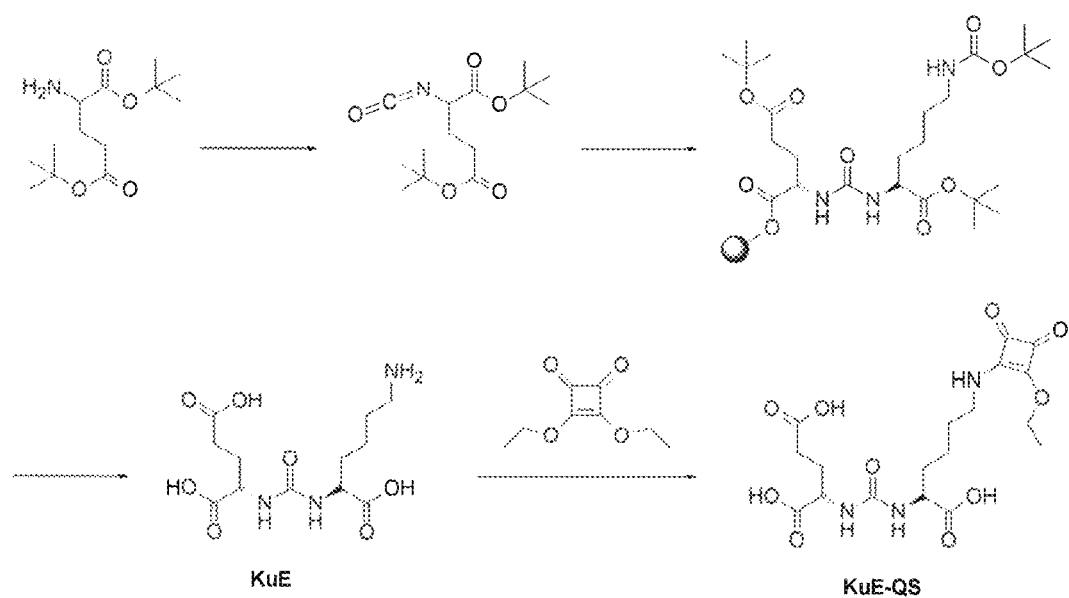
Fig. 18: Synthesis of KuE-QS

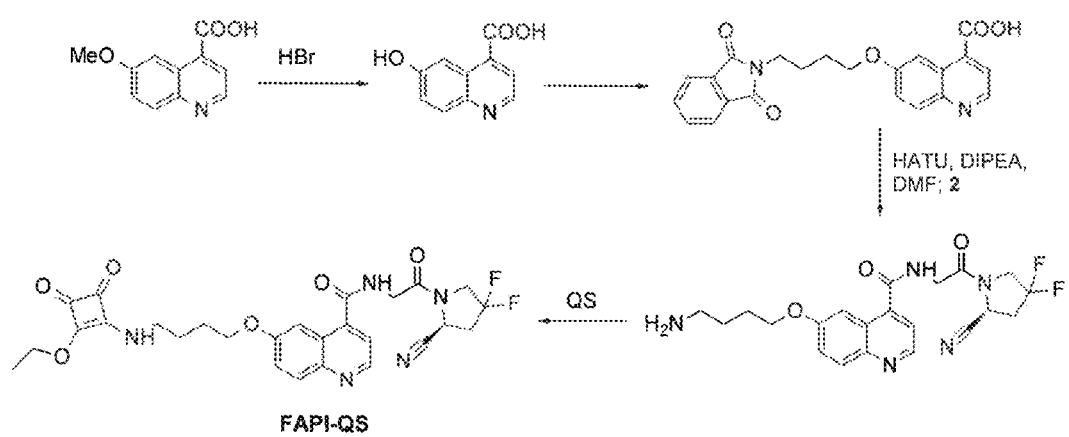
Fig. 19: Synthesis of FAPI-QS

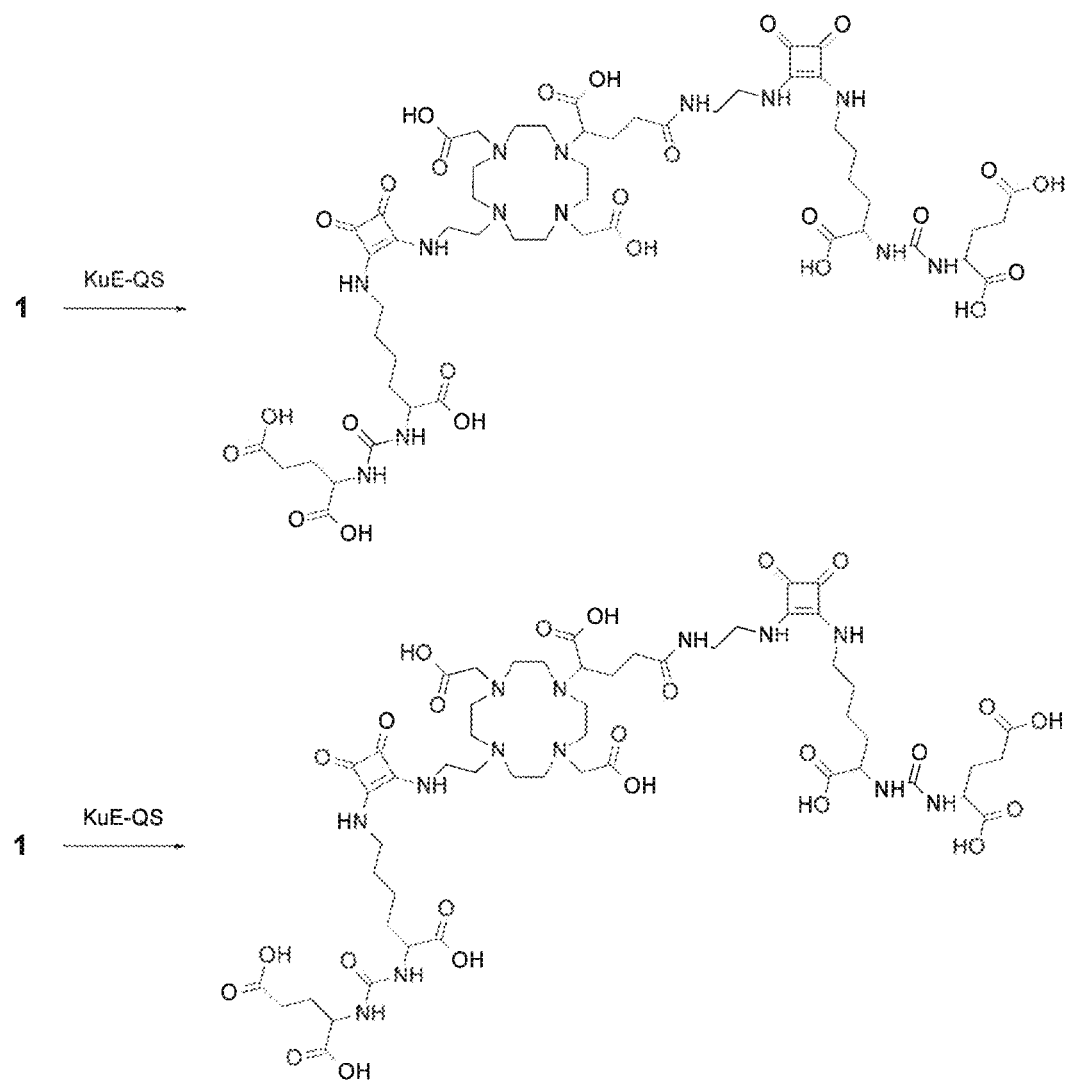
Fig. 20: Synthesis of dimers

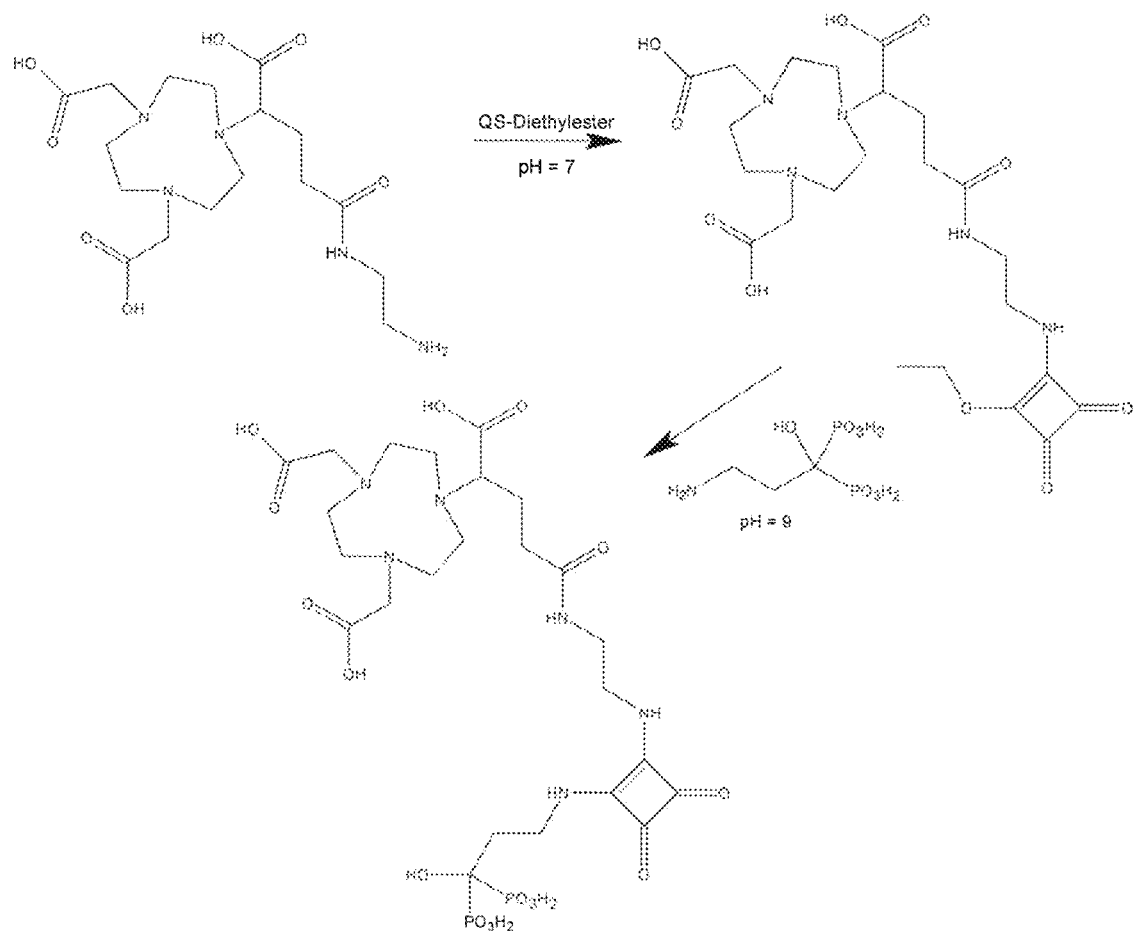
Fig. 24: Synthesis of NODAGA.QS.PAM

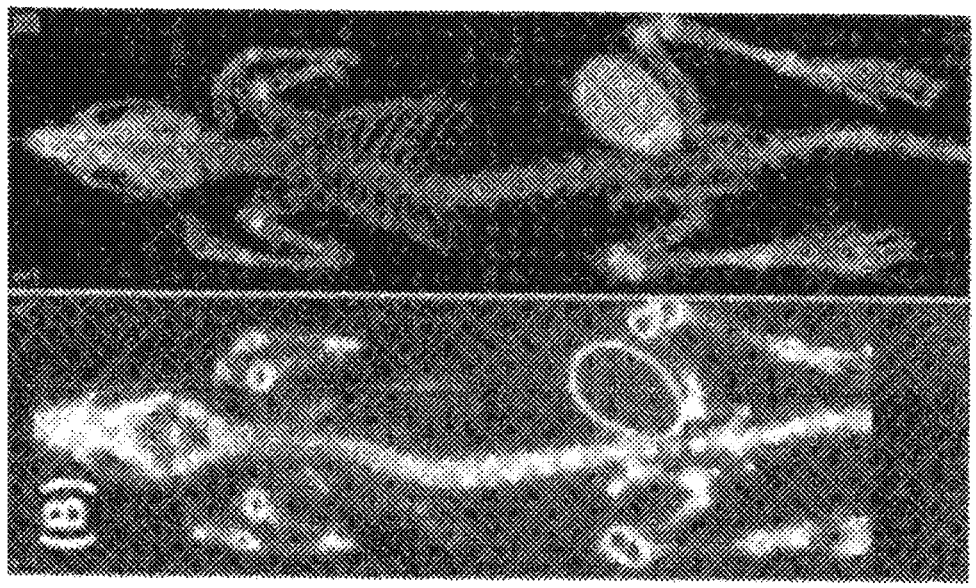
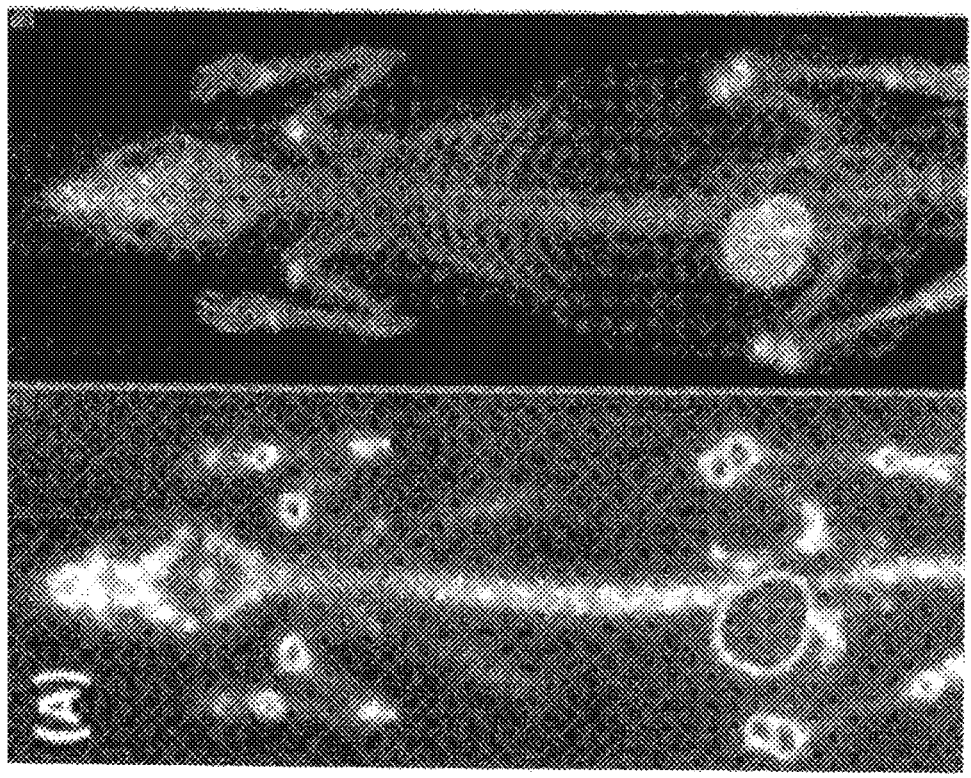
Fig. 25A
Fig. 25B a) DIPEA, Triphosgene, DCM, 0 °C, 4h;
b) H-Lys(tBoc)-2CT-Polystyrol-solid phase, DCM, RT, 16 h;
c) TFA, RT, 71 %,
d) Dimethyl Squarate, Phosphate buffer (pH=7), RT, 24h 85%
e) Phosphate buffer pH = 9, RT, 24h, 20%.

Fig. 50: Compounds for $^{18}$F-radiotracers

Fig. 51: Synthesis DATA.QS.FAPi

LABELING PRECURSORS WITH SQUARIC ACID COUPLING

CROSS-REFERENCE TO RELATED APPLICATIONS

This application claims priority to pending U.S. patent application Ser. No. 17/287,692 filed Apr. 22, 2021, which claims priority to International Application No. PCT/EP2019/078614 filed Oct. 21, 2019, which claims priority to parent application German Patent Application No. 10 2018 126 558.1, filed Oct. 24, 2018. Each of the foregoing applications, i.e. U.S. patent application Ser. No. 17/287,692, International Application No. PCT/EP2019/078614 and German Patent Application No. 10 2018 126 558.1, are hereby incorporated by reference herein in their entirety.

FIELD OF THE INVENTION

The present invention relates to labeling precursors comprising a chelator or a fluorination group and one or two targeting vectors, each coupled to the chelator or the fluorination group via linkers and optionally spacers.

The labeling precursors according to the invention are intended for nuclear-medical imaging radiological diagnosis and treatment (theranostics) of cancers in which tumor cells express prostate-specific membrane antigen (PSMA), fibroblast activation protein (FAP) or farnesyl pyrophosphate synthase (FPPS).

BACKGROUND OF THE INVENTION

For about 15 years, radiological imaging diagnostic methods such as positron emission tomography (PET) and single photon emission computed tomography (SPECT) is used. Recently, theranostic procedures have also become increasingly important.

In radiological diagnostics and theranostics, tumor cells are labeled or irradiated with a radioactive isotope such as $^{68}$Ga or $^{177}$Lu. In doing so labeling precursors are used which bind the respective radioisotope covalently ($^{18}$F) or coordinatively ($^{68}$Ga, $^{99m}$Tc, $^{177}$Lu). In the case of metallic radioisotopes, the labeling precursors comprise a chelator for the effective and stable complexation of the radioisotope as an essential chemical component and a biological targeting vector as a functional component which binds to target structures in the tumor tissue. As a rule, the biological targeting vector has a high affinity for cell membrane receptors, proteins or enzymes of tumor cells.

After intravenous injection into the bloodstream, the labeling precursor labeled with a radioisotope accumulates on or in tumor cells. In order to minimize the radiation dose in healthy tissue during diagnostic examinations, a small amount of a radioisotope with a short half-life of a few hours to days is used. The configuration and chemical properties of the targeting vector are modified by the chelator or the fluorination group and, as a rule, its affinity to tumor cells strongly influenced. Accordingly, the coupling between the chelator or the fluorination group and the at least one targeting vector is tailored in elaborate trial-and-error experiments or so-called biochemical screenings. A large number of labeling precursors comprising the chelator or a fluorination group and the at least one targeting vector are synthesized and in particular the affinity for tumor cells is quantified. The chelator or the fluorination group and the chemical coupling with the targeting vector are decisive for the biological and radiological potency of the respective labeling precursor.

In addition to a high affinity, the labeling precursor must meet other requirements, such as fast and effective complexation or covalent binding of the respective radioisotope;

high selectivity for tumor cells relative to healthy tissue;

in vivo stability, i. e. biochemical resistance in blood serum under physiological conditions.

Prostate Cancer

For men in developed countries, prostate cancer is the most common cancer and the third most common fatal cancer. Tumor growth is slow in this disease, and if diagnosed at an early stage, the 5-year survival rate is close to 100%. If the disease is only discovered after the tumor has metastasized, the survival rate drops dramatically. Too early and too aggressive an approach to the tumor can in turn unnecessarily impair the patient's quality of life. E. g. the surgical removal of the prostate may lead to incontinence and impotence. Reliable diagnosis and staging of the disease is essential for successful treatment with high quality of life for the patient. A widespread diagnostic tool, besides palpation of the prostate by a physician, is the determination of tumor markers in the patient's blood. The most prominent marker for prostate cancer is the concentration of prostate-specific antigen (PSA) in the blood. However, the significance of the PSA concentration is controversial, since patients with slightly elevated values often do not have prostate cancer, whereas 15% of patients with prostate cancer do not show an increased PSA concentration in the blood. Another target structure for the diagnosis of prostate tumors is the prostate-specific membrane antigen (PSMA). In contrast to PSA, PSMA cannot be detected in the blood. It is a membrane-bound glycoprotein with enzymatic activity. Its function is cleavage of C-terminal glutamate from N-acetyl aspartyl glutamate (NAAG) and folic acid (poly)-Y-glutamate. PSMA rarely occurs in normal tissue, but is strongly overexpressed by prostate carcinoma cells, the expression closely correlating with the stage of the tumor disease. Also, 40% of lymph nodes and bone metastases from prostate carcinomas express PSMA.

One strategy for molecular targeting of PSMA is to use antibodies to bind to the protein structure of PSMA. Another approach is to take advantage of the well understood enzymatic activity of PSMA. The enzymatic binding pocket of PSMA contains two $Zn^{2+}$ ions that bind glutamate. In front of the center with the two $Zn^{2+}$ ions there is an aromatic binding pocket. The protein is able to expand and adapt to the binding partner (induced fit), so that it can bind folic acid in addition to NAAG, whereby the pteroic acid group docks in the aromatic binding pocket. The use of the enzymatic affinity of PSMA enables the uptake of a substrate into the cell (endocytosis) independently of enzymatic cleavage of the substrate.

Therefore, PSMA inhibitors are particularly well suited as targeting vectors for diagnostic imaging and theranostic radiopharmaceuticals or radiotracers. The radioactively labeled inhibitors bind to the active center of the enzyme, but are not converted there. The bond between the inhibitor and the radioactive label is therefore not broken. Aided by endocytosis, the inhibitor with the radioactive label is absorbed into the cell and accumulated within the tumor cells.

Inhibitors with high affinity for PSMA usually contain a glutamate motif and an enzymatically non-cleavable structure. A highly effective PSMA inhibitor is 2-phosphonomethyl-glutaric acid or 2-Phosphonomethyl-pentanedioic acid (2-PMPA), in which the glutamate motif is bound to a phosphonate group that cannot be cleaved by PSMA.

Another group of PSMA inhibitors used in the clinically relevant radiopharmaceuticals PSMA-11 and PSMA-617 are urea-based inhibitors. It has proven advantageous to address the aromatic binding pocket of PSMA in addition to the binding pocket for the glutamate motif. For example, in the highly effective radiopharmaceutical PSMA-11, the L-lysine-urea-L-glutamate (KuE) binding motif is attached to an aromatic HBED chelator (N,N'-bis (2-hydroxy-5-(ethylene-beta-carboxy) benzyl) ethylenediamine N,N'-diacetate) via hexyl (hexyl linker).

If, on the other hand, L-lysine-urea-L-glutamate (KuE) is bound to the non-aromatic chelator DOTA (1,4,7,10-tetraazacyclododecane-1,4,7,10-tetraacetate), reduced affinity and accumulation in tumor tissue are observed. In order to still be able to use the DOTA chelator for a PSMA affine radiopharmaceutical with therapeutic radioisotopes such as $^{177}$Lu or $^{225}$Ac, the linker must be adapted. The highly effective radiopharmaceutical PSMA-617, the current gold standard, was found by means of targeted substitution of hexyl by various aromatic structures.

(FIG. 1: PSMA Inhibitors; FIG. 2: Labeling Precursor PSMA-11; FIG. 3: Labeling Precursor PSMA-617)

Tumor Stroma

Many tumors comprise malignant epithelial cells and are surrounded by several non-cancerous cell populations, including activated fibroblasts, endothelial cells, pericytes, immune regulatory cells, and cytokines in the extracellular matrix. These so-called stromal cells that surround the tumor play an important role in the development, growth and metastasis of carcinomas. A large part of the stromal cells are activated fibroblasts, which are known as cancer associated fibroblasts (CAFs). As the tumor progresses, CAFs change their morphology and biological function. These changes are induced by intercellular communication between cancer cells and CAFs. CAFs create a microenvironment that favors the growth of cancer cells. It has been shown that therapies that merely target cancer cells are inadequate. Effective therapies must address the tumor microenvironment, i. e. include CAFs. The fibroblast activation protein (FAP) is overexpressed by CAFs in more than 90% of all human carcinomas. Therefore, FAP represents a promising point of attack for radiological diagnostics and theranostics. FAP inhibitors (FAPI or FAPi) in particular are suitable as affine biological targeting vectors for FAP labeling precursors, in analogy to PSMA. FAP exhibits bimodal activity catalyzed by dipeptidyl peptidases (DPP) and prolyl oligopeptidases (PREP) via the same active site. Accordingly, two types of inhibitors come into consideration which inhibit the DPP and/or the PREP activity of FAP. Known inhibitors of FAP PREP activity have a low selectivity for FAP. In cancers that overexpress both FAP and PREP, PREP inhibitors can also be suitable as targeting vectors despite their low FAP selectivity. FIG. 4 shows a DOTA-conjugated FAP labeling precursor in which the chelator is coupled to the quinoline unit of the pharmacophore ((S)—N-(2-(2-cyano-4,4-difluoropyrrolidin-1-yl)-2-oxoethyl)-6-(4-amino-butyloxy)-quinoline-4-carboxamide via the 4-aminobutoxy functionality.

(FIG. 4: DOTA Conjugated FAP Labeling Precursor)

Bone Metastases

Bone metastases express farnesyl pyrophosphate synthase (FPPS), an enzyme in the HMG-CoA reductase (mevalonate) pathway. By inhibiting FPPS, the production of farnesyl, an important molecule for docking signal proteins to the cell membrane, is suppressed. As a result, apoptosis of carcinogenic bone cells is induced. FPPS is inhibited by bisphosphonates such as alendronate, pamidronate and zoledronate. For example, the tracer BPAMD with the targeting vector pamidronate is regularly used in the treatment of bone metastases. Zoledronate (ZOL), a hydroxy bisphosphonate with a heteroaromatic N unit, has proven to be a particularly effective tracer for theranostics of bone metastases. Zoledronate conjugated with the chelators NODAGA and DOTA (FIG. 5) are currently the most potent radio-theranostics for bone metastases.

(FIG. 5: Tracer DOTA Zoledronate (Left) and NODAGA Zoledronate (Right))

A large number of labeling precursors for diagnosis and theranostics of cancer diseases with radioactive isotopes are known in the prior art. WO 2015055318 A1 discloses radiotracers for the diagnosis and theranostics of prostate or epithelial carcinomas, such as, inter alia, the compound PSMA-617 shown in FIG. 3.

SUMMARY OF ADVANTAGEOUS INVENTIVE EMBODIMENTS

The present invention has the object to provide efficient labeling precursors for radiotracers for diagnosis and theranostics of prostate and stromal carcinomas with high tumor selectivity and dose.

BRIEF DESCRIPTION OF THE FIGURES

FIG. 1 illustrates the chemical structures of PSMA inhibitors;

FIG. 2 illustrates the chemical structure of labeling precursor PSMA-11;

FIG. 3 illustrates the chemical structure of the labeling precursor PSMA-617;

FIG. 4 illustrates the chemical structure of DOTA-conjugated FAP labeling precursor;

FIG. 5 illustrates the chemical structure of the tracer DOTA zoledronate (left) and NODAGA zolendronate (right);

FIG. 6A illustrates the chemical structures of chelators used in the invention;

FIG. 6B illustrates the chemical structures of chelators used in the invention;

FIG. 6C illustrates the chemical structures of chelators used in the invention

FIG. 7 illustrates the synthesis schema for QS-KuE precursor;

FIG. 8 illustrates the coupling schema of QS-KuE precursor to DOTA;

FIG. 9A illustrates the chemical structure of labeling precursor NOTA.QS.PSMA;

FIG. 9B illustrates the chemical structure of labeling precursors AAZTA.QS.PSMA and DATA.QS.PSMA;

FIG. 10 illustrates the chemical structure of squaric acid-conjugated PSMA-labeling precursor for radiohalides;

FIG. 11 illustrates the chemical formula of squaric acid-conjugated $^{18}$F-radiotracer for PSMA before cleavage of tert-butyl protecting groups;

FIG. 12 illustrates the chemical formula of squaric acid-conjugated PSMA-labeling precursors for $^{99m}$Tc;

FIG. 13 illustrates a synthesis schema for FAP-labeling precursor;

FIG. 14 illustrates the chemical structures of FAP-labeling precursors with squaric acid-coupling;

FIG. 15 illustrates the chemical structure associated with coordination by AAZTA.QS;

FIG. 16 illustrates the chemical formula of dimeric labeling precursors;

FIG. 17 illustrates the synthesis schema of DOA2 with two amine groups;

FIG. 18 illustrates the synthesis schema of KuE-QS;

FIG. 19 illustrates the synthesis schema of FAPI-QS;

FIG. 20 illustrates the chemical formula for the synthesis of dimers;

FIG. 24 illustrates the synthesis schema of NODAGA.QS.PAM;

FIG. 25A reproduces PET images of rats for injected tracers $^{68}$Ga-NOTA.QS.PAM and $^{68}$Ga-DOTA$^{Zol}$;

FIG. 25B reproduces PET images of rats for injected tracers $^{68}$Ga-NOTA.QS.PAM and $^{68}$Ga-DOTA$^{Zol}$;

DETAILED DESCRIPTION OF ADVANTAGEOUS INVENTIVE EMBODIMENTS

Figure 21A:
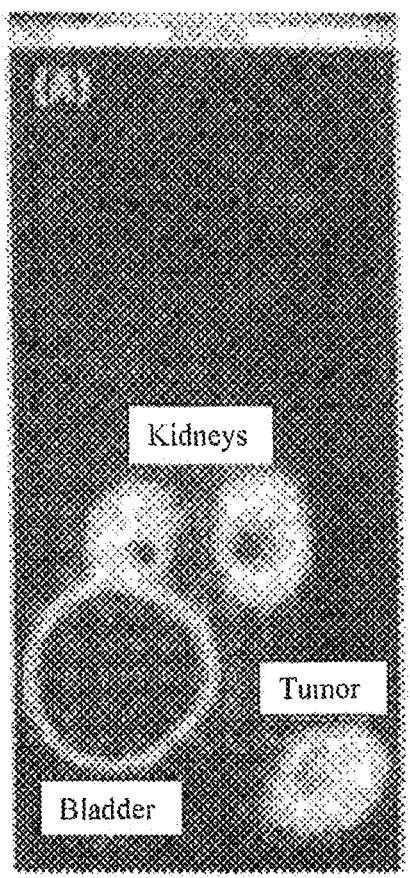
FIG. 21A reproduces PET images after injection of inventive tracer $^{68}$Ga-DOTA.QS.PSMA.

This object is achieved by a labeling precursor of structure (A), (B), (C), (D), (E), (F), (G), (H), (I), (J), (K) or (L) with (A)=Ch-$L_1$-QS-$TV_1$,
(B)=Ch-$L_1$-QS-$S_1$-$TV_1$,
(C)=Ch-$L_1$-QS-$S_1$-QS-$TV_1$,
(D)=Ch-$L_1$-QS-$S_2$-QS-$S_1$-$TV_1$,
(E)=$TV_2$-QS-$L_2$-Ch-$L_1$-QS-$TV_1$,
(F)=$TV_2$-$S_3$-QS-$L_2$-Ch-$L_1$-QS-$S_1$-$TV_1$,
(G)=$TV_2$-QS-$S_4$-QS-$L_2$-Ch-$L_1$-QS-$S_2$-QS-$TV_1$,
(H)=$TV_2$-$S_3$-QS-$S_4$-QS-$L_2$-Ch-$L_1$-QS-$S_2$-QS-$S_1$-$TV_1$,
(I)=Fg-$L_1$-QS-$TV_1$,
(J)=Fg-$L_1$-QS-$S_1$-$TV_1$,
(K)=Fg-$L_1$-QS-$S_2$-QS-$TV_1$,
(L)=Fg-$L_1$-QS-$S_2$-QS-$S_1$-$TV_1$;

comprising a chelator Ch, selected from the group comprising EDTA (ethylenediamine-tetraacetate), EDTMP (diethylenetriaminepenta(methylenephosphonic acid)), DTPA (diethylenetriaminepentacetate) and its derivatives, DOTA (dodeca-1,4,7,10-tetraamine-tetraacetate), DOTAGA (2-(1,4,7,10-tetraazacyclododecane-4,7,10)-pentanedioic acid) and other DOTA derivatives, TRITA (Trideca-1,4,7,10-tetraamine-tetraacetate), TETA (tetradeca-1,4,8,11-tetraamine-tetraacetate) and its derivatives, NOTA (Nona-1,4,7-triamine-triacetate) and its derivatives such as NOTAGA (1,4,7-triazacyclononane,1-glutaric acid,4,7-acetate), NOPO (1,4,7-triazacyclononane-1,4-bis[methylene(hydroxymethyl)phosphinic acid]-7-[methylene(2-carboxyethyl)phosphinic acid]), PEPA (pentadeca-1,4,7,10,13-pentaamine pentaacetate), HEHA (hexadeca-1,4,7,10,13,16-hexaamine-hexaacetate) and its derivatives, HBED (Hydroxybenzyl-ethylene-diamine) and its derivatives, DEDPA and its derivatives, such as $H_2$DEDPA (1,2-[[6-(carboxylate)pyridin-2-yl]methylamine]ethane), DFO (deferoxamine) and its derivatives, Trishydroxypyridinone (THP) and its derivatives such as YM103, TRAP (Triazacyclononane phosphinic acid), TEAP (Tetraazycyclodecane phosphinic acid) and its derivatives, AAZTA (6-Amino-6-methylperhydro-1,4-diazepine-N,N,N',N'-tetraacetate) and derivatives such as DATA ((6-pentanoic acid)-6-(amino)methyl-1,4-diazepine triacetate); SarAr (1-N-(4-aminobenzyl)-3,6,10,13,16,19-hexaazabicyclo[6.6.6]-eicosan-1,8-diamine) and salts thereof, aminothiols and their derivatives of the type

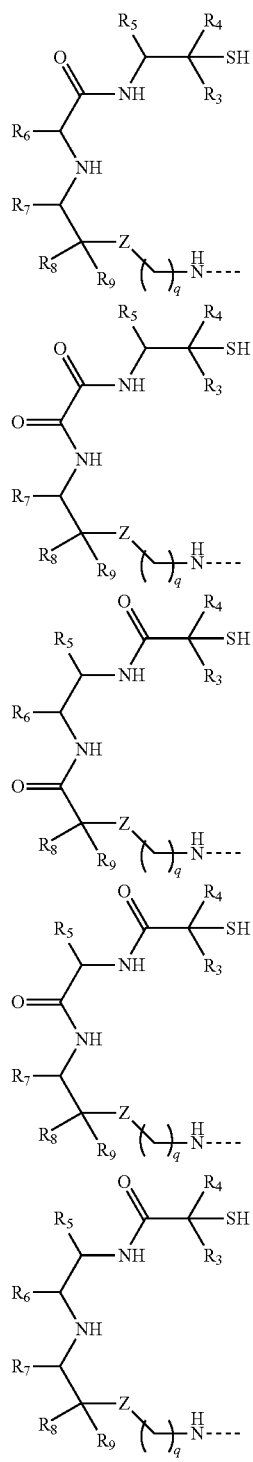

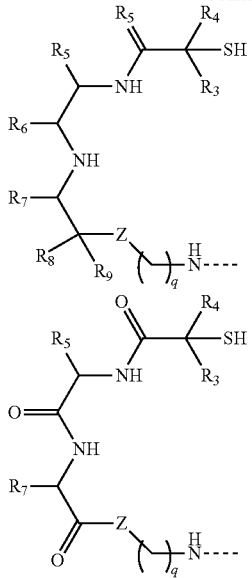

$q = 1, 2, 3, 4$ or $5$
$Z = S$ or $NH$
$R_3 = H$, unsubstituted or substituted alkyl
$R_4 =$ "
$R_5 =$ "
$R_6 =$ "
$R_7 =$ "
$R_8 =$ "
$R_9 = H$, unsubstituted or substituted alkyl or a fluorination group Fg selected from the group comprising

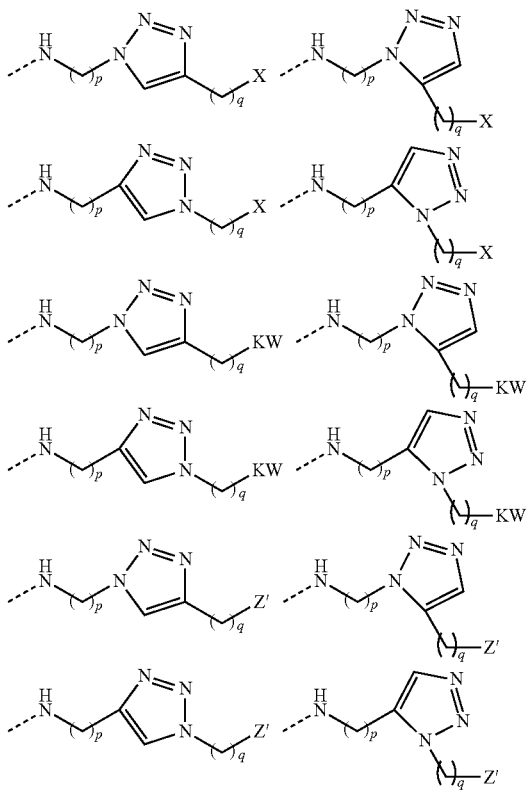

-continued

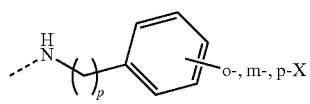

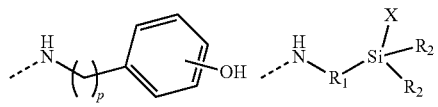

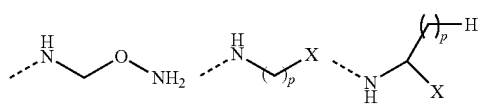

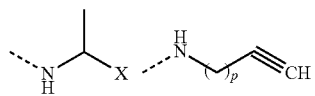

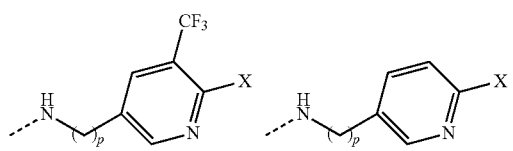

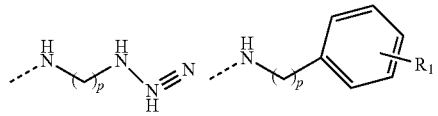

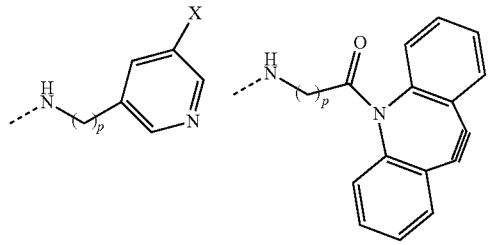

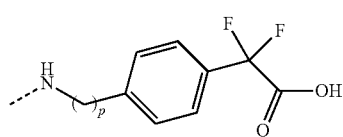

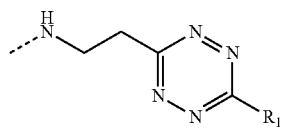

-continued

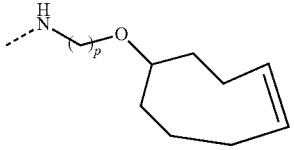

p = 0, 1, 2, 3, 4, 5, 6, 7, 8, 9, 10, 11 or 12
q = 0, 1, 2, 3, 4, 5, 6, 7, 8, 9, 10, 11 or 12
X = Cl, Br, I, Ts, Nos, MES, Tf or Non

KW = 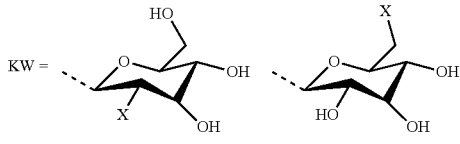

oder       oder

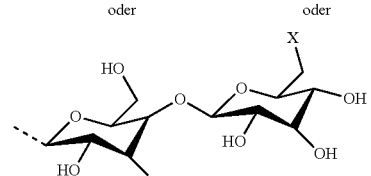

$R_1$ = alkyl, aryl, arylalkyl, methyl, 2-ethyl, 3-propyl, 2-, 3-, 4-phenyl, 2-, 3-, 4-phenylmethyl or 2-, 3-, 4-phenylpropyl
$R_2$ = alkyl, aryl group or 3-methylisopropyl ether one or two linkers $L_1$ and $L_2$, which are selected independently of one another from the group comprising —$(CH_2)_m$—, —$(CH_2CH_2O)_m$— and —$(CH_2)_mNH$— with m=1, 2, 3, 4, 5, 6, 7, 8, 9 or 10, residues of amide, carboxamide, phosphinate, alkyl, triazole, thiourea, ethylene and maleimide;
one or more squaric acid residues QS

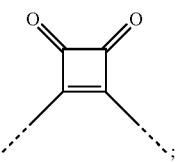

optionally one, two, three or four spacers $S_j$ with $1 \leq j \leq 4$, which are selected independently of one another from the group comprising —$(CH_2)_n$—, —$(CH_2)$—CH(COOH)—NH—, —$(CH_2CH_2O)_n$— and —$(CH_2)_nNH$— with n=1, 2, 3, 4, 5, 6, 7, 8, 9 or 10, residues of amide, carboxamide, phosphinate, alkyl, triazole, thiourea, ethylene and maleimide; and
one or two targeting vectors $TV_1$ and $TV_2$, which are selected independently of one another from the group comprising residues of compounds of the structure [1] to [41] with

[1]

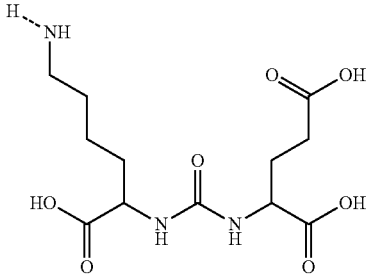

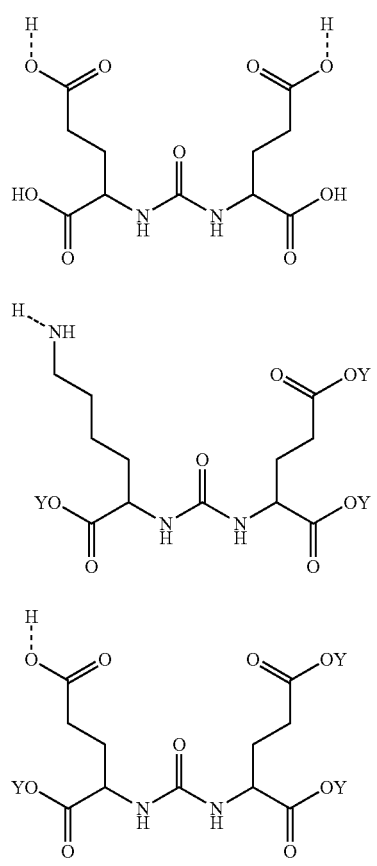
[2]
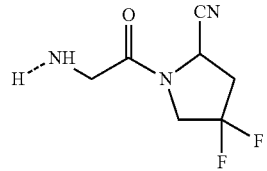
[3]
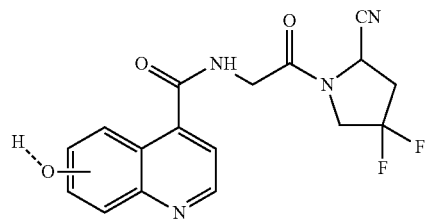
[4]
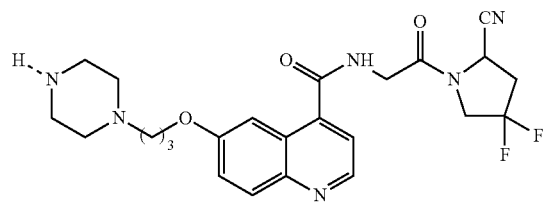
[5]
[6]
[7]
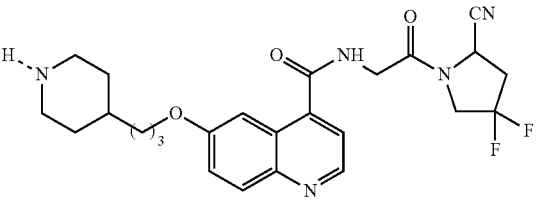
[8]
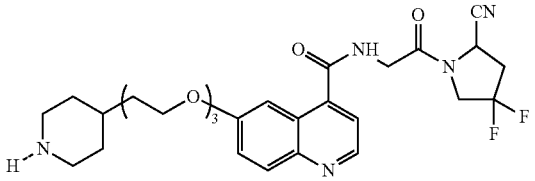
[9]
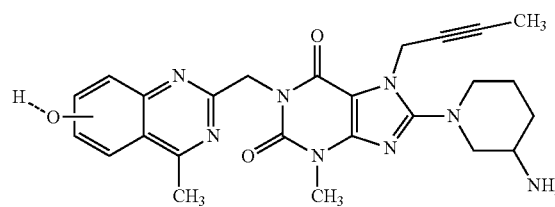
[10]
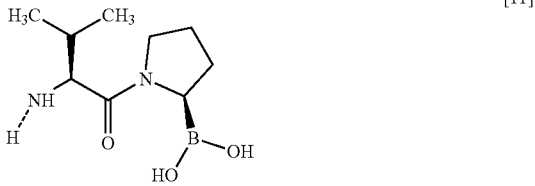
[11]
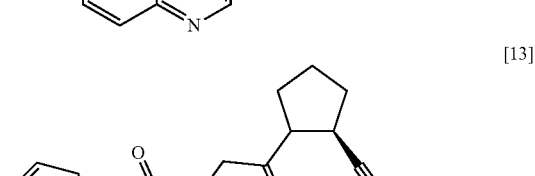
[12]
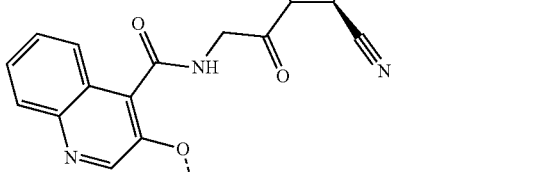
[13]
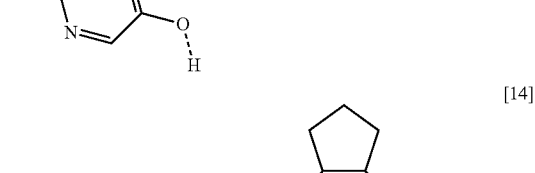
[14]

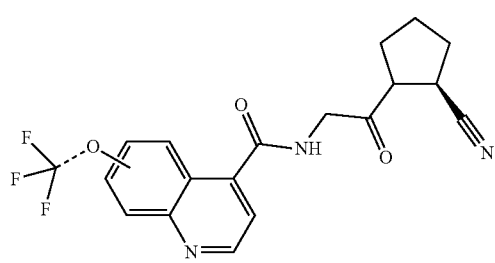
[15]
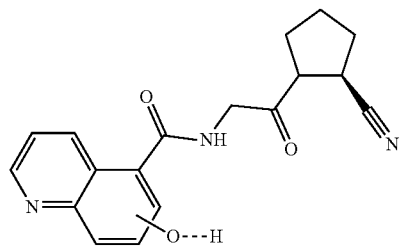
[16]
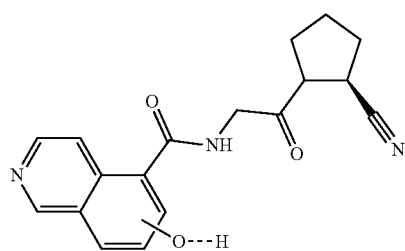
[17]
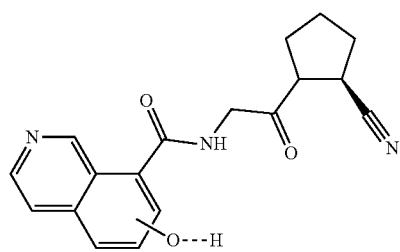
[18]
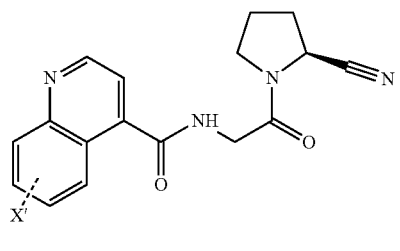
[19]
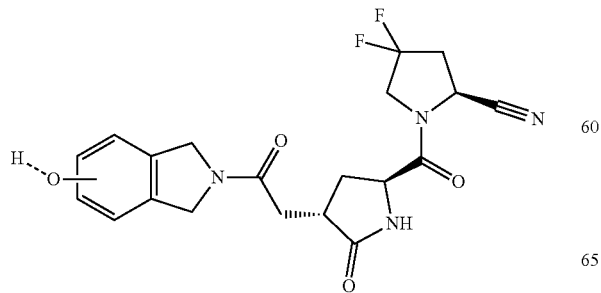
[20]
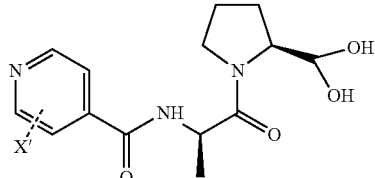
[21]
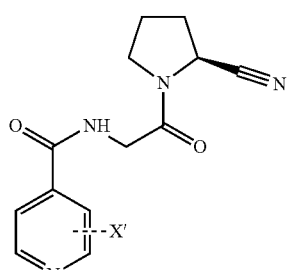
[22]
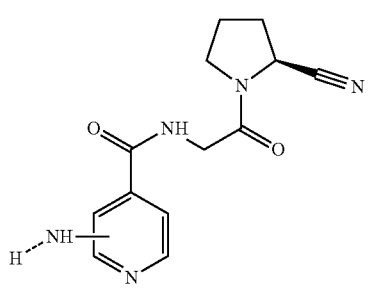
[23]
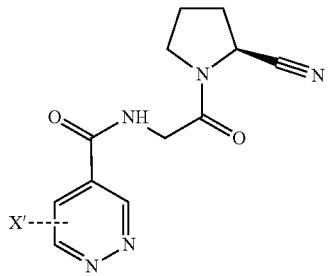
[24]
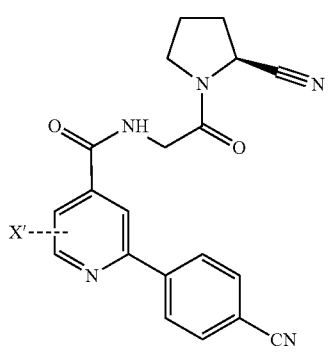
[25]

-continued
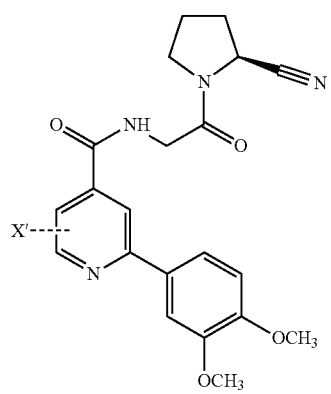
[26]
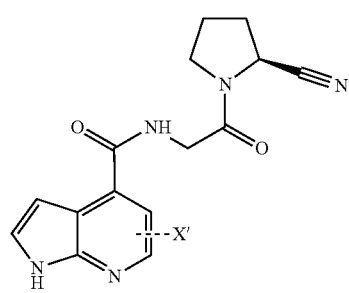
[27]
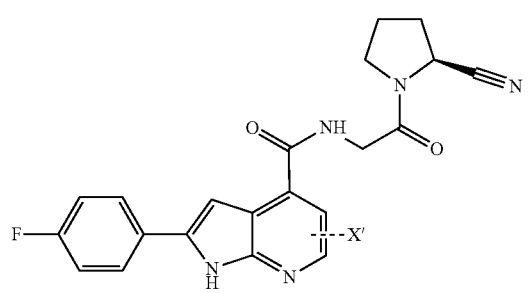
[28]
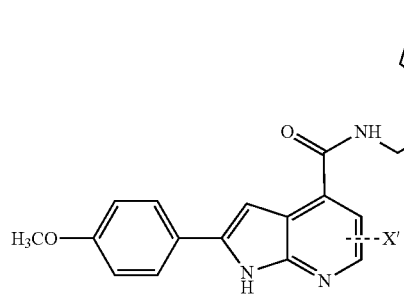
[29]
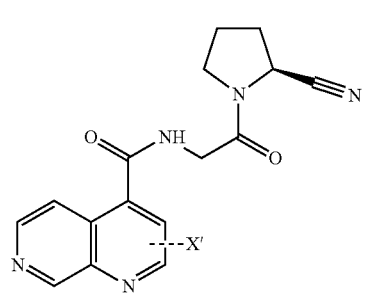
[30]
-continued
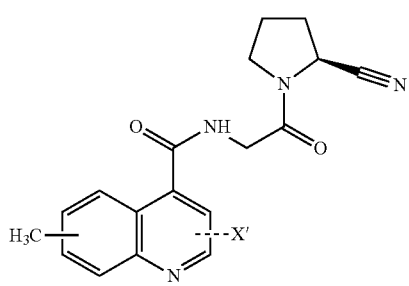
[31]
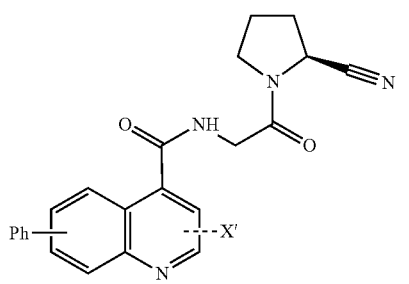
[32]
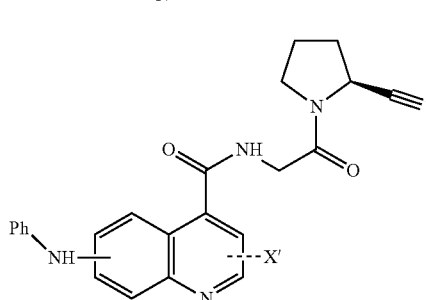
[33]
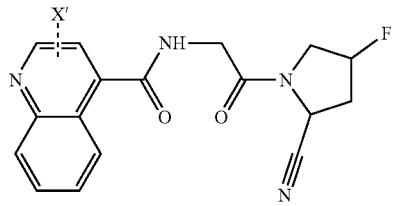
[34]
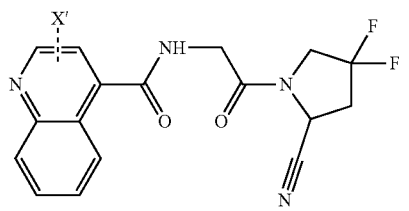
[35]
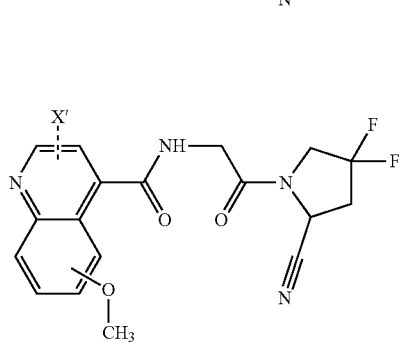
[36]

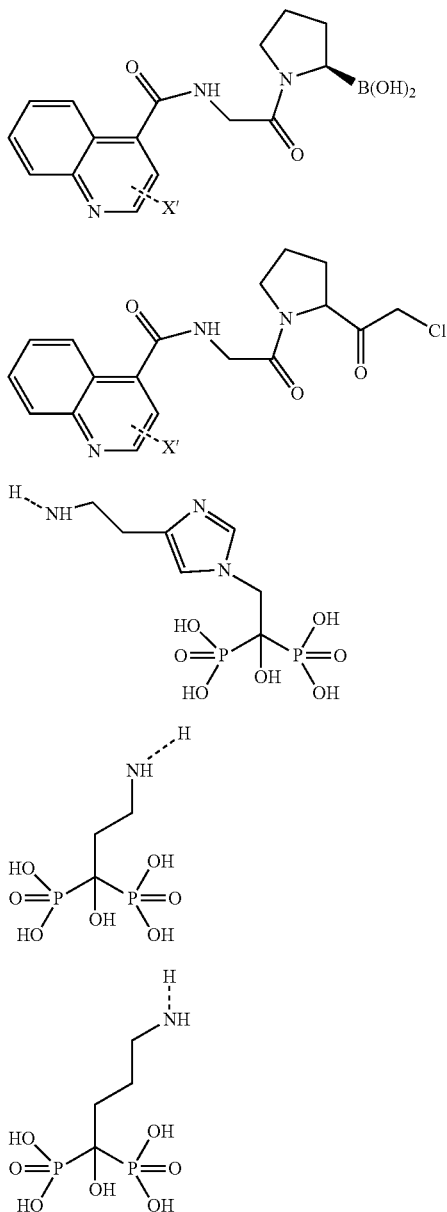

where Y is a protective group and X'=Cl, Br or I and the dashed bond of the targeting vectors [1]-[41] denotes a binding site with a leaving group.

Advantageous embodiments of the labeling precursors according to the invention are characterized in that the labeling precursor contains exactly one targeting vector $TV_1$;

the labeling precursor contains two targeting vectors $TV_1$ and $TV_2$ with $TV_1 \neq TV_2$ which are different from one another;

the labeling precursor contains two equal targeting vectors $TV_1$ and $TV_2$ with $TV_1=TV_2$;

the protective group Y is selected from the group comprising tert-butyloxycarbonyl (tert-butyl), trialkylsilyl groups, trimethylsilyl (—Si(CH$_3$)$_3$), triethylsilyl (—Si(CH$_2$CH$_3$)$_3$), isopropyldimethylsilyl (—Si(CH$_3$)$_2$C(CH$_3$)$_2$), tert-butyldimethylsilyl (—Si(CH$_3$)$_2$C(CH$_3$)$_3$) and tert-butoxydimethylsilyl (—Si(CH$_3$)$_2$OC(CH$_3$)$_3$);

the linkers $L_1$ and $L_2$ are equal ($L_1=L_2$);

the linkers $L_1$ and $L_2$ are different from one another ($L_1 \neq L_2$);

the spacers $S_1$ and $S_3$ are equal ($S_1=S_3$);

the spacers $S_1$ and $S_3$ are different from one another ($S_1 \neq S_3$);

the spacers $S_2$ and $S_4$ are equal ($S_2=S_4$); and/or the spacers $S_2$ and $S_4$ are different from one another ($S_2 \neq S_4$).

The labeling precursor according to the invention wherein the chelator Ch or the fluorination group Fg is intended for labeling with a radioisotope selected from the group comprising $^{44}$Sc, $^{47}$Sc, $^{55}$Co, $^{62}$Cu, $^{64}$Cu, $^{67}$Cu, $^{66}$Ga, $^{67}$Ga, $^{68}$Ga, $^{89}$Zr, $^{86}$Y, $^{90}$Y, $^{90}$Nb, $^{99m}$Tc, $^{111}$In, $^{135}$Sm, $^{140}$Pr, $^{159}$Gd, $^{149}$Tb, $^{160}$Tb, $^{161}$Tb, $^{165}$Er, $^{166}$Dy, $^{166}$Ho, $^{175}$Yb, $^{177}$Lu, $^{186}$Re, $^{188}$Re, $^{213}$Bi and $^{225}$Ac, respectively with $^{18}$F, $^{131}$I or $^{211}$At.

Accordingly, the invention further relates to radiotracer compounds containing one of the labeling precursors described above which comprise a chelator Ch and a complexed radioisotope selected from the group comprising $^{44}$Sc, $^{47}$Sc, $^{55}$Co, $^{62}$Cu, $^{64}$Cu, $^{67}$Cu, $^{66}$Ga, $^{67}$Ga, $^{68}$Ga, $^{89}$Zr, $^{86}$Y, $^{90}$Y, $^{90}$Nb, $^{99m}$Tc, $^{111}$In, $^{135}$Sm, $^{140}$Pr, $^{159}$Gd, $^{149}$Tb, $^{160}$Tb, $^{161}$Tb, $^{165}$Er, $^{166}$Dy, $^{166}$Ho, $^{175}$Yb, $^{177}$Lu, $^{186}$Re, $^{188}$Re, $^{213}$Bi and $^{225}$Ac, or a fluorination group Fg and a covalently bound radioisotope $^{18}$F, $^{131}$I or $^{211}$At or a covalently bound group containing $^{18}$F, $^{131}$I or $^{211}$At, in particular —CF$_2^{18}$F (trifluoromethyl).

The invention also relates to the use of the labeling precursors described above for the production of a radiopharmaceutical.

In an advantageous embodiment, the labeling precursors described above are used for the production of a radiopharmaceutical labeled with $^{44}$Sc, $^{47}$Sc, $^{55}$Co, $^{62}$Cu, $^{64}$Cu, $^{67}$Cu, $^{66}$Ga, $^{67}$Ga, $^{68}$Ga, $^{89}$Zr, $^{86}$Y, $^{90}$Y, $^{90}$Nb, $^{99m}$Tc, $^{111}$In, $^{135}$Sm, $^{140}$Pr, $^{159}$Gd, $^{149}$Tb, $^{160}$Tb, $^{161}$Tb, $^{165}$Er, $^{166}$Dy, $^{166}$Ho, $^{175}$Yb, $^{177}$Lu, $^{186}$Re, $^{188}$Re, $^{213}$Bi, $^{225}$Ac, $^{18}$F, $^{131}$I or $^{211}$At.

In an advantageous embodiment, the labeling precursors described above are used for the production of a radiopharmaceutical for positron emission tomography (PET) imaging diagnostics.

In an advantageous embodiment, the labeling precursors described above are used for the production of a radiopharmaceutical for single-photon emission computed tomography (SPECT) imaging diagnostics.

In an advantageous embodiment, the labeling precursors described above are used for the production of a radiopharmaceutical for the treatment of cancerous tumors.

A further object of the present invention is to provide a simple and efficient method for the synthesis of labeling precursors for the diagnosis and theranostics of cancer tumors expressing PSMA and/or FAP.

This object is achieved by a method comprising the steps of conjugating a chelator Ch or a fluorination group Fg with a linker $L_1$ to form a precursor $P_1$=Ch-$L_1$ or $P_1$=Fg-$L_1$ or conjugation of a chelator Ch or a fluorination group Fg with a linker $L_1$ and squaric acid QS to form a precursor $P_2$=Ch-$L_1$-QS or $P_2$=Fg-$L_1$-QS or conjugation of a chelator Ch with linkers $L_1$ and $L_2$ to form a precursor $P_3$=$L_2$-Ch-$L_1$ or conjugation of a chelator Ch with linkers $L_1$, $L_2$ and squaric acid QS to form a precursor $P_4$=QS-$L_2$-Ch-$L_1$-QS;

optionally, conjugation of a targeting vector $TV_1$ with squaric acid QS to form a precursor $P_5$=$TV_1$-QS or conjugation of a targeting vector $TV_1$ with squaric acid QS and a spacer $S_2$ to form a precursor $P_6=TV_1\text{-}QS\text{-}S_2$ or conjugation of a targeting vector $TV_1$ with a spacer $S_1$ to form a precursor $P_7=TV_1\text{-}S_1$ or conjugation of a targeting vector $TV_1$ with a spacer $S_1$ and squaric acid QS to form a precursor $P_8=TV_1\text{-}S_1\text{-}QS$ or conjugation of a targeting vector $TV_1$ with a spacer $S_1$, squaric acid QS and a spacer $S_2$ to form a precursor $P_9=TV_1\text{-}S_1\text{-}QS\text{-}S_2$;

optionally, conjugation of a targeting vector $TV_2$ with squaric acid QS to form a precursor $P_{10}=TV_2\text{-}QS$ or conjugation of a targeting vector $TV_2$ with squaric acid QS and a spacer $S_4$ to form a precursor $P_{11}=TV_2\text{-}QS\text{-}S_4$ or conjugation of a targeting vector $TV_2$ with a spacer $S_3$ to form a precursor $P_{12}=TV_2\text{-}S_3$ or conjugation of a targeting vector $TV_2$ with a spacer $S_3$ and squaric acid QS to form a precursor $P_{13}=TV_2\text{-}S_3\text{-}QS$ or conjugation of a targeting vector $TV_2$ with a Spacer $S_3$, squaric acid QS and a spacer $S_4$ to form a precursor $P_{14}=TV_2\text{-}S_3\text{-}QS\text{-}S_4$;

conjugation of a targeting vector $TV_1$ with the precursor $P_2$ or conjugation of the precursors $P_1$ and $P_5$ to form a labeling precursor of the structure $Ch\text{-}L_1\text{-}QS\text{-}TV_1$ or $Fg\text{-}L_1\text{-}QS\text{-}TV_1$ or conjugation of precursors $P_1$ and $P_8$ or $P_2$ and $P_7$ to form a labeling precursor of the structure $Ch\text{-}L_1\text{-}QS\text{-}S_1\text{-}TV_1$ or $Fg\text{-}L_1\text{-}QS\text{-}S_1\text{-}TV_1$ or conjugation of precursors $P_2$ and $P_9$ to form a labeling precursor of the structure $Ch\text{-}L_1\text{-}QS\text{-}S_2\text{-}QS\text{-}S_1\text{-}TV_1$ or $Fg\text{-}L_1\text{-}QS\text{-}S_2\text{-}QS\text{-}S_1\text{-}TV_1$; or conjugation of the precursors $P_3$, $P_5$ and $P_{10}$ to form a labeling precursor of the structure $TV_2\text{-}QS\text{-}L_2\text{-}Ch\text{-}L_1\text{-}QS\text{-}TV_1$ or conjugation of precursors $P_3$, $P_8$ and $P_{13}$ or $P_4$, $P_7$ and $P_{12}$ to form a labeling precursor of structure $TV_2\text{-}S_3\text{-}QS\text{-}L_2\text{-}Ch\text{-}L_1\text{-}QS\text{-}S_1\text{-}TV_1$ or conjugation of precursors $P_4$, $P_6$ and $P_{11}$ to form a labeling precursor of structure $TV_2\text{-}QS\text{-}S_4\text{-}QS\text{-}L_2\text{-}Ch\text{-}L_1\text{-}QS\text{-}S_2\text{-}QS\text{-}TV_1$ or conjugation of the precursors $P_4$, $P_9$ and $P_{14}$ to form a labeling precursor of the structure $TV_2\text{-}S_3\text{-}QS\text{-}S_4\text{-}QS\text{-}L_2\text{-}Ch\text{-}L_1\text{-}QS\text{-}S_2\text{-}QS\text{-}S_1 TV_1$;

wherein the chelator Ch is selected from the group comprising from the group comprising EDTA (ethylenediaminetetraacetate), EDTMP (diethylenetriaminepenta(methylene phosphonic acid)), DTPA (diethylenetriaminepentacetate) and its derivatives, DOTA (dodeca-1,4,7,10-tetraaminetetraacetate), DOTAGA (2-(1,4,7,10-tetraazacyclododecane-4,7,10)-pentanedioic acid) and other DOTA derivatives, TRITA (Trideca-1,4,7,10-tetraamine-tetraacetate), TETA (tetradeca-1,4,8,11-tetraamine-tetraacetate) and its derivatives, NOTA (Nona-1,4,7-triamine-triacetate) and its derivatives such as NOTAGA (1,4,7-triazacyclononane,1-glutaric acid,4,7-acetate), NOPO (1,4,7-triazacyclononane-1,4-bis[methylene(hydroxymethyl)phosphinic acid]-7-[methylene(2-carboxyethyl)phosphinic acid]), PEPA (pentadeca-1,4,7,10,13-pentaamine pentaacetate), HEHA (hexadeca-1,4,7,10,13,16-hexaamine-hexaacetate) and its derivatives, HBED (Hydroxybenzyl-ethylene-diamine) and its derivatives, DEDPA and its derivatives, such as H$_2$DEDPA (1,2-[[6-(carboxylate) pyridin-2-yl]methylamine]ethane), DFO (deferoxamine) and its derivatives, Trishydroxypyridinone (THP) and its derivatives such as YM103, TRAP (Triazacyclononane phosphinic acid), TEAP (Tetraazycyclodecane phosphinic acid) and its derivatives, AAZTA (6-Amino-6-methylperhydro-1,4-diazepine-N,N,N',N'-tetraacetate) and derivatives such as DATA ((6-pentanoic acid)-6-(amino)methyl-1,4-diazepine triacetate); SarAr (1-N-(4-aminobenzyl)-3,6,10,13,16,19-hexaazabicyclo[6.6.6]-eicosan-1,8-diamine) and salts thereof, aminothiols and their derivatives of the type

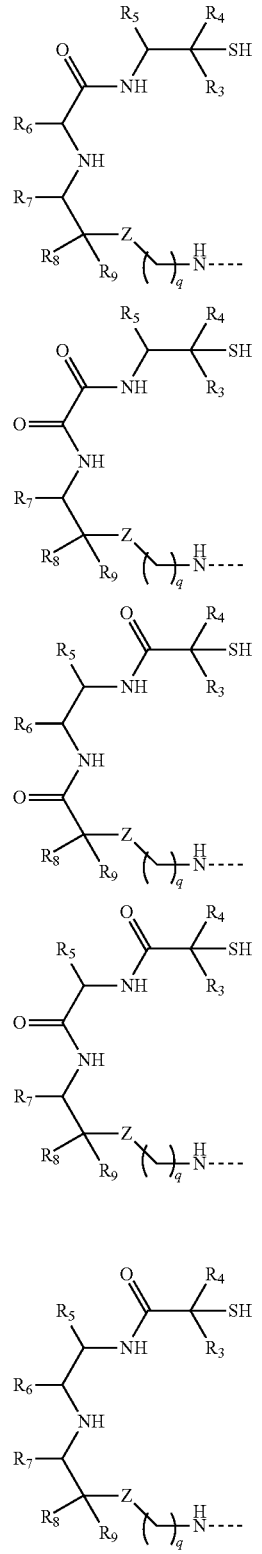

-continued
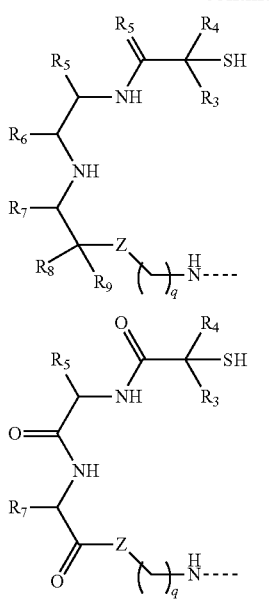
q = 1, 2, 3, 4 or 5
Z = S or NH
R₃ = H, unsubstituted or substituted alkyl
R₄ =            "
R₅ =            "
R₆ =            "
R₇ =            "
R₈ =            "
R₉ = H, unsubstituted or substituted alkyl
the fluorination group Fg is selected from the group comprising
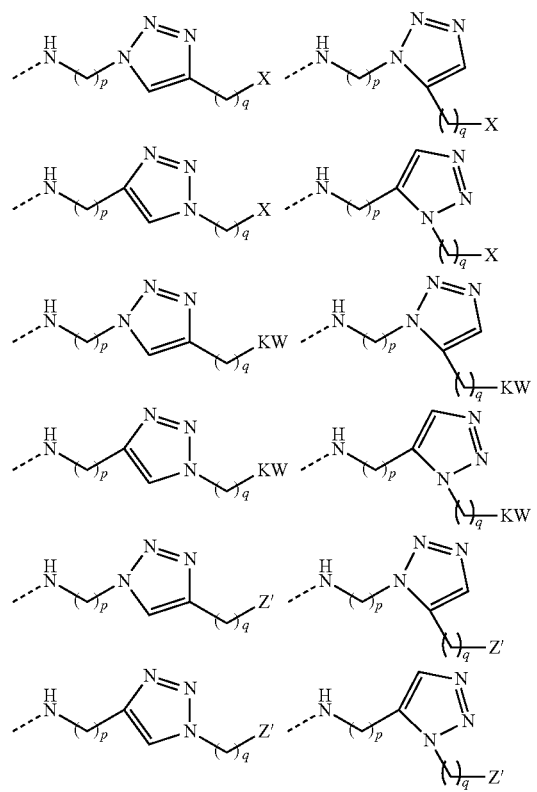
-continued
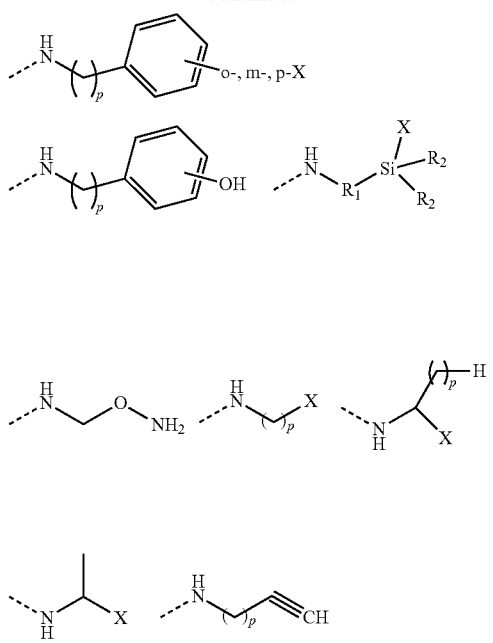

-continued

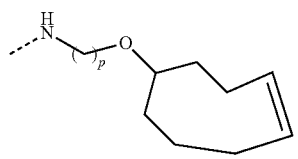

p = 0, 1, 2, 3, 4, 5, 6, 7, 8, 9, 10, 11 or 12
q = 0, 1, 2, 3, 4, 5, 6, 7, 8, 9, 10, 11 or 12
X = Cl, Br, I, Ts, Nos, MES, Tf or Non

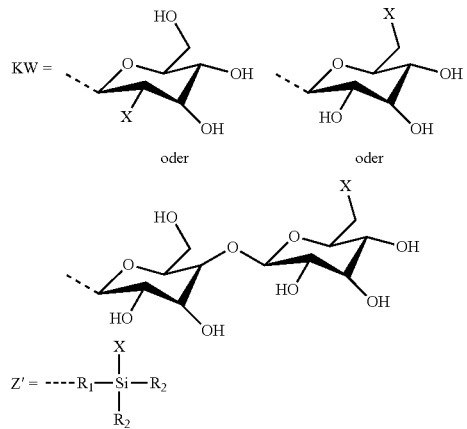

$R_1$ = alkyl, aryl, arylalkyl, methyl, 2-ethyl, 3-propyl, 2-, 3-, 4-phenyl,
2-, 3-, 4-phenylmethyl or 2-, 3-, 4-phenylpropyl
$R_2$ = alkyl, aryl group or 3-methylisopropyl ether the linkers $L_1$ and $L_2$ are selected independently of one another from the group comprising —$(CH_2)_m$—, —$(CH_2CH_2O)_m$— and —$(CH_2)_m NH$— with m=1, 2, 3, 4, 5, 6, 7, 8, 9 or 10, residues of amide, carboxamide, phosphinate, alkyl, triazole, thiourea, ethylene and maleimide;

the spacers $S_j$ with $1 \leq j \leq 4$ are selected independently of one another from the group comprising —$(CH_2)_n$—, —$(CH_2)$—$CH(COOH)$—$NH$—, —$(CH_2CH_2O)_n$— and —$(CH_2)_n$—$NH$— with n=1, 2, 3, 4, 5, 6, 7, 8, 9 or 10, residues of amide, carboxamide, phosphinate, alkyl, triazole, thiourea, ethylene and maleimide; and the targeting vectors $TV_1$ and $TV_2$ are selected independently of one another from the group comprising compounds of the structure [1] to [41] with

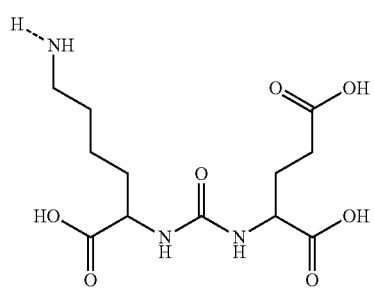

[1]

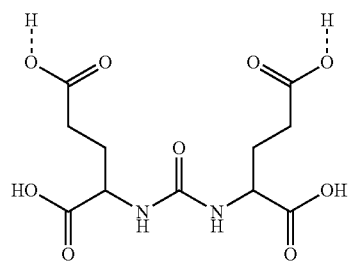

[2]

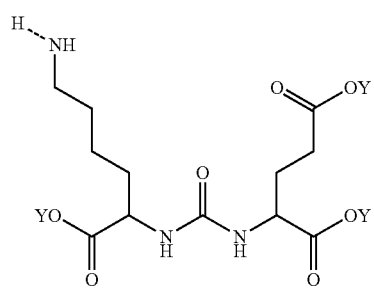

[3]

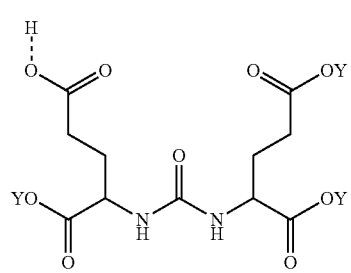

[4]

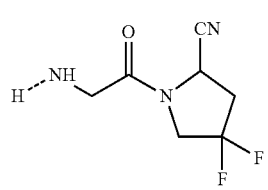

[5]

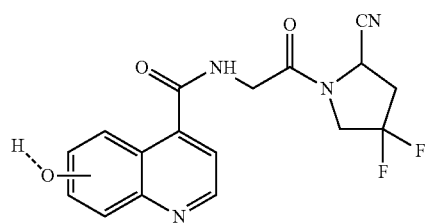

[6]

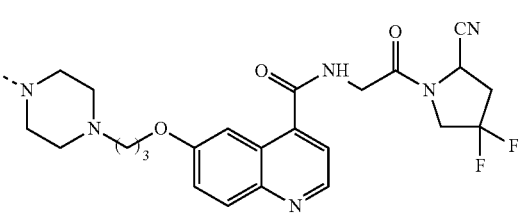

[7]

-continued
[8]
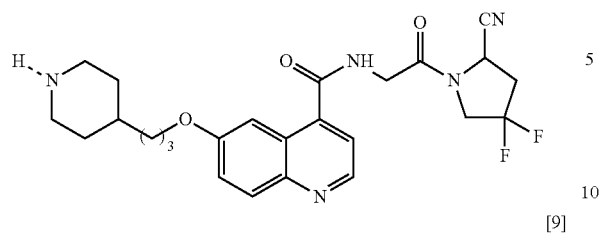
[9]
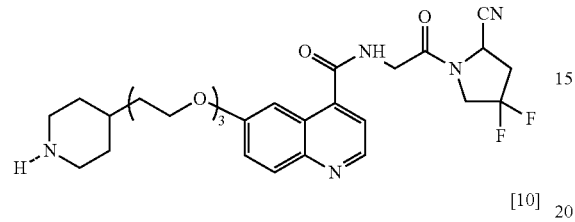
[10]
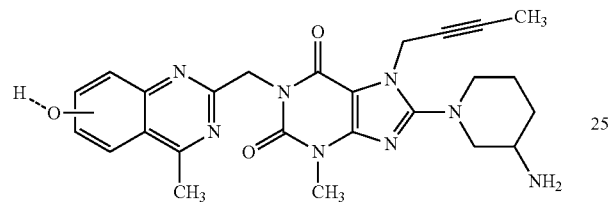
[11]
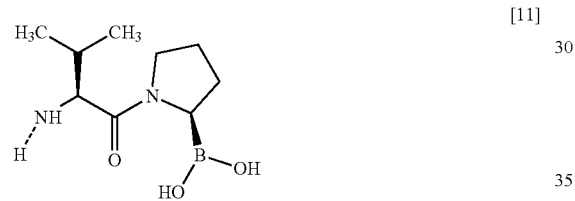
[12]
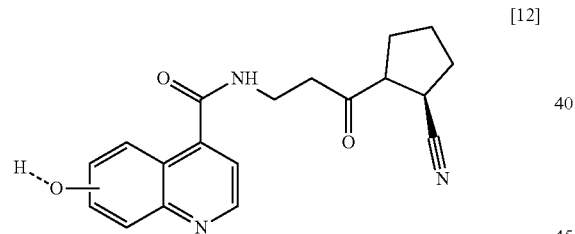
[13]
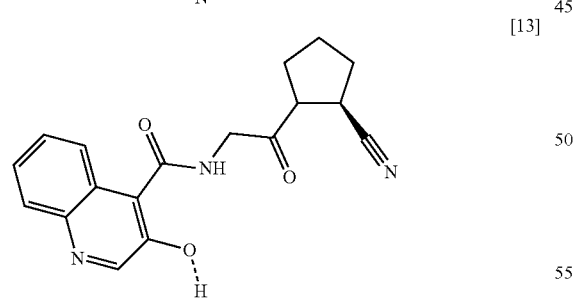
[14]
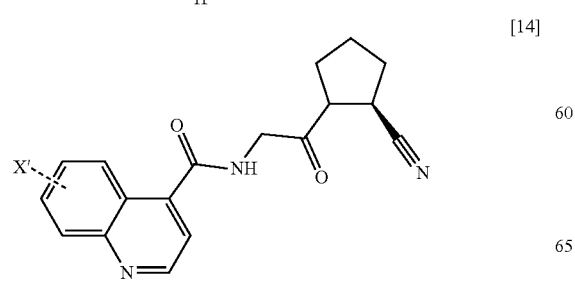
-continued
[15]
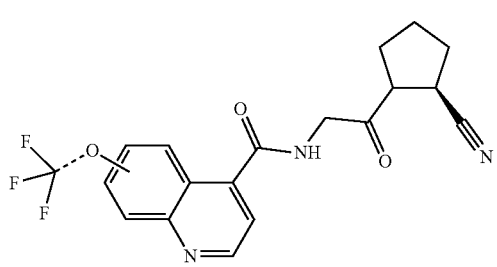
[16]
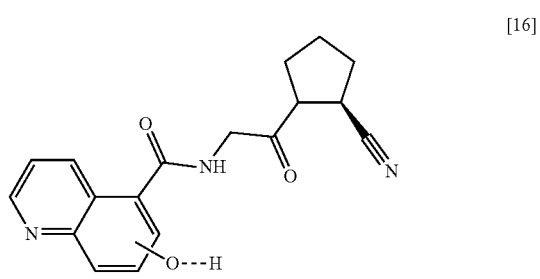
[17]
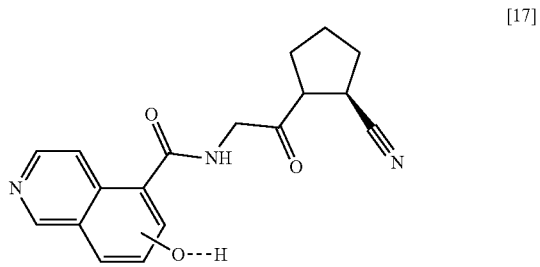
[18]
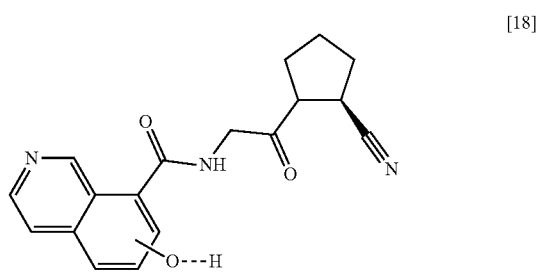
[19]
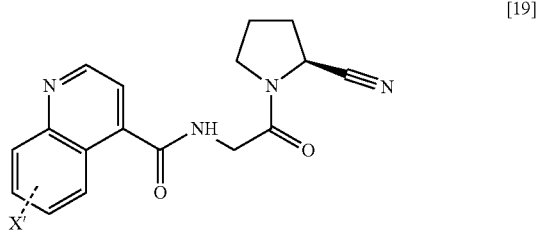
[20]
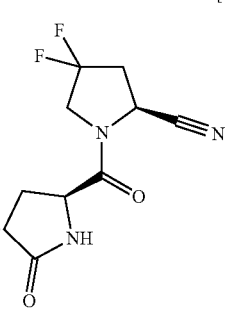

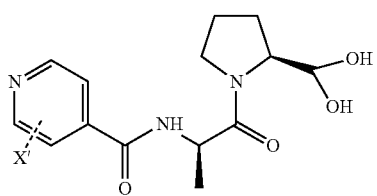
[21]
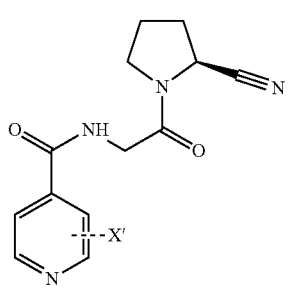
[22]
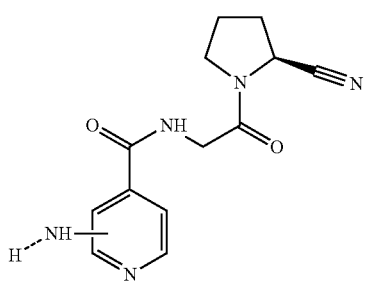
[23]
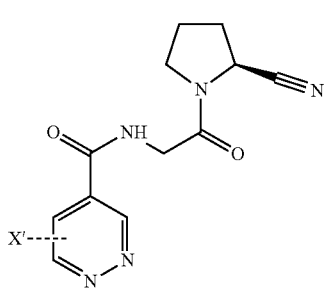
[24]
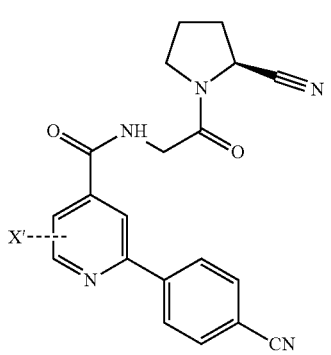
[25]
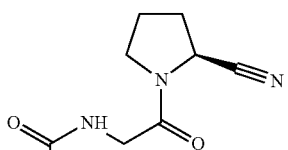
[26]
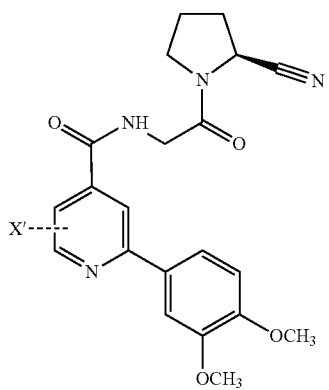
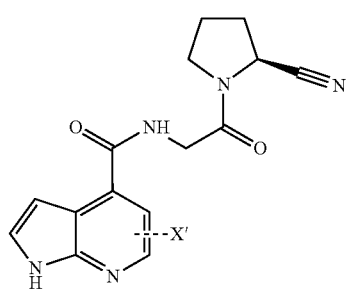
[27]
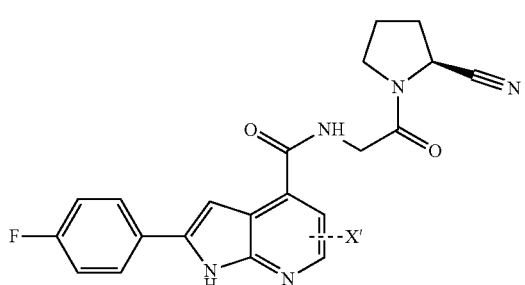
[28]
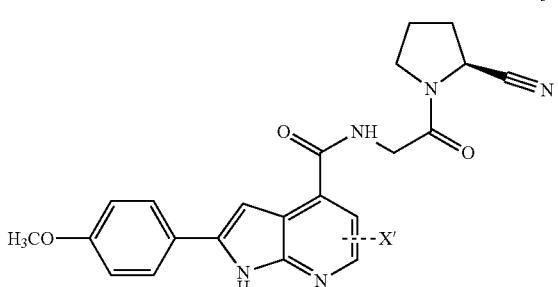
[29]
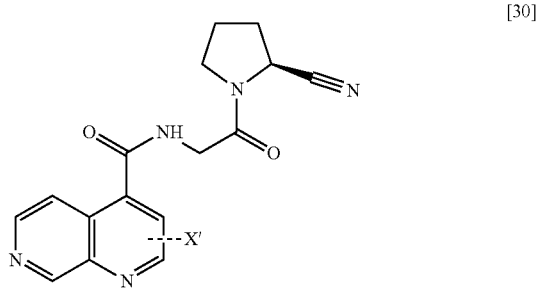
[30]

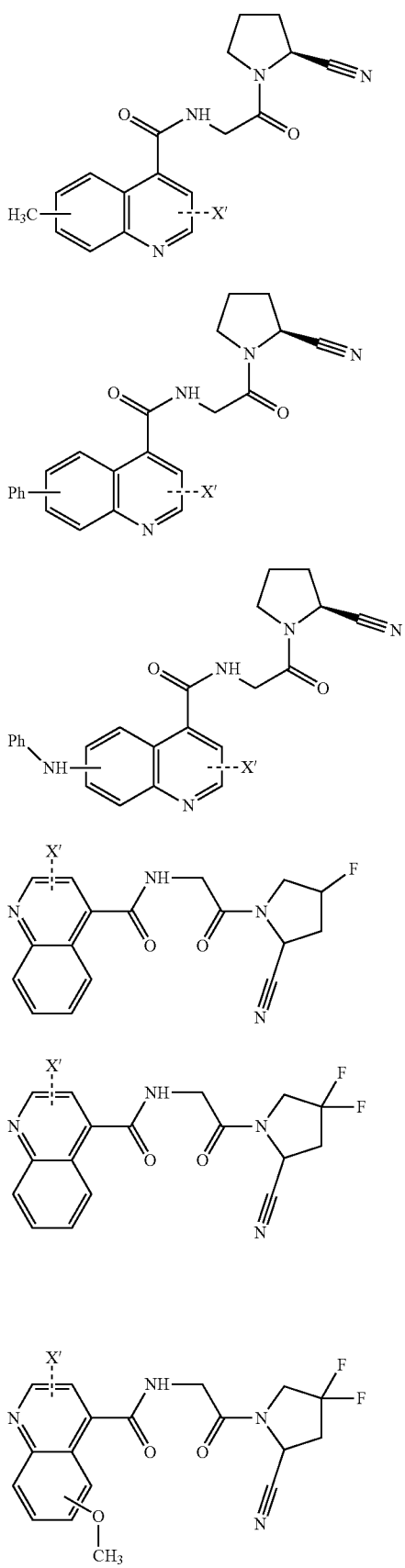

where Y is a protective group and X'=Cl, Br or I and the dashed linkage of the targeting vectors [1]-[41] denotes a binding site with a leaving group.

Advantageous embodiments of the method according to the invention are characterized in that the targeting vectors $TV_1$ and $TV_2$ are different from one another ($TV_1 \neq TV_2$);
the targeting vectors $TV_1$ and $TV_2$ are equal ($TV_1 = TV_2$);
the protective group Y is selected from the group comprising tert-butyloxycarbonyl (tert-butyl), trialkylsilyl groups, trimethylsilyl (—Si(CH$_3$)$_3$), triethylsilyl (—Si(CH$_2$CH$_3$)$_3$), isopropyldimethylsilyl (—Si(CH$_3$)$_2$C(CH$_3$)$_2$), tert-butyldimethylsilyl (—Si(CH$_3$)$_2$C(CH$_3$)$_3$) and tert-butoxydimethylsilyl (—Si(CH$_3$)$_2$OC(CH$_3$)$_3$);
the linkers $L_1$ and $L_2$ are equal ($L_1 = L_2$);
the linkers $L_1$ and $L_2$ are different from one another ($L_1 \neq L_2$);
the spacers $S_1$ and $S_3$ are equal ($S_1 = S_3$);

the spacers $S_1$ and $S_3$ are different from one another ($S_1 \neq S_3$);

the spacers $S_2$ and $S_4$ are equal ($S_2=S_4$); and/or the spacers $S_2$ and $S_4$ are different from one another ($S_2 \neq S_4$).

The fluorination group Fg comprises a leaving group X for labeling with one of the radioisotopes $^{18}$F, $^{131}$I or $^{211}$At. The leaving group X is equal to a residue of bromine (Br), chlorine (Cl), iodine (I), tosyl (—$SO_2$—$C_6H_4$—$CH_3$; abbreviated "Ts"), nosylate or Nitrobenzenesulfonate (—$OSO_2$—$C_6H_4$—$NO_2$; abbreviated "Nos"), 2-(N-Morpholino) ethanesulfonic acid (—$SO_3$—$(CH_2)_2$—$N(CH_2)_4O$; abbreviated "MES"), triflate or Trifluoro-methanesulfonyl (—$SO_2CF_3$; abbreviated "Tf") or nonaflate (—$OSO_2$—$C_4F_9$; abbreviated "Non").

In the context of the present invention, the following designations or abbreviations are used:

PSMA . . . Prostate specific membrane antigen;
FAP . . . Fibroblast activation protein;
FPPS . . . Farnesyl pyrophosphate synthase;
2-PMPA . . . 2-Phosphonomethyl glutaric acid;
KuE . . . L-lysine-urea-L-glutamate;
DOTA.QS.PSMA . . . labeling precursors, in particular with the structural formula according to FIG. 8, comprising DOTA (Dodeca-1,4,7,10-tetraamine-tetraacetate) as a chelator, to which one or two PSMA targeting vectors with the structural formula [1], [2], [3] and/or [4] are coupled via one or two linkers, squaric acid groups and spacers;
NOTA.QS.PSMA . . . labeling precursors, in particular with the structural formula according to FIG. 9, comprising NOTA (Nona-1,4,7-triamine triacetate) as a chelator, to which one or two PSMA targeting vectors with the structural formula [1], [2], [3] and/or [4] are coupled via one or two linkers, squaric acid groups and spacers;
AAZTA.QS.PSMA . . . labeling precursors, in particular with structural formula according to FIG. 9, comprising AAZTA as a chelator, to which one or two PSMA targeting vectors with the structural formula [1], [2], [3] and/or [4] are coupled via one or two linkers, squaric acid groups and spacers;
DATA.QS.PSMA . . . labeling precursors, in particular with structural formula according to FIG. 9, comprising DATA as a chelator, to which one or two PSMA targeting vectors with the structural formula [1], [2], [3] and/or [4] are coupled via one or two linkers, squaric acid groups and spacers;
DOTAGA.QS.PSMA . . . labeling precursors, including DOTAGA (2-(1,4,7,10-Tetraazacyclo-dodecane-4,7,10) pentanedioic acid) as a chelator, to which one or two PSMA targeting vectors with the structural formula [1], [2], [3] and/or [4] are coupled via one or two linkers, squaric acid groups and spacers;
NOTAGA.QS.PSMA . . . labeling precursor, comprising NOTAGA (1,4,7-triazacyclononane, 1-glutaric acid, 4,7-acetate) as a chelator, to which one or two PSMA targeting vectors with the structural formula [1], [2], [3] and/or [4] are coupled via one or two linkers, squaric acid groups and spacers;
TRAP.QS.PSMA . . . labeling precursors, comprising TRAP (triazacyclononanephosphinic acid) as a chelator, to which one or two PSMA targeting vectors with the structural formula [1], [2], [3] and/or [4] are coupled via one or two linkers, squaric acid groups and spacers;
NOTA.QS.PAM . . . labeling precursor, comprising NOTA as a chelator, to which one or two pamidronate targeting vectors according to structural formula [40] are coupled via one or two linkers, squaric acid groups and spacers.

Further abbreviations used in the context of the invention correspond to the above abbreviations, wherein another chelator, another fluorination group and/or another targeting vector—in particular a targeting vector for FAP according to the structural formulas [5] to [41]—is designated in an analogous manner by its respective abbreviation or acronym. For example, analogous derivatives that are used to target farnesyl pyrophosphate synthase (FPPS) in bone metastases are abbreviated as "PAM" for pamidronate and "ZOL" for zoledronate, depending on the type of bisphosphonate.

The labeling precursor according to the invention optionally comprises one or more spacers $S_j$ with $1 \leq j \leq 4$, i.e. one spacer $S_1$, two spacers $S_1$ and $S_2$, three spacers $S_1$, $S_2$ and $S_3$ or four spacers $S_1$, $S_2$, $S_3$ and $S_4$.

In the structural formulas [1]-[41] of the targeting vectors, the bonds provided for conjugation with a squaric acid group or a spacer $S_1$ or $S_2$ of the labeling precursor according to the invention are shown in dashed lines. The group conjugated via the dashed bond is a leaving group which is split off when the targeting vector is coupled with the squaric acid group or the spacer $S_1$ or $S_2$.

The invention is explained in more detail below by reference to figures and examples.

FIG. 6 shows the structure of some of the chelators Ch used according to the invention.

(FIG. 6: Chelators Used According to the Invention)

Example 1

Synthesis Strategy for PSMA Labeling Precursors

In the synthesis of the labeling precursors according to the invention squaric acid diesters are preferably used. As a result, a large number of, in some cases very complex, labeling precursors can be synthesized using simple reaction processes. Squaric acid diesters are characterized by their selective reactivity with amines, so that no protective groups are required when coupling chelators, linkers, spacers and targeting vectors. In addition, the coupling can be controlled via the pH value.

First, a targeting vector for PSMA is synthesized (see FIG. 7) and, after purification in an aqueous medium at pH=7, reacted with squaric acid diester to form a prostethic group or a precursor for coupling with a chelator (see FIG. 8).

(FIG. 7: Synthesis Scheme for QS-KuE Precursor)

E. g. in the case of a targeting vector for PSMA, the PSMA inhibitor L-lysine-urea-L-glutamate (KuE) is synthesized by means of a known process. Thereby, lysine bound to a solid phase, in particular a polymer resin and protected with tertbutyloxycarbonyl (tert-butyl), is reacted with double-tert-butyl-protected glutamic acid. After activation of the protected glutamic acid by triphosgene and the coupling to the solid phase-bound lysine, L-lysine-urea-L-glutamate (KuE) is split off by TFA and at the same time fully deprotected. The product can then be separated from free lysine by means of semi-preparative HPLC. The lysine-related yield of the above reaction is greater than 50%.

(FIG. 8: Coupling of a QS-KuE Precursor to DOTA)

The QS-KuE precursor is conjugated in phosphate buffer at pH 9 with the chelator DOTA to form the labeling precursor DOTA.QS.PSMA.

For the radiolabeling of the PSMA labeling precursors, $^{68}$Ga was eluted with 0.6 M HCl from an iThemba Ge/Ga generator and processed by means of aqueous ethanol elution over a cation exchange column. Radiolabeling takes place at pH values between 3.5 and 5.5 and temperatures between 25° C. and 95° C., depending on the chelator. The reaction progress was recorded by means of HPLC and IPTC in order to determine the kinetic parameters of the reaction.

Example 2

Labeling Precursor NOTA.QS.PSMA. AAZTA QS.PSMA and DATA.QS.PSMA

Using a synthesis according to the strategy described in Example 1 with chelators NOTA, AAZTA and DATA instead of DOTA yields the precursors NOTA.QS.PSMA, AAZTA.QS.PSMA and DATA.QS.PSMA shown in FIG. 9.

(FIG. 9: Labeling Precursors NOTA.QS.PSMA, AAZTA.QS.PSMA and DATA.QS.PSMA)

Example 3

PSMA Labeling Precursors for Radiohalides

The PSMA labeling precursors shown in FIG. 10 for radiolabeling with halide isotopes such as $^{18}$F and $^{131}$I were prepared using slightly modified reactions according to the synthesis schema of FIG. 10 corresponding radiotracer labeled with $^{18}$F is shown in FIG. 11.

(FIG. 10: Squaric Acid Conjugated PSMA Labeling Precursors for Radiohalides; FIG. 11: Squaric Acid-Conjugated $^{18}$F-Radiotracer for PSMA Before Splitting Off the Cert-Butyl Protective Groups)

Example 4

PSMA Labeling Precursor for $^{99m}$Tc

By means of a synthesis according to the strategy described in Example 1, the PSMA labeling precursors shown in FIG. 12 for radiolabeling with the isotope $^{99m}$Tc were prepared.

(FIG. 12: Squaric Acid Conjugated PSMA Labeling Precursors for $^{99m}$Tc with Aminothiol Based Chelators of the Type "$N_3S$")

Example 5

Synthesis Strategy for FAP Labeling Precursors (FIG. 13: Synthesis Strategy for FAP Labeling Precursors)

FIG. 14 shows two FAP labeling precursors which are prepared according to the synthesis strategy shown in FIG. 13.

(FIG. 14: FAP Labeling Precursors with Squaric Acid Coupling)

Example 6

QS as a Complexation Helper

For clinical use it is very important that the complexation takes place efficiently at low temperature. Squaric acids complex free metals and can thus protect the chelator center against unspecific coordination. This effect could be observed in the radiolabeling of TRAP.QS at different temperatures. TRAP complexes quantitatively at room tempera-ture. In contrast, an RCY value of only 50% was measured with TRAP.QS under the same conditions. If the temperature is increased, the labeling yield of TRAP.QS increases to quantitative values. This demonstrates the influence that squaric acid has on complexation. This effect illustrated in FIG. 15 enables the stable complexation of metals with a high coordination number, such as zirconium, by means of the AAZTA.QS chelator.

(FIG. 15: Coordination By Means of AAZTA.QS)

Example 7

Dimeric Labeling Precursors Each with Two KuE and FAPI Targeting Vectors (FIG. 16: Dimeric Labeling Precursors)
(i) Synthesis of the DO2A unit with two amine side groups:
(FIG. 17: Synthesis of DOA2 with Two Amine Groups)
(ii) Synthesis of the KuE-QS motif:
(FIG. 18: Synthesis of KuE-QS)
(iii) Synthesis of FAPI-QS, coupling of the 4,4-difluoro-proline-quinoline-4-carboxylic acid motif with QS:
(FIG. 19: Synthesis of FAPI-QS)
(iv) Coupling of the DO2A unit with KuE-QS and respectively FAPI-QS:
(FIG. 20: Synthesis of Dimers)

Example 8

$^{68}$Ga-DOTA.OS.PSMA Preclinical Study

Figure 21B:
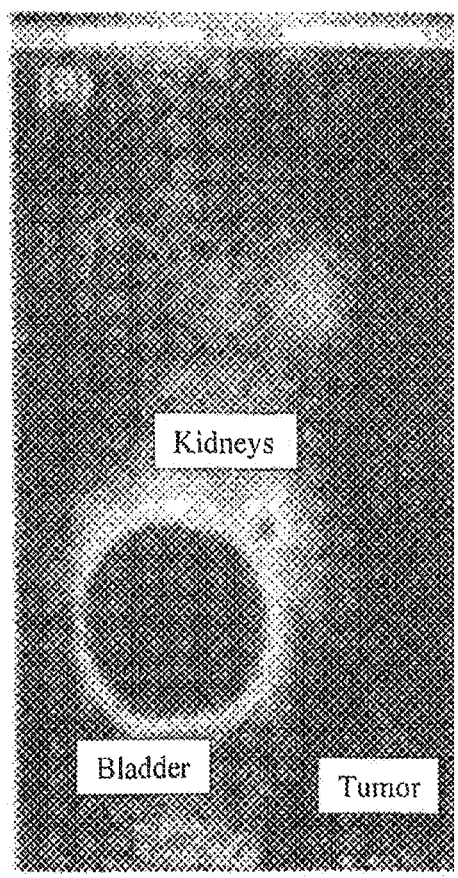
FIG. 21B reproduces PET images after injection of inventive tracer $^{68}$Ga-DOTA.QS.PSMA.

Using PET, preclinical comparative tests with radiotracers of type $^{68}$Ga-DOTA.QS.PSMA, $^{68}$Ga-PSMA-11 and $^{68}$Ga-PSMA-617 were carried out on NMRInu/nu nude mice with an LNCaP tumor on the right hind leg. FIG. 21 shows PET images 60 min after injection of the tracer $^{68}$Ga-DOTA.QS.PSMA according to the invention, partial images (A) and (B) showing the PET images of an unblocked tumor mouse and a tumor mouse blocked by means of co-injected 2-PMPA, respectively.

TABLE 1

Standardized intake values (SUV) of PSMA tracers

| | SUV | | |
|---|---|---|---|
| | DOTA.QS.PSMA | PSMA-11 | PSMA-617 |
| Tumor | 0.73 | 1.16 | 0.73 |
| Nieren | 0.43 | 4.71 | 0.27 |
| Leber | 0.27 | 0.25 | 0.29 |

Figure 22:
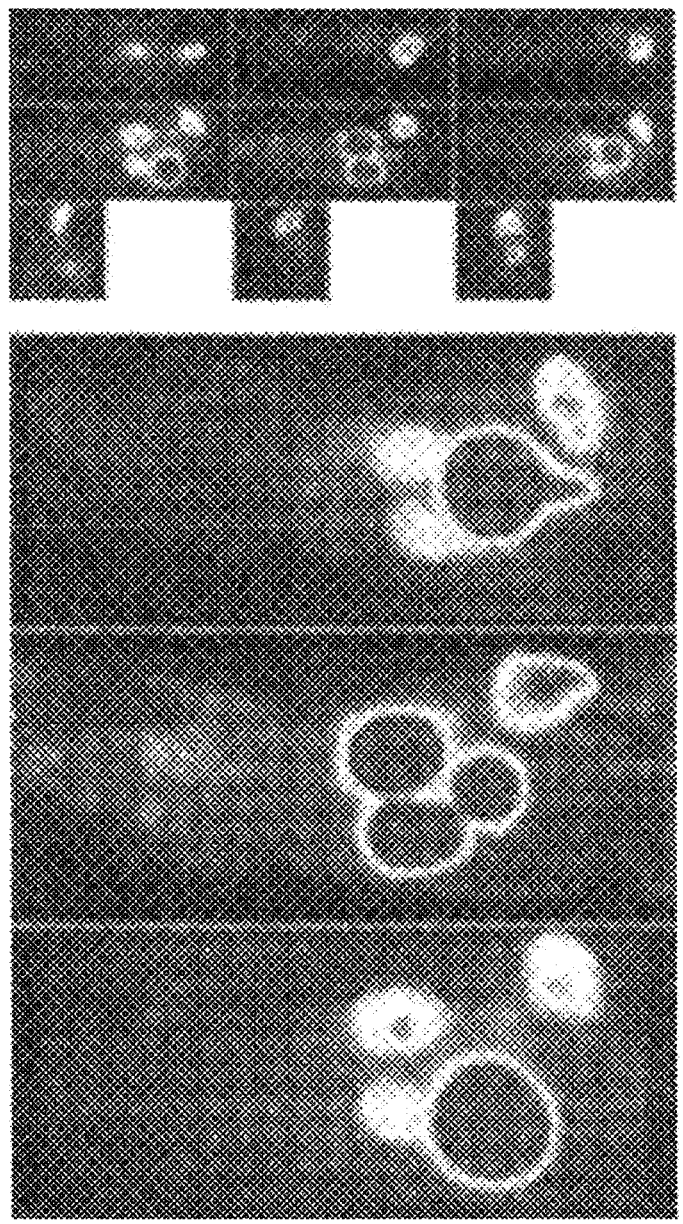
FIG. 22 reproduces PET images of strong tracer accumulation in the tumor.

From the PET images depicted in FIG. 22 it can be seen that the tracer accumulates strongly in the tumor. From the PET data a standardized uptake value (SUV) of 0.73 in the tumor was determined for $^{68}$Ga-DOTA.QS.PSMA. Biological distribution data ascertained by extraction of the organs and measurement of weight and activity show a slightly lower or equal tumor activity for $^{68}$Ga-DOTA.QS.PSMA as for $^{68}$Ga-PSMA-11 and $^{68}$Ga-PSMA-617. In contrast, the off-target activity in the kidneys is significantly lower than for $^{68}$Ga-PSMA-11.

Compared to other known radio tracers, the off-target enrichment of $^{68}$Ga-DOTA.QS.PSMA is significantly reduced in kidney and liver. $^{68}$Ga-DOTA.QS.PSMA has a high affinity for tumor tissue and improves the contrast and signal-to-noise ratio of imaging PET diagnosis of PCa primary tumors and especially PCa-affected lymph nodes in the pelvic area. The radiation exposure of the kidneys and neighboring organs is also reduced, which constitutes a significant advantage for theranostic treatment.

Analogous studies with $^{64}$CuTRAP.QS.PSMA and $^{68}$Ga-NOTAGA.QS.PSMA yielded comparable results. Furthermore, DOTA.QS.PSMA was labeled with $^{177}$Lu and $^{225}$Ac. First results on the radiological and physiological stability of these tracers indicate their suitability for theranostics.

Due to the influence of the aromatic binding pocket of PSMA on the affinity of PSMA inhibitors, some importance is assigned to the lipophilicity of PSMA tracers. Studies indicate that an increased lipophilicity also promotes the intake or endocytosis of the tracer in tumor tissue.

Accordingly, the lipophilicity of the tracers TRAP.QS.PSMA and DOTA.QS.PSMA according to the invention was determined by means of the HPLC method by Donovan and Pescatore (S. F. Donovan, M. C. Pescatore, J. Chromatogr. A 2002, 952, 47-61). For this purpose, the retention time of TRAP.QS.PSMA, DOTA.QS.PSMA and some calibration standards with known lipophilicity were measured in an ODP-HPLC column with a methanol/water gradient at pH 7. The log D values for TRAP.QS.PSMA and DOTA.QS.PSMA determined by linear regression of the retention times are shown in Table 2 together with literature values for PSMA-11 and PSMA-617.

Since DOTA.QS.PSMA has no retention on the ODP-HPLC column, only a maximum value is given for log D. TRAP.QS.PSMA, PSMA-11 and PSMA-617 have comparable lipophilicity. Surprisingly, the uptake of TRAP.QS.PSMA in the kidneys is significantly reduced compared to PSMA-11 and PSMA-617. This observation cannot be explained by the slight differences in the respective log D values. Apparently, affinity and endocytosis is not only influenced by lipophilicity, but other interactions such as π-π stacking in the enzymatic binding pocket also play a role. Squaric acid appears advantageous because of its small size compared to phenyl. In contrast, DOTA.QS.PSMA shows a considerably higher lipophilicity in connection with an uptake in the kidneys comparable to PSMA-617.

TABLE 2

| Lipophilicity of PSMA tracers | |
|---|---|
| Tracer | logD [nM] |
| TRAP.QS.PSMA | −1.5 ± 0.5 |
| DOTA.QS.PSMA | ≤−3.5 |
| PSMA-11 | −1.7 ± 0.6 |
| PSMA-617 | −2.0 ± 0.3 |

Figure 23:
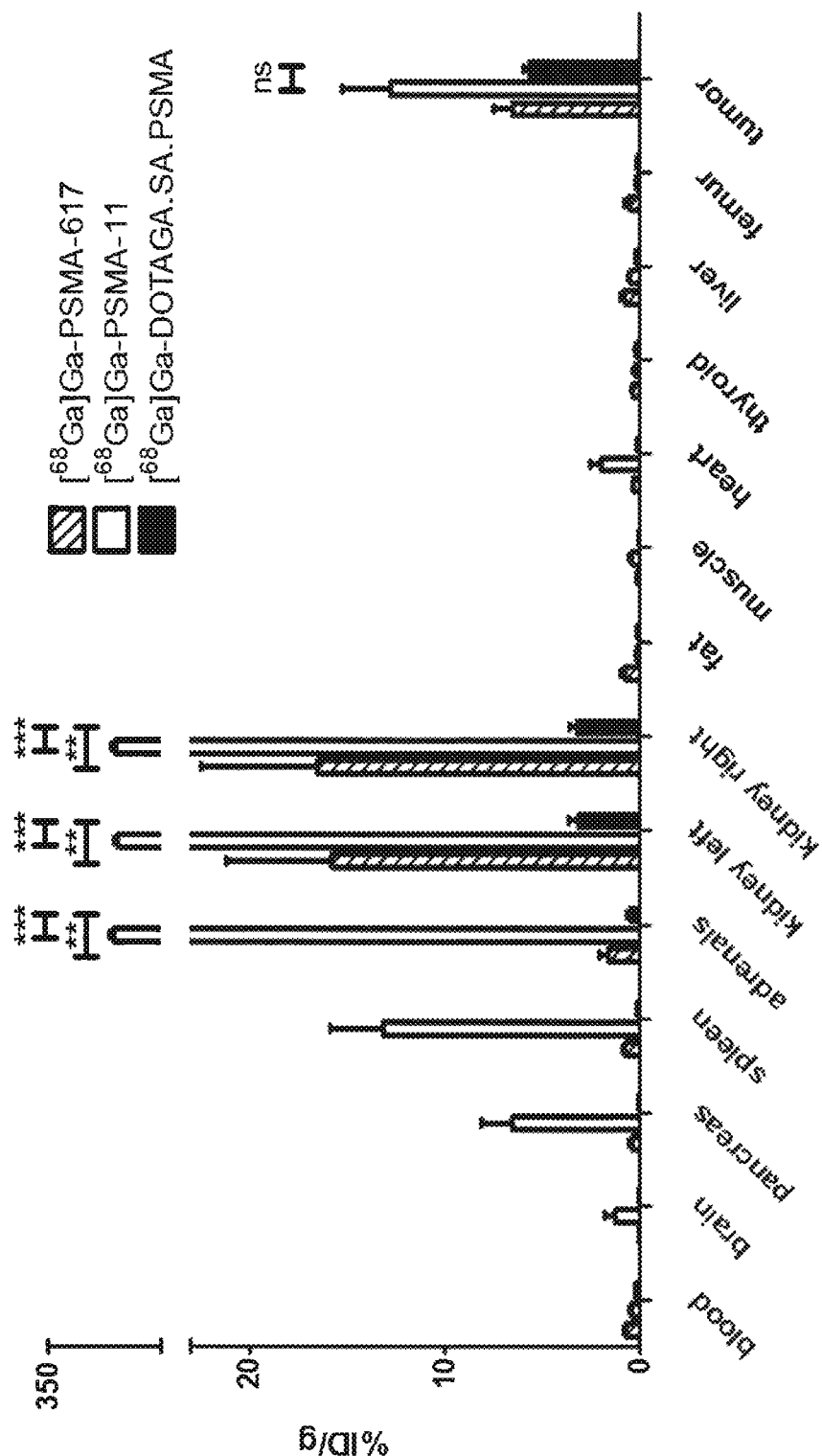
FIG. 23 is a graphical illustration of the organ distributions with various inventive radiotracers.

In addition, PET was used to carry out preclinical ex vivo tests with the radiotracers of type [$^{68}$Ga]Ga-DOTA.QS.PSMA, [$^{68}$Ga]Ga-PSMA-11 and [$^{68}$Ga]Ga-PSMA-617 on NMRInu/nu nude mice with an LNCap tumor. FIG. 23 shows the organ distributions of the corresponding compounds. The results obtained underline those obtained in the in vivo tests. Biological distribution data determined by extraction of the organs and measurement of weight and activity show that [$^{68}$Ga]Ga-DOTA.QS.PSMA has a slightly lower or the same tumor activity as [$^{68}$Ga]Ga-PSMA-11 and [$^{68}$Ga]Ga-PSMA-617. In contrast, the off-target activity in the kidney is significantly lower than for [$^{68}$Ga]Ga-PSMA-11.

Example 9

FPPS Tracer

Bisphosphonates such as alendronate, pamidronate and zoledronate (structural formula [39], [40] and [41] respectively) inhibit farnesyl pyrophosphate synthase (FPPS) and induce apoptosis in bone metastases.

For labeling bone metastases a squaric acid-coupled tracer NOTA.QS.PAM with chelator NOTA and targeting vector pamindronate (structural formula [40]) was synthesized in accord with the strategy described in Example 1. FIG. 24 illustrates the synthetic schema with reference to the NODAGA chelator.

(FIG. 24: Synthesis of NODAGA.QS.PAM)

The tracer NOTA.QS.PAM according to the invention and the clinically established reference tracer DOTA$^{Zol}$ were labeled with $^{68}$Ga, injected into young healthy Wistar rats, followed by recording of PET scans at intervals of 5 min, 60 min and 120 min after injection.

FIG. 25 shows the corresponding PET images for the tracers $^{68}$Ga-NOTA.QS.PAM and $^{68}$Ga-DOTA$^{Zol}$ 120 min after injection. Both tracers show a specific uptake in bone regions with increased remodeling rate, especially in the epiphyses, which are still growing in young rats. In addition to the skeleton, the bladder shows increased activity and indicates preferential renal excretion. In contrast, retention in soft tissue is extremely low.

Compared to $^{68}$Ga-DOTA$^{Zol}$, the renal excretion of $^{68}$Ga-NOTA.QS.PAM is slightly reduced. This observation is consistent with the renal excretion of PSMA tracers. This is the result of increased accumulation in the target tissue in association with accelerated renal excretion of free, non-specifically bound tracer. In terms of pharmacological kinetics, the inventive squaric acid-coupled tracers exhibit advantages over known tracers.

Figure 26:
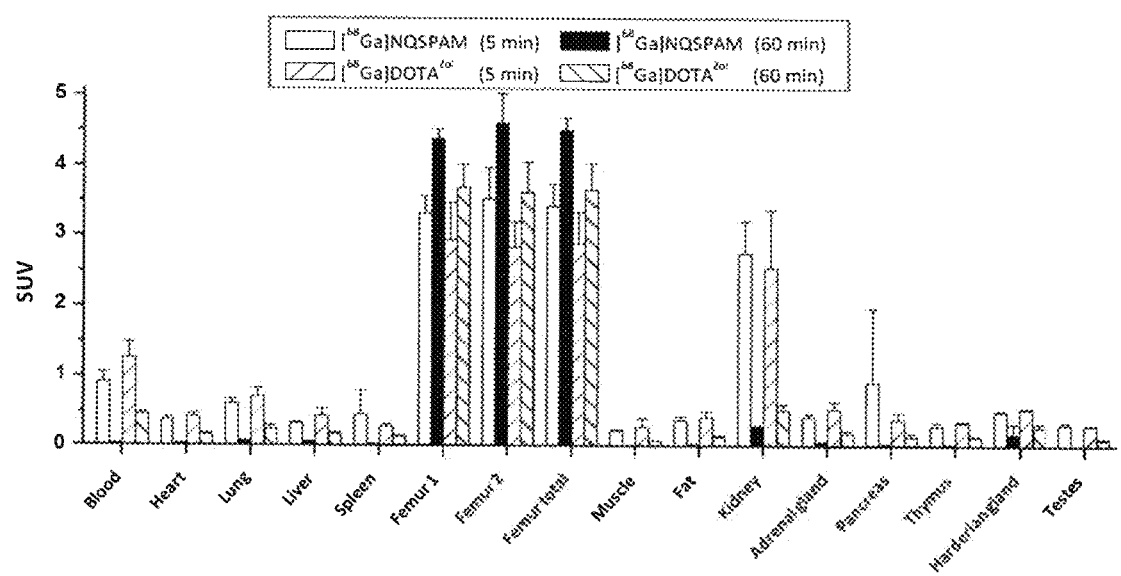
FIG. 26 is a bar graph illustrating the uptake values for $^{68}$Ga-NOTA.QS.PAM and $^{68}$Ga-DOTA$^{Zol}$ in different organs.

FIG. 26 shows the uptake values (SUV) for $^{68}$Ga-NOTA.QS.PAM and $^{68}$Ga-DOTA$^{Zol}$ in different organs at intervals of 5 min and 60 min after injection in the form of a bar graph. The organ distribution of the activity demonstrates that both tracers exhibit high uptake and retention in bone, whereby $^{68}$Ga-NOTA.QS.PAM has a slightly higher femur SUV (SUV femur: $^{68}$Ga-DOTA$^{Zol}$=3.7±0.4; $^{68}$Ga-NOTA.QS.PAM=4.5±0.2). Both tracers are characterized by renal excretion and low retention in the remaining tissue.

Example 10

QS.PSMA

Figure 27:
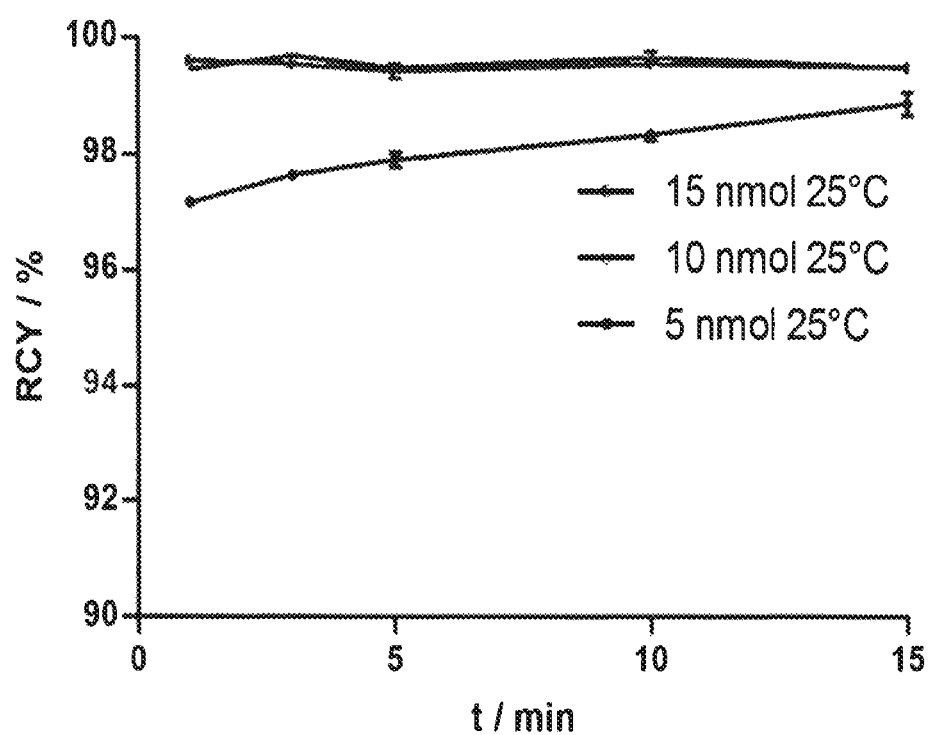
FIG. 27 graphically illustrates the radioactive labeling of compounds with $^{68}$Ga measured by radio-DC.
Figure 28:
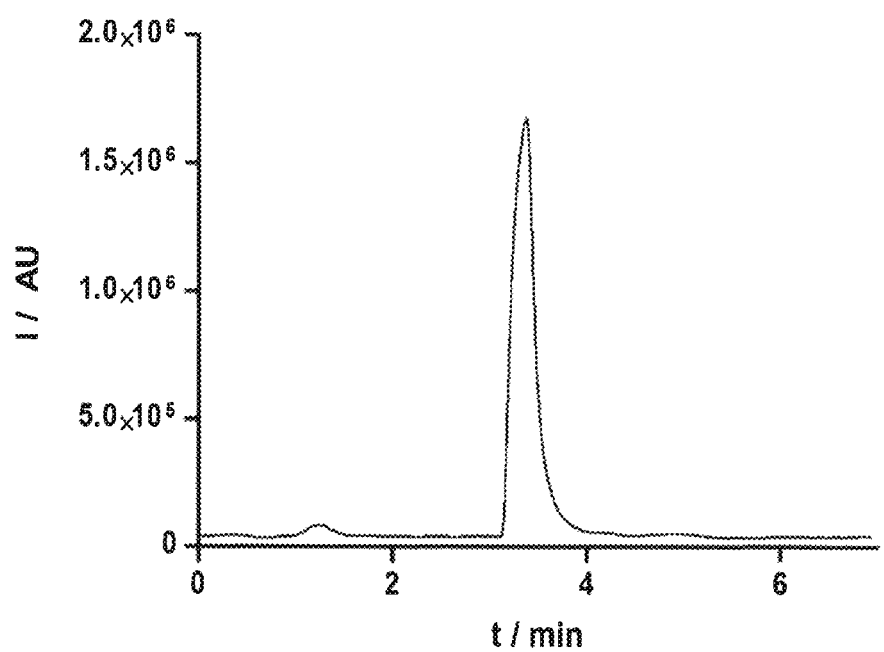
FIG. 28 graphically illustrate the radioactive labeling of compounds with $^{68}$Ga measured by radio-HPLC.

In order to elucidate the activity of QS, tests comparable to those for DOTA.QS.PSMA were carried out with NODAGA.QS.PSMA. FIGS. 27 and 28 show the radioactive labeling of the compounds with $^{68}$Ga, respectively measured by radio-DC (FIG. 27) and radio-HPLC (FIG. 28). Yields of more than 95% are achieved.

Figure 29:
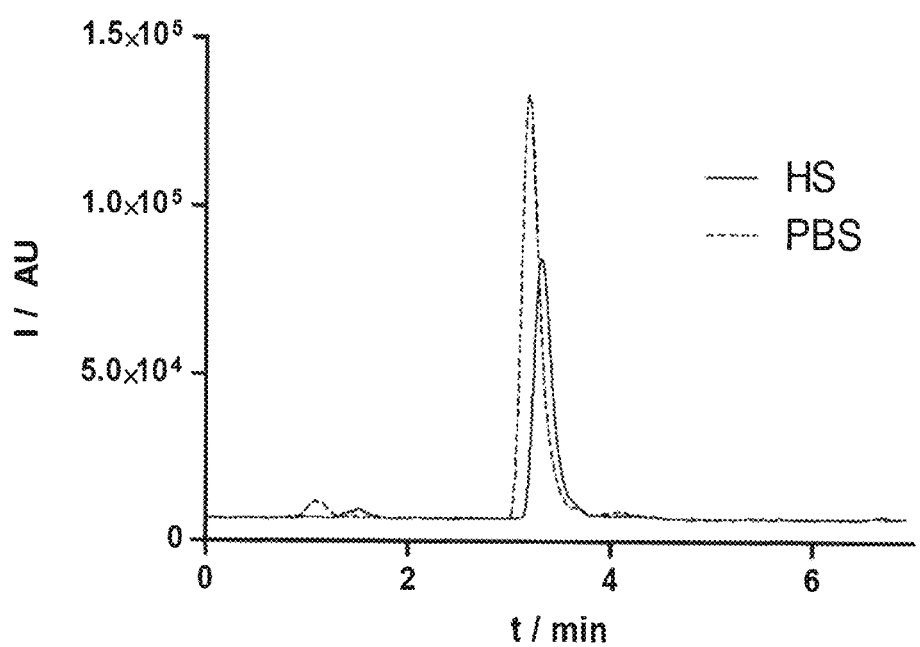
FIG. 29 graphically illustrates stability tests of compounds with $^{68}$Ga measured by HPLC.

Corresponding stability tests were carried out in human serum and in PBS buffer. The compounds show stabilities of more than 95% after 2 hours in PBS and HS. FIG. 29 shows the stability measured by HPLC.

Figure 30:
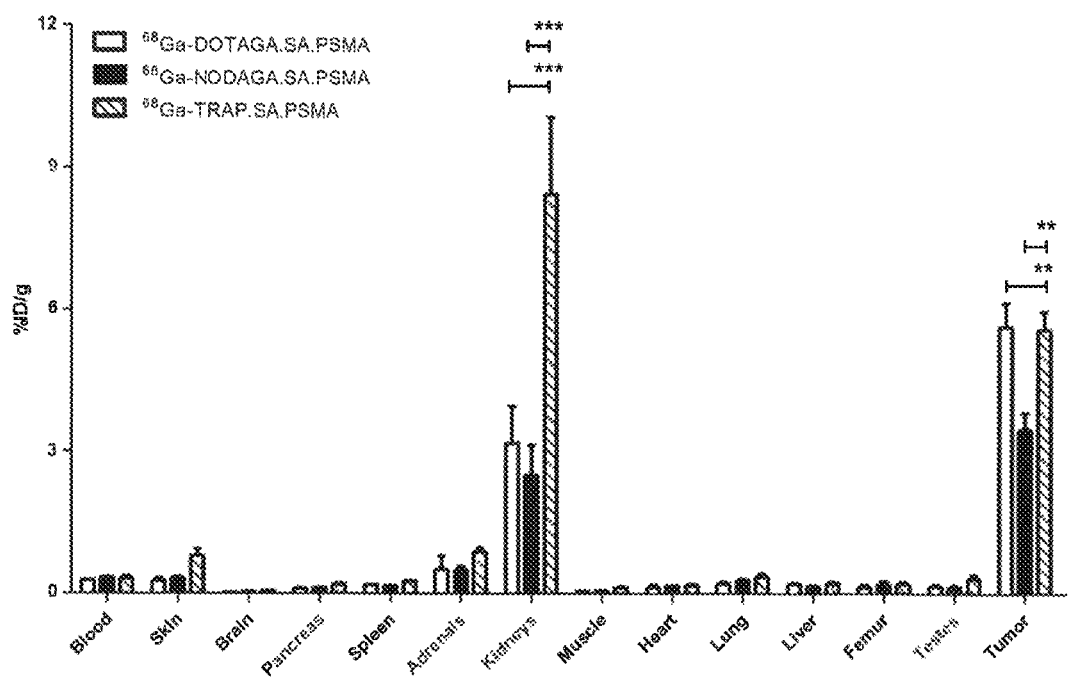
FIG. 30 graphically illustrates ex vivo results of three compounds each labeled with $^{68}$Ga.
Figure 31A:
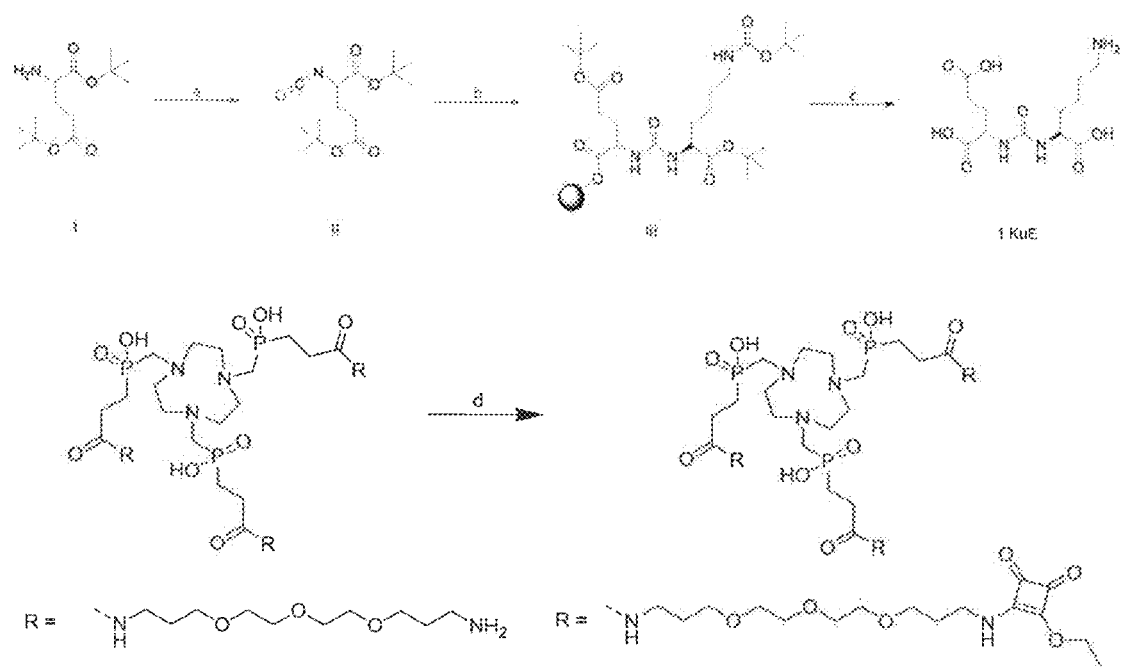
FIG. 31A illustrates the first portion of the synthesis schema of [$^{68}$Ga]Ga-TRAP.QS.PSMA where: a) is DIPEA, Triphosgene, DCM, 0° C., 4 h; b) is H-Lys(tBoc)-2CT-Polystyrol-solid phase, DCM, RT, 16 h; c) is TFA, RT, 71%; and d) is Dimethyl Squarate, Phosphate buffer (pH=7), RT, 24 h 85%.
Figure 31B:
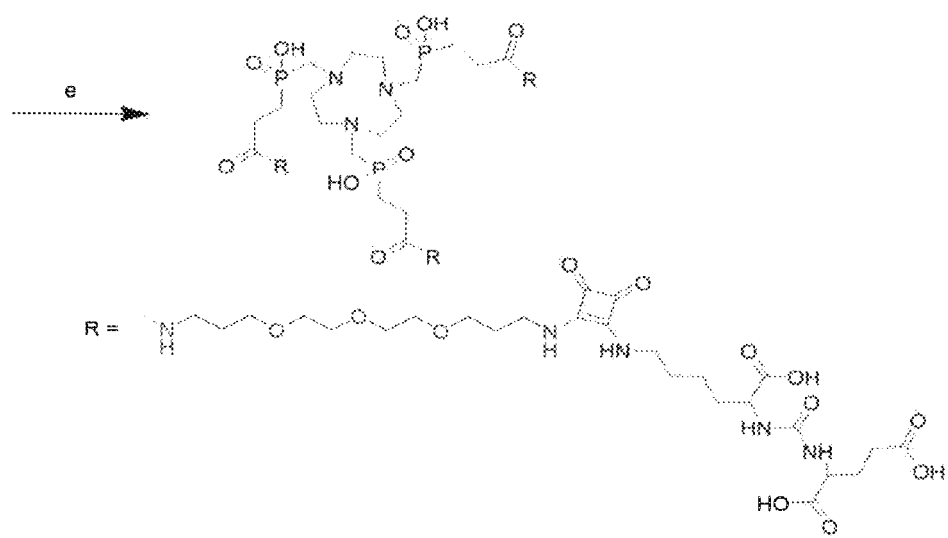
FIG. 31B illustrates the second portion of the synthesis schema of [$^{68}$Ga]Ga-TRAP.QS.PSMA where: e) is Phosphate buffer pH=9, RT, 24 h, 20%.
Figure 32:
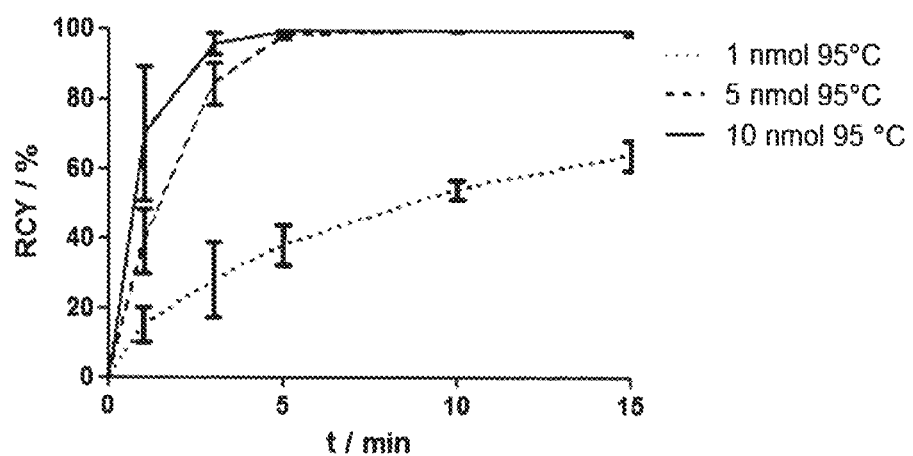
FIG. 32 graphically illustrates the radioactive labeling of compounds with [$^{68}$Ga]Ga-TRAP.QS.PSMA measured by radio-DC.
Figure 33:
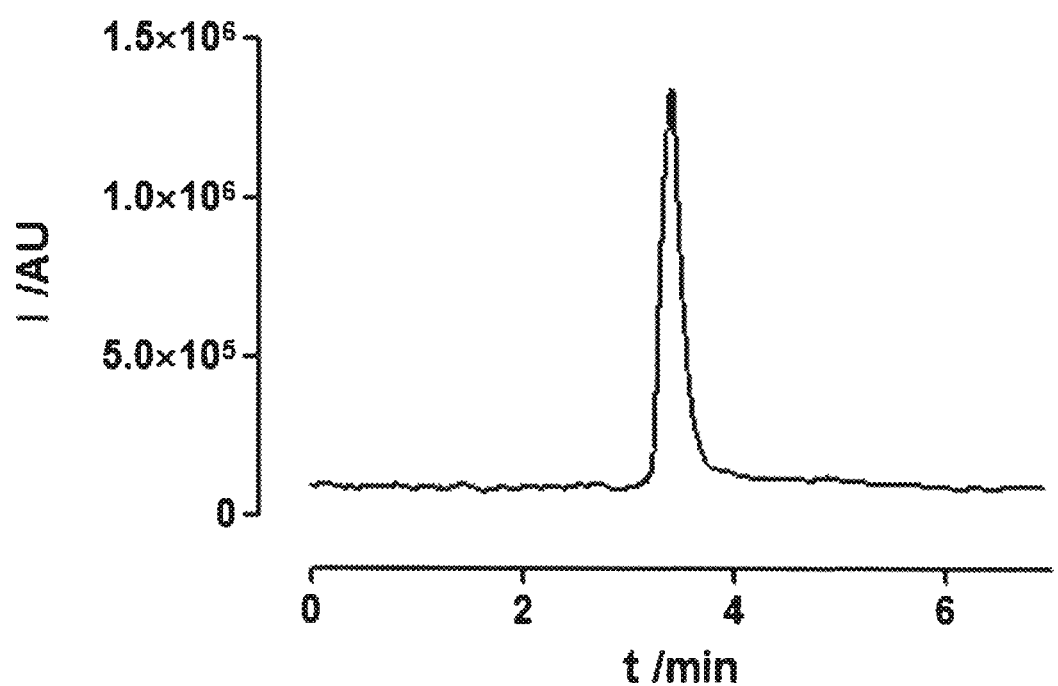
FIG. 33 graphically illustrate the radioactive labeling of compounds with [$^{68}$Ga]Ga-TRAP.QS.PSMA measured by radio-HPLC.
Figure 34:
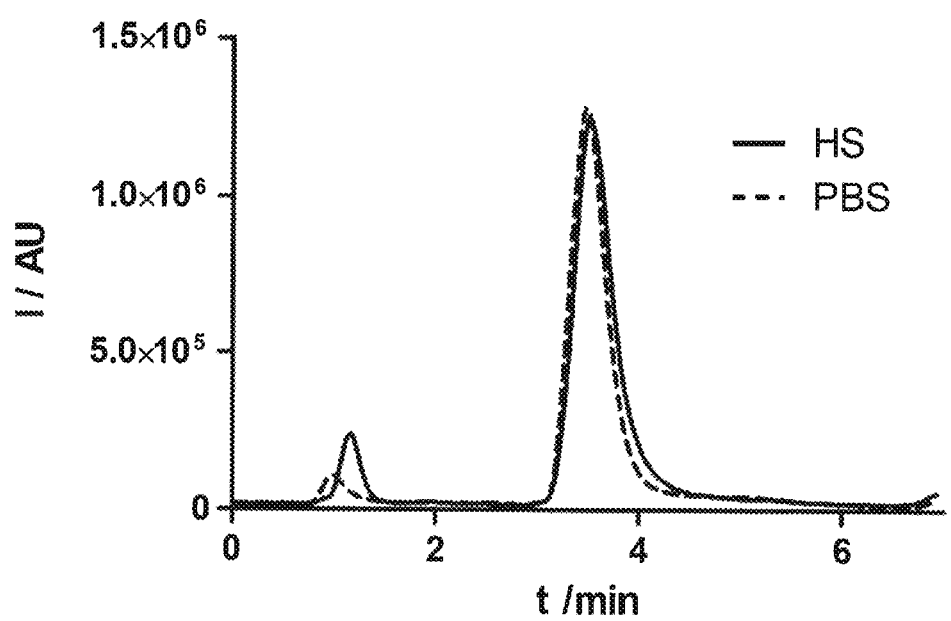
FIG. 34 graphically illustrates stability tests with [$^{68}$Ga]Ga-TRAP.QS.PSMA.
Figure 35:
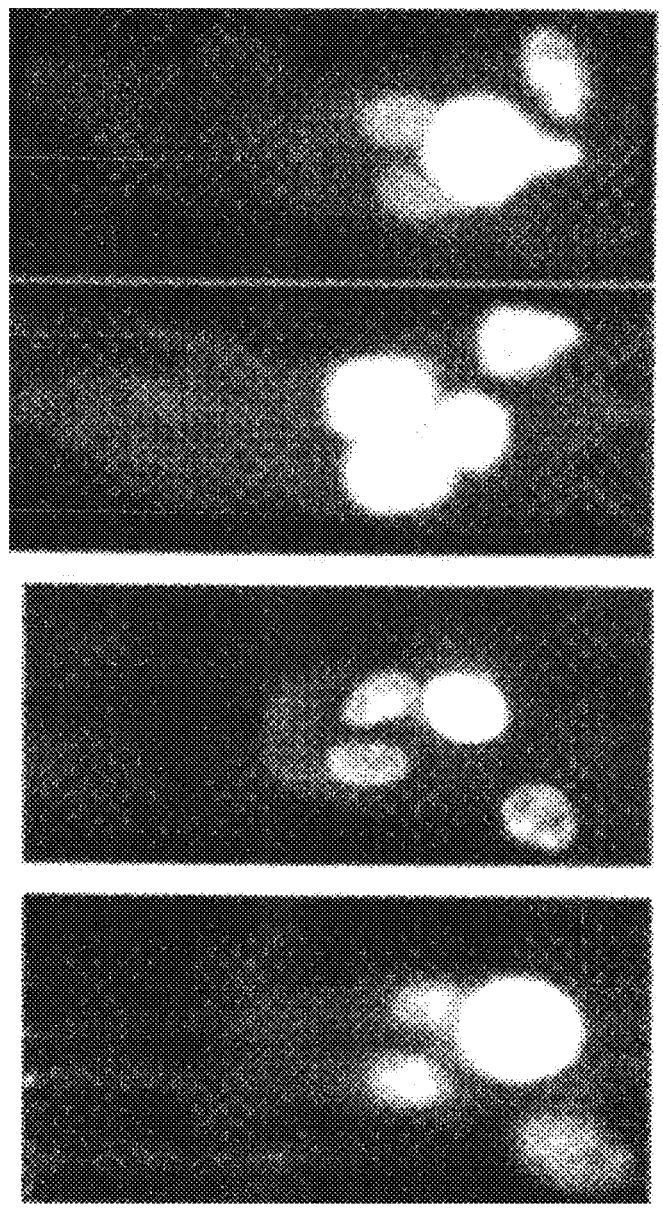
FIG. 35 reproduces images of in vivo investigation with [$^{68}$Ga]Ga-TRAP.QS.PSMA.
Figure 36:
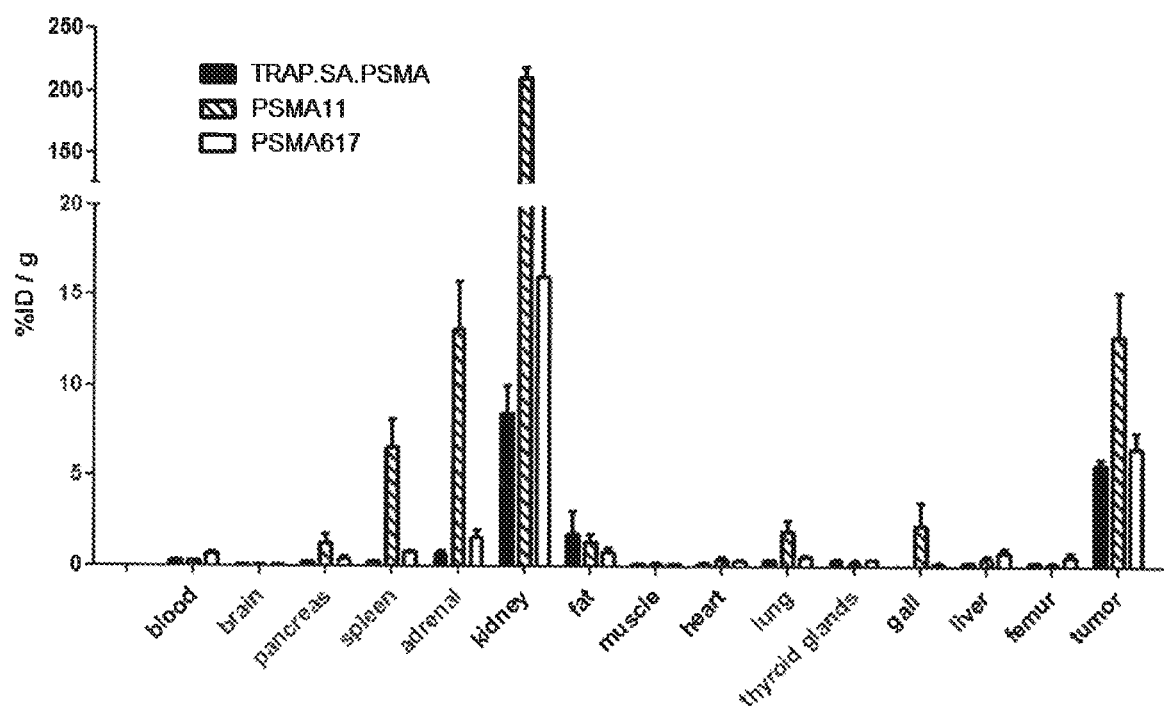
FIG. 36 graphically illustrates ex vivo results of [$^{68}$Ga]Ga-TRAP.QS.PSMA.

In addition, the three compounds DOTAGA.QS.PSMA, NODAGA.QS.PSMA and TRAP.QS.PSMA were investigated in vivo and ex vivo. FIG. 30 shows the ex vivo results of the three compounds each labeled with $^{68}$Ga. From FIG.

30 it can be seen that all three compounds accumulate in tumor tissue, with NODAGA.QS.PSMA showing low accumulation in the kidneys.

Example 11

TRAP.QS.PSMA

FIG. 31a-b, 32-36 show the synthesis and measurement results for radiolabeling, stability and in vivo investigations of the radiotracer [$^{68}$Ga]Ga-TRAP.QS.PSMA. The results are comparable to those of Examples 8 and 10. The in vivo studies were carried out with $^{68}$Ga and $^{64}$Cu. From the images it can be seen that, compared to Examples 8 and 10, the accumulation in the kidneys is increased for both radiotracers. This is due to the different lipophilicity of the radiotracers of Example 11 caused by long-chain linkers. The ex vivo comparison shows that compared to [$^{68}$Ga]Ga-PSMA-11 the accumulation in tumor tissue is elevated and noticeably decreased in the kidneys.

Example 12

[$^{68}$Ga]Ga-DATA OS.PSMA

Figure 37A:
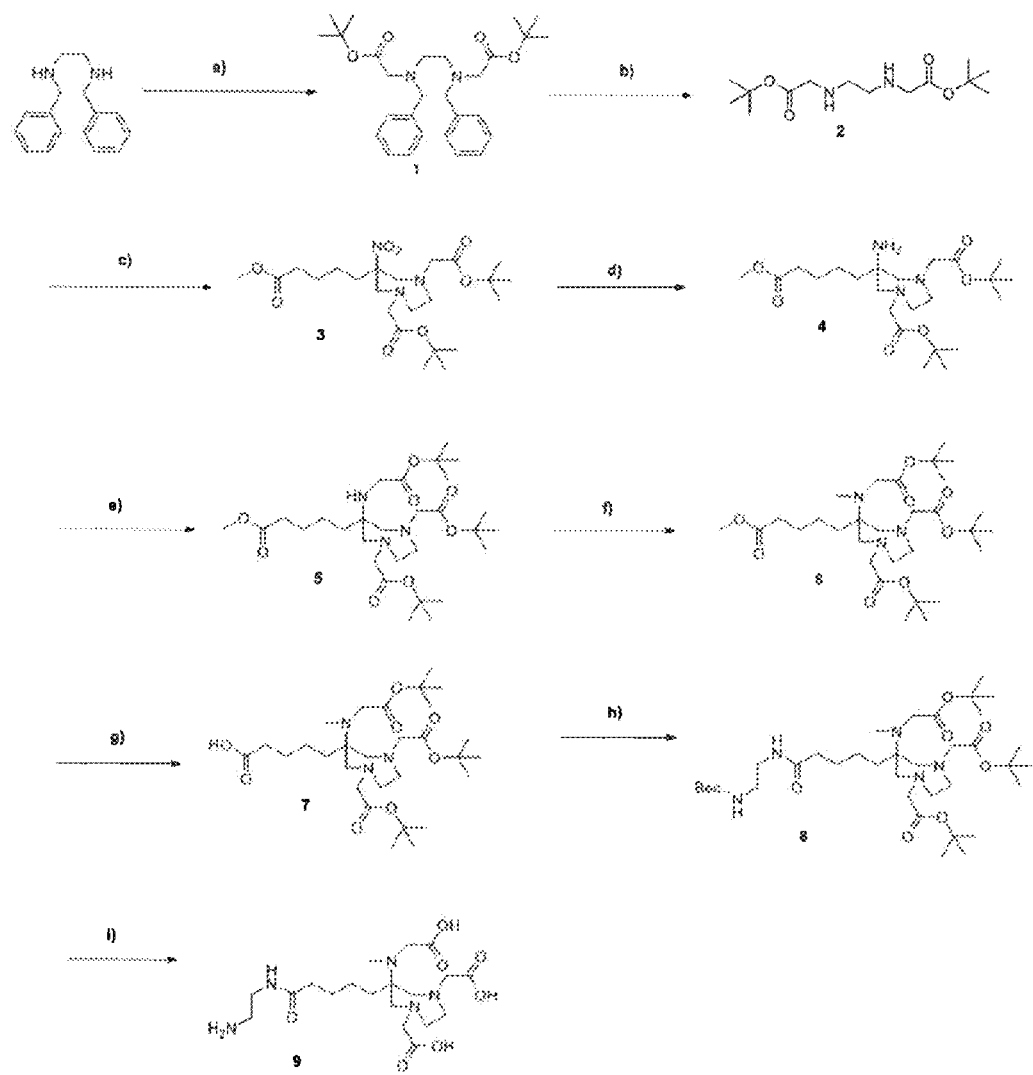
FIG. 37A is the first portion of a synthesis schema for a DATA.QS.PSMA compound.
Figure 37B:
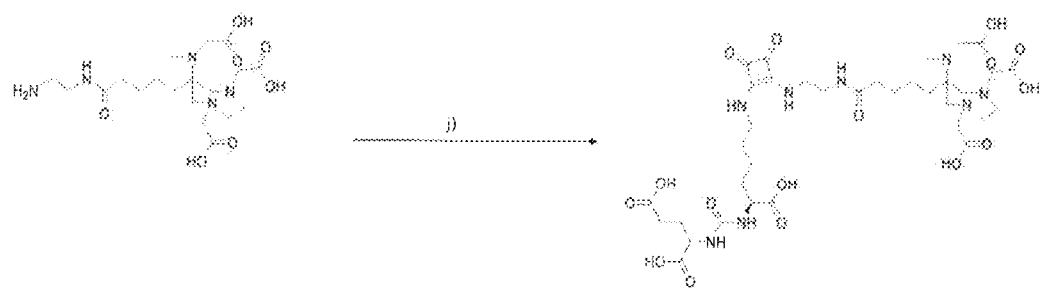
FIG. 37B is the second portion of a synthesis schema for a DATA.QS.PSMA compound.
Figure 38:
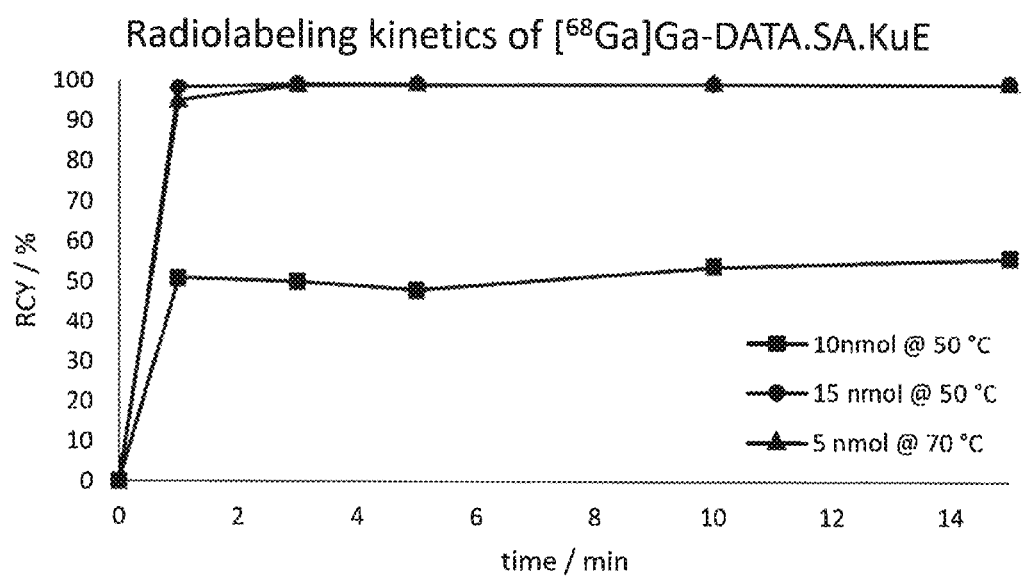
FIG. 38 is a graphical illustration of the radiolabeling kinetics of [$^{68}$Ga]Ga-DATA.SA.KuE.
Figure 39:
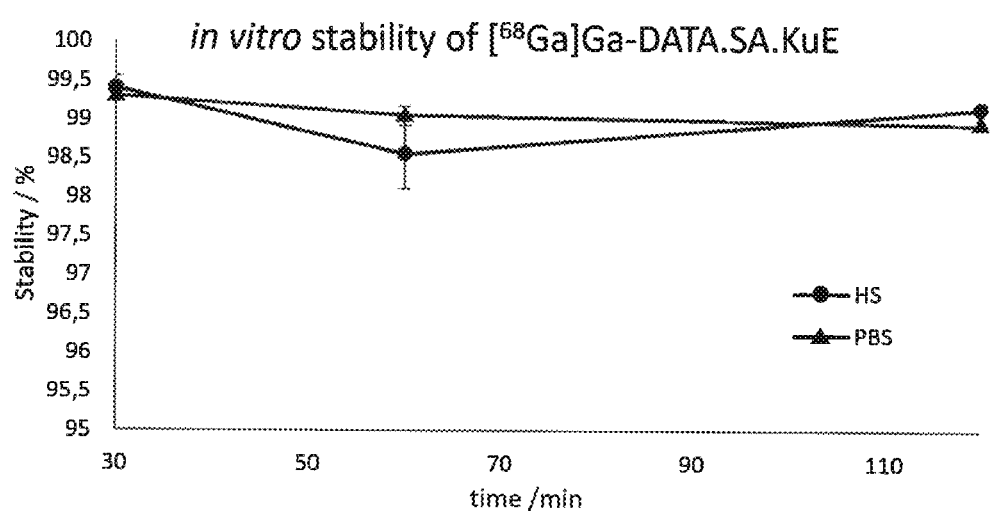
FIG. 39 is a graphical illustration of the in vitro stability of [$^{68}$Ga]Ga-DATA.SA.KuE.

Further compounds according to the invention are those of the DATA.QS.PSMA type, the structure of which corresponds to the other compounds listed, with the DATA chelator enabling simpler and milder labeling. In the synthesis shown in FIG. 37, a yield of about 70% is achieved. In the case of radioactive labeling with $^{68}$Ga, a yield of more than 95% is achieved (FIG. 38). As can be seen from FIG. 39, the compounds have high stability in both human serum (HS) and phosphate-buffered saline (PBS). In in vitro studies of the compound with LNCap cells, an IC$_{50}$ value of 51.5 nM is obtained, which is comparable to PSMA-11 and PSMA-617 (Table 3).

Figure 40:
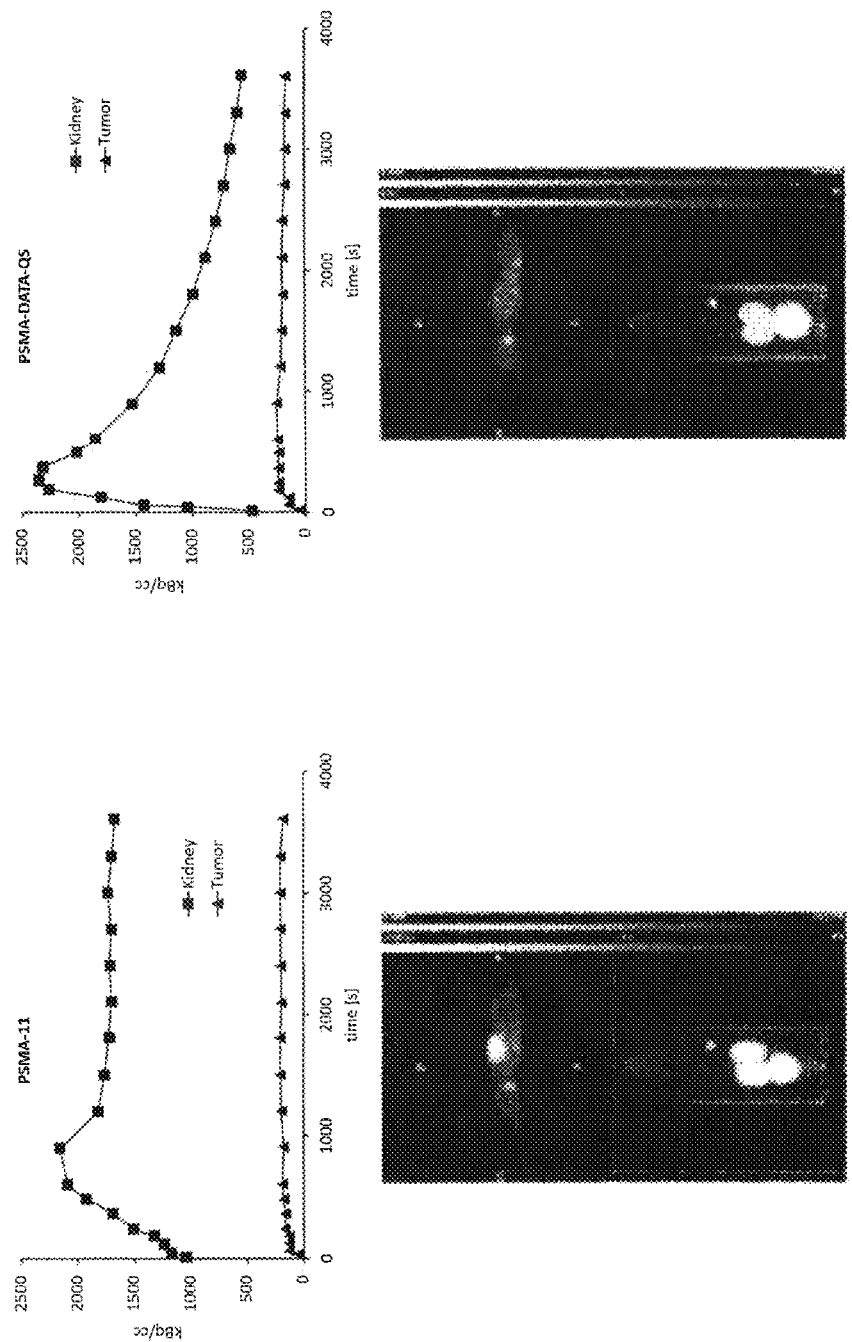
FIG. 40 reproduces MIP images of [$^{68}$Ga]Ga-DATA.QS.PSMA in the tumor and associated time/activity curves.

Furthermore, compounds of the type DATA.QS.PSMA were compared in vivo with PSMA-11 in the same animal model. The MIP images (FIG. 40) clearly show high accumulation of [$^{68}$Ga]Ga-DATA.QS.PSMA in the tumor. The time/activity curves depicted in FIG. 40 also show that for [$^{68}$Ga]Ga-DATA.QS.PSMA the excretion via the kidneys occurs significantly faster in the first hour than for [$^{68}$Ga]-PSMA-11. The accumulation in tumor tissue is comparable.

TABLE 3

| IC$_{50}$ values of the unlabeled compounds | |
| --- | --- |
| Compound | IC$_{50}$ [nM] |
| PSMA-11 | 26.1 ± 1.2 |
| PSMA-617 | 15.1 |
| DATA.QS.PSMA | 51.1 ± 5.5 |

Figure 41:
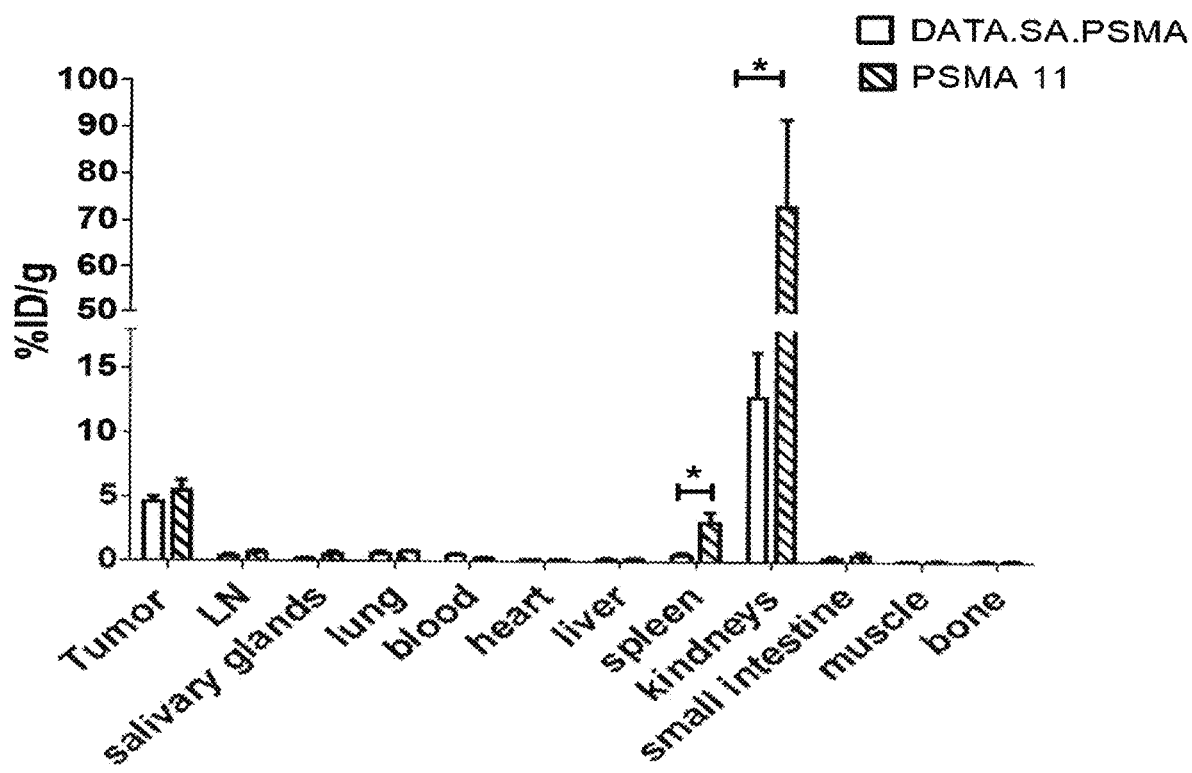
FIG. 41 is a graphical illustration of an ex vivo investigation.
Figure 42:
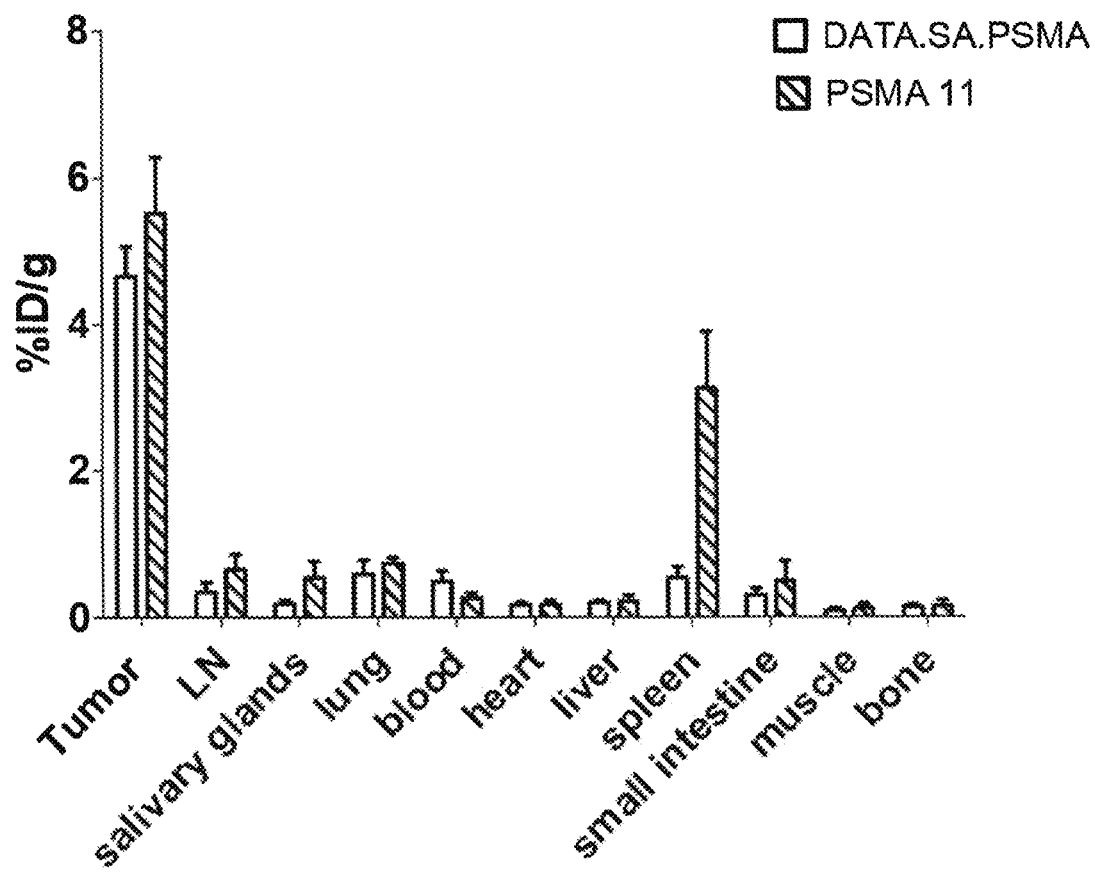
FIG. 42 is a graphical illustration of an ex vivo investigation.
Figure 43:
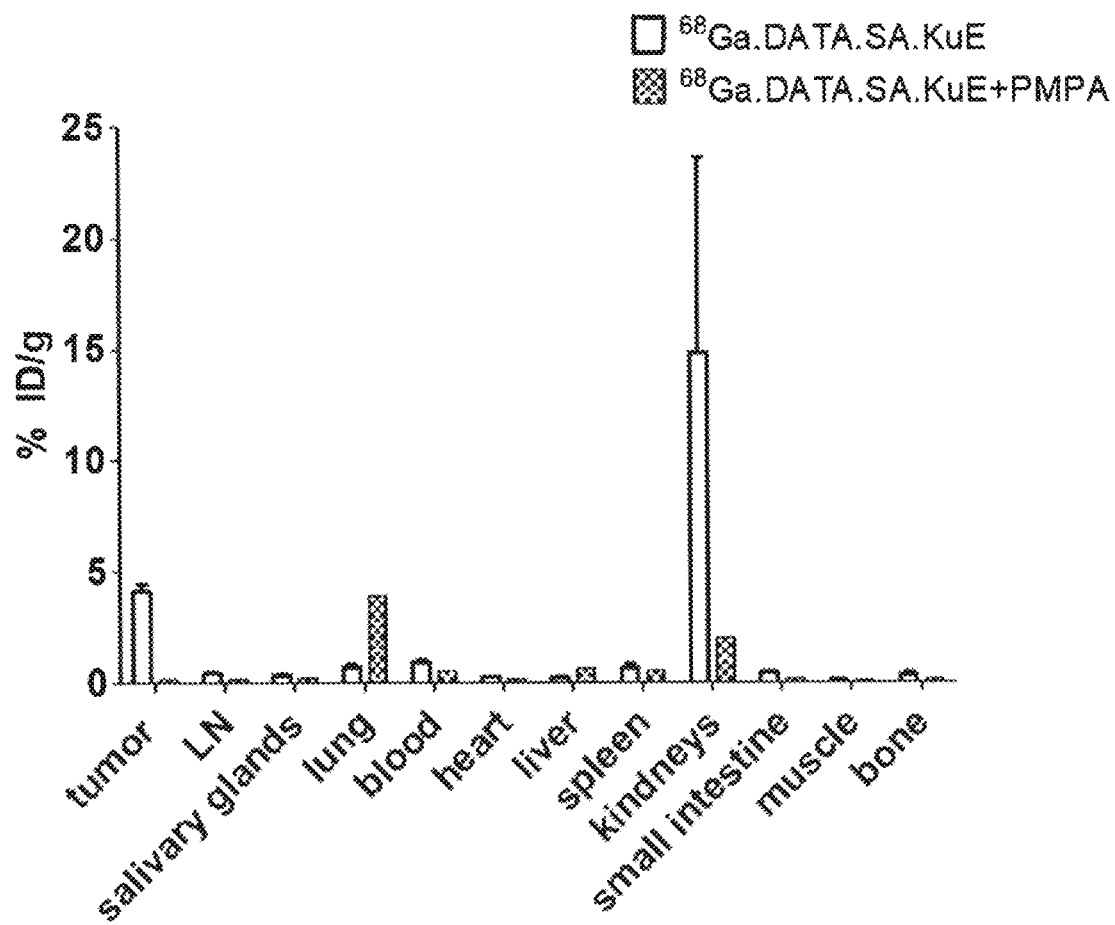
FIG. 43 is a graphical illustration of an ex vivo investigation.

The results of ex vivo investigations (FIGS. 41-43) are in agreement with the in vivo observations. As can be seen from Table 4, the % ID/g values of the two compounds labeled with $^{68}$Ga within the tumor are comparable, whereas for [$^{68}$Ga]Ga-DATA.QS.PSMA the accumulation in the kidneys and the salivary glands is considerably reduced. Low accumulation in the salivary glands is very advantageous since the latter are exposed to an elevated dose and their function is considerably impaired in known methods for radiopharmaceutical treatment of prostate cancer. Blocking studies with 2-PMPA also show that the inventive compounds have an increased specificity for PSMA.

TABLE 4

| Ex vivo activities | | |
| --- | --- | --- |
| | $^{68}$Ga.DATA.QS.PSMA | $^{68}$Ga.PSMA 11 |
| | % ID/g ± SD | |
| tumor | 4.65 ± 0.58 | 5.51 ± 0.38 |
| LN | 0.35 ± 0.20 | 0.66 ± 0.10 |
| salivary glands | 0.19 ± 0.07 | 0.54 ± 0.11 |
| lung | 0.59 ± 0.27 | 0.74 ± 0.04 |
| blood | 0.50 ± 0.19 | 0.27 ± 0.03 |
| heart | 0.17 ± 0.06 | 0.17 ± 0.03 |
| liver | 0.21 ± 0.04 | 0.23 ± 0.04 |
| spleen | 0.54 ± 0.22 | 3.12 ± 0.39 |
| kidney left | 6.59 ± 2.45 | 36.66 ± 5.05 |
| kidney right | 6.23 ± 2.39 | 36.72 ± 4.33 |
| small intestine | 0.31 ± 0.12 | 0.50 ± 0.14 |
| muscle | 0.09 ± 0.05 | 0.11 ± 0.03 |
| bone | 0.15 ± 0.03 | 0.15 ± 0.04 |

Example 13

[$^{44}$Sc]Sc-AAZTA.QS.PSMA

Figure 44:
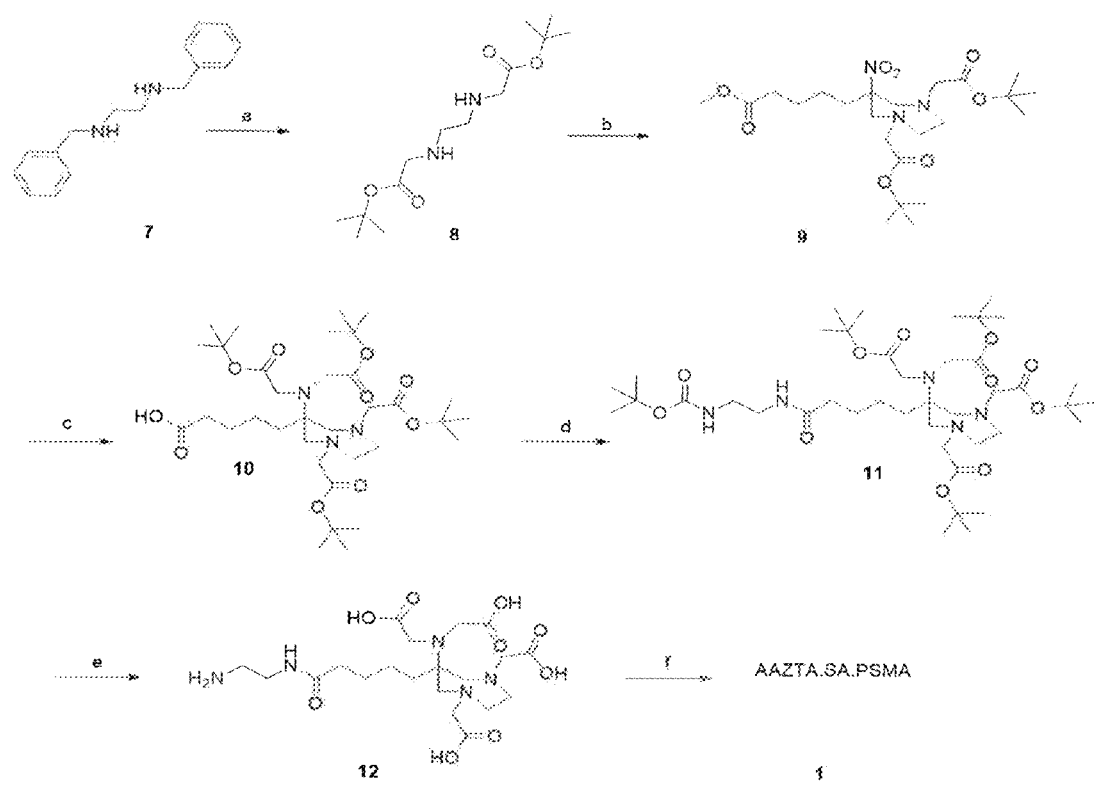
FIG. 44 is the synthesis schema of an AAZTA.SA.PSMA compound.
Figure 45:
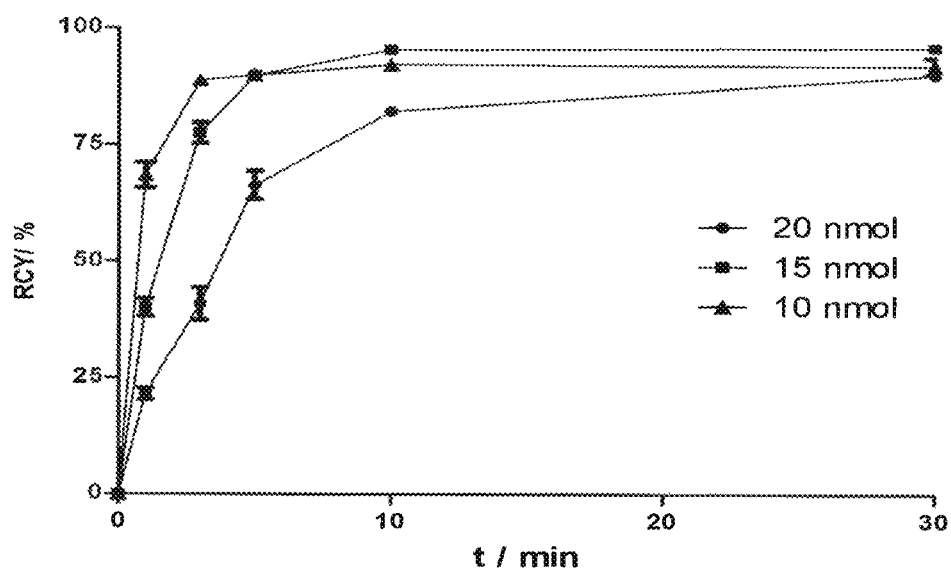
FIG. 45 is a graphical illustration of the radiolabeling kinetics of a [$^{44}$Sc]Sc-AAZTA.QS.PSMA compound.
Figure 46:
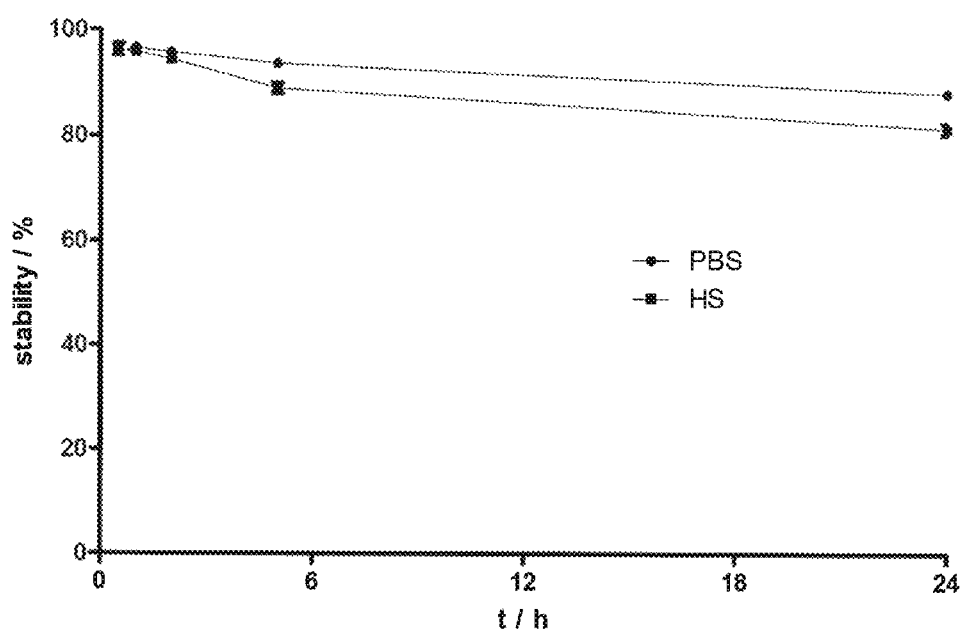
FIG. 46 is a graphical illustration of the stability of [$^{44}$Sc]Sc-AAZTA.QS.PSMA compound.

Similar to DATA, the AAZTA chelator can also be labeled with radio nuclides such as $^{44}$Sc and $^{68}$Ga under mild conditions. In the instant example, the radioisotope $^{44}$Sc is used and the properties of the radiotracer [$^{44}$Sc]Sc-AAZTA.QS.PSMA are investigated. The synthesis shown in FIG. 44 was readily carried out with high yield. As shown in FIG. 45, a high yield is also obtained for radiolabeling. The stability of [$^{44}$Sc]Sc-AAZTA.QS.PSMA exceeds 95% over a period of 24 hours (FIG. 46).

Figure 47:
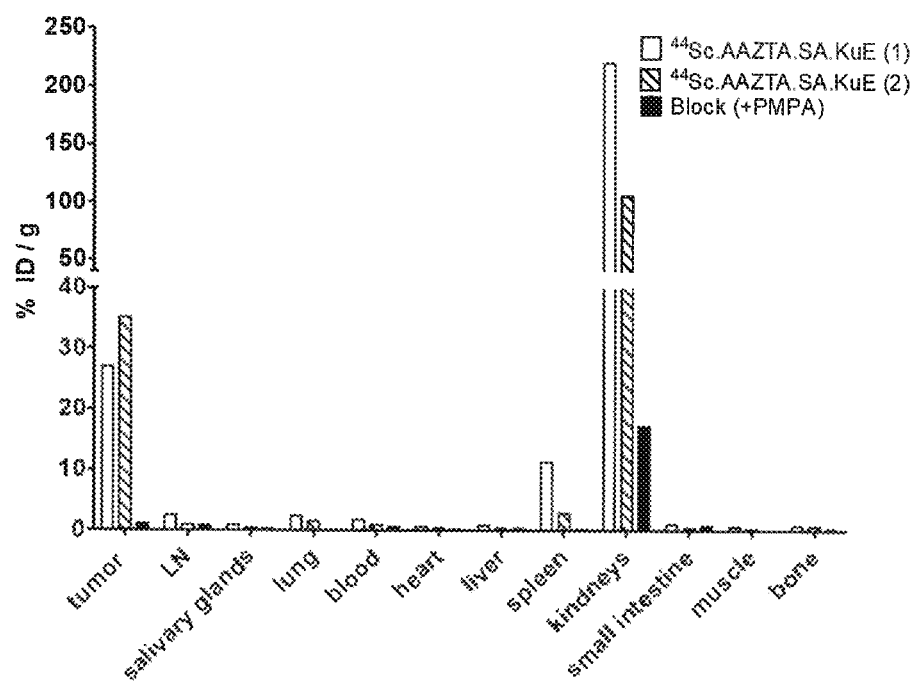
FIG. 47 is a graphical illustration of an ex vivo investigation of [$^{44}$Sc]Sc-AAZTA.SA.KuE compounds.
Figure 48:
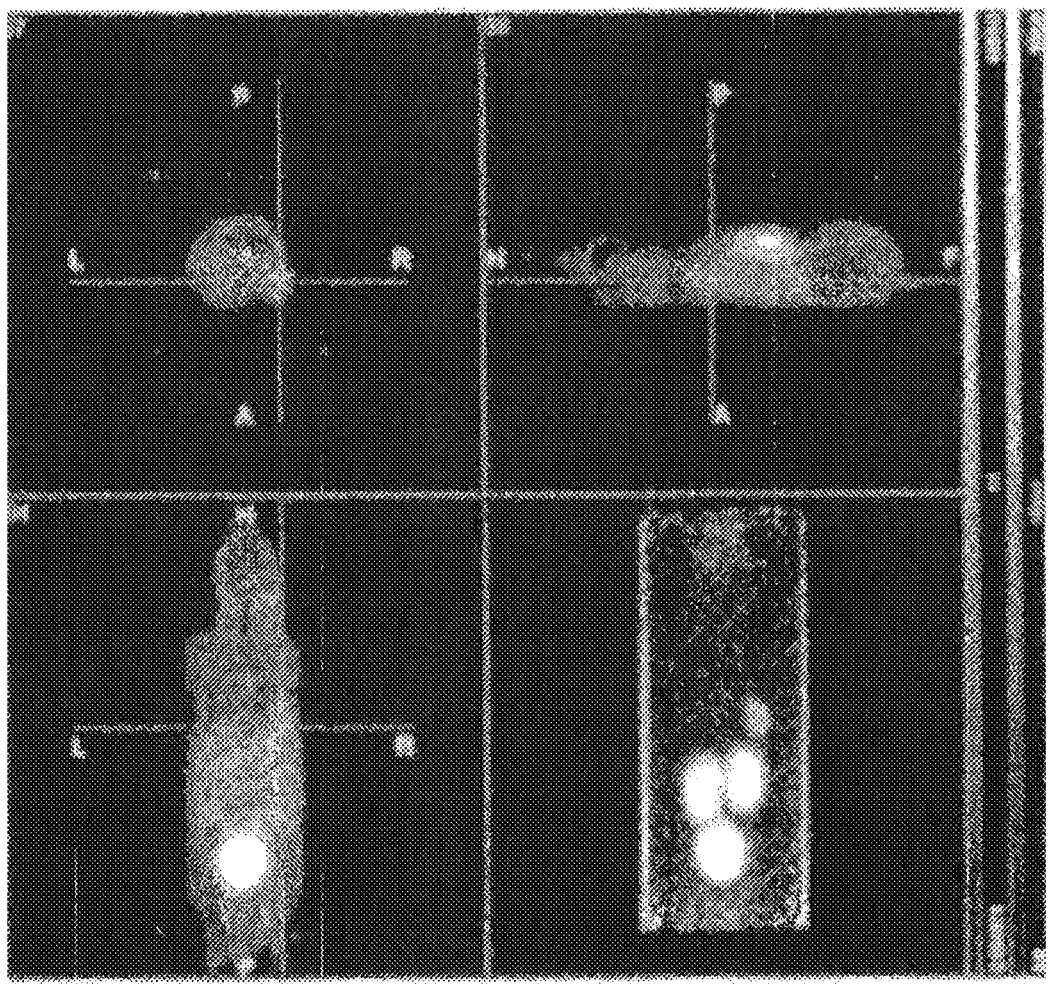
FIG. 48 reproduces images of in vivo investigation with [$^{44}$Sc]Sc-AAZTA.QS.PSMA.
Figure 49:
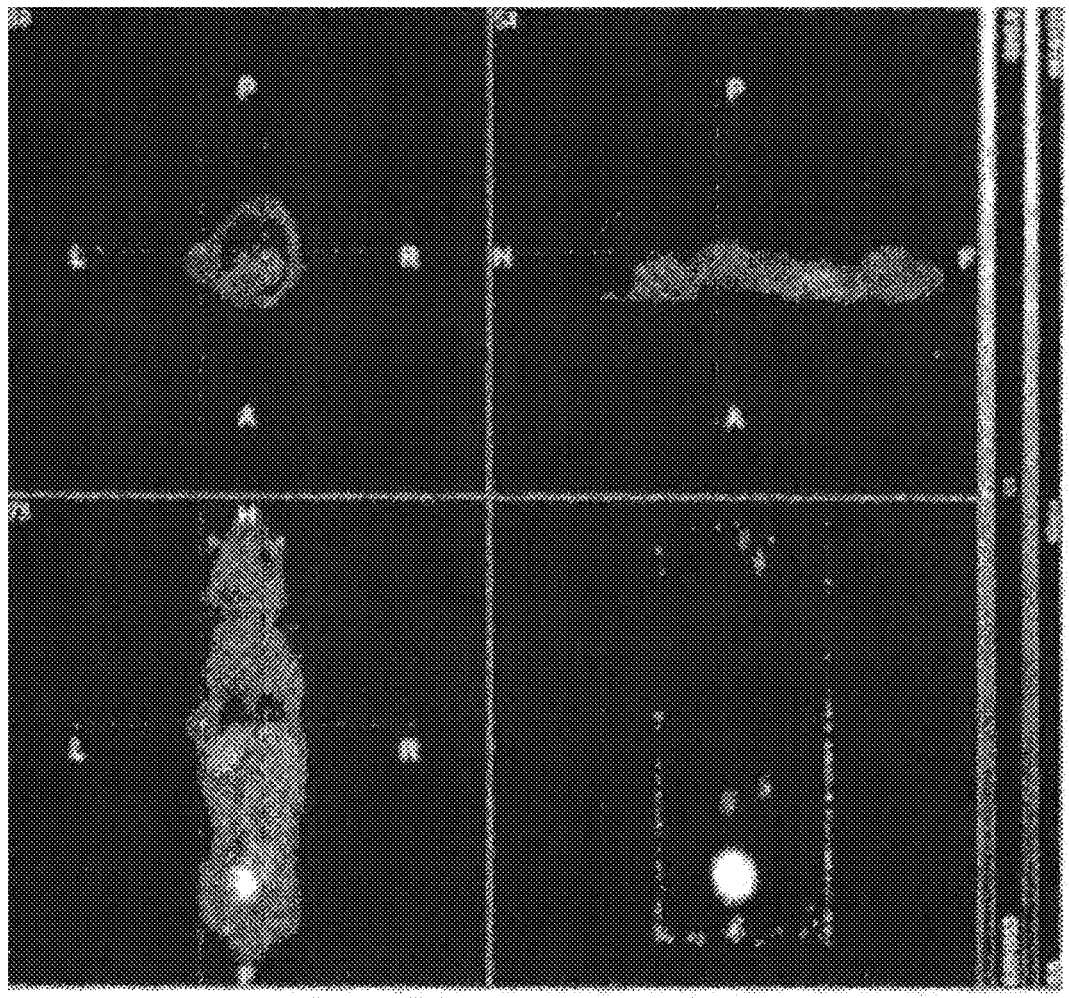
FIG. 49 reproduces images of an in vivo investigation with [$^{44}$Sc]Sc-AAZTA.QS.PSMA.

The radiotracer [$^{44}$Sc]Sc-AAZTA.QS.PSMA was further examined in vivo in three mice, each carrying an LNCap tumor. In addition blocking tests were carried out on one of the mice. The ex vivo results shown in Table 5 and FIG. 47 show that the AAZTA derivatives labeled with $^{44}$Sc are also highly accumulated within the tumor tissue. Furthermore, a large part of the activity in the tumor can be blocked with 2-PMPA. The same applies to the kidneys. These results are in agreement with corresponding in vivo studies. FIGS. 48 and 49 show the tumor activity 1 h after injection without blocking and 40 after injection (20 min static recording) with blocking by co-injection of 2-PMPA.

TABLE 5

| Ex vivo activities | | | |
| --- | --- | --- | --- |
| % ID/g | | | |
| | $^{44}$Sc.AAZTA.QS.KuE (1) | $^{44}$Sc.AAZTA.QS.KuE (2) | Block (+PMPA) |
| tumor | 14.73 | 14.14 | 0.53 |
| LN | 1.33 | 0.38 | 0.39 |
| salivary glands | 0.51 | 0.18 | 0.11 |
| lung | 1.31 | 0.59 | 0.06 |

TABLE 5-continued

| | Ex vivo activities | | |
|---|---|---|---|
| | % ID/g | | |
| | $^{44}$Sc.AAZTA.QS.KuE (1) | $^{44}$Sc.AAZTA.QS.KuE (2) | Block (+PMPA) |
| blood | 0.96 | 0.41 | 0.34 |
| heart | 0.41 | 0.14 | 0.11 |
| liver | 0.42 | 0.16 | 0.16 |
| spleen | 6.19 | 1.15 | 0.15 |
| kindneys | 119.86 | 42.76 | 7.97 |
| small intestine | 0.62 | 0.22 | 0.35 |
| muscle | 0.38 | 0.13 | 0.05 |
| bone | 0.46 | 0.29 | 0.10 |

Example 14

Compounds for $^{18}$F Labeling

For PET diagnosis with $^{18}$F, various labeling precursors were synthesized and examined in vitro in LNCap cells. For several of the examined compounds, low IC$_{50}$ values corresponding to PSMA-11 and PSMA-617 were observed. Three such compounds and their IC$_{50}$ values are shown in FIG. 50.

Figure 50:
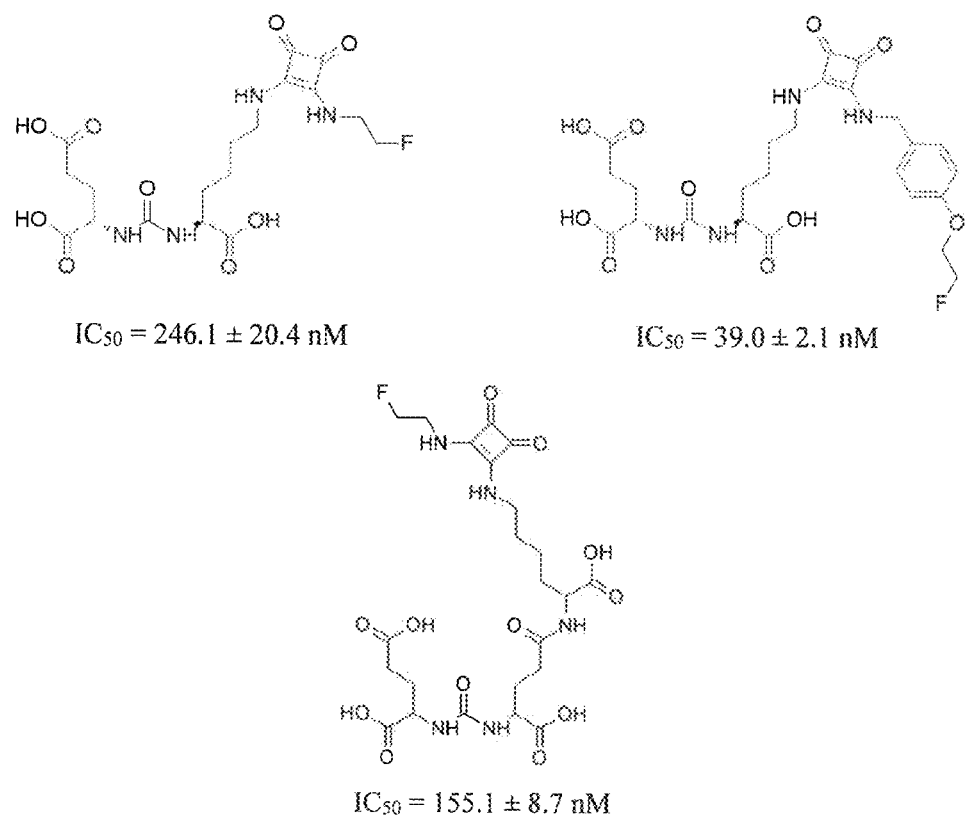
FIG. 50 illustrates chemical structures of compounds for $^{18}$F-radiotracers.

(FIG. 50: Compounds for $^{18}$F Radiotracers)

Example 15

DOTA.FAPi and DATA.FAPi

Figure 51:
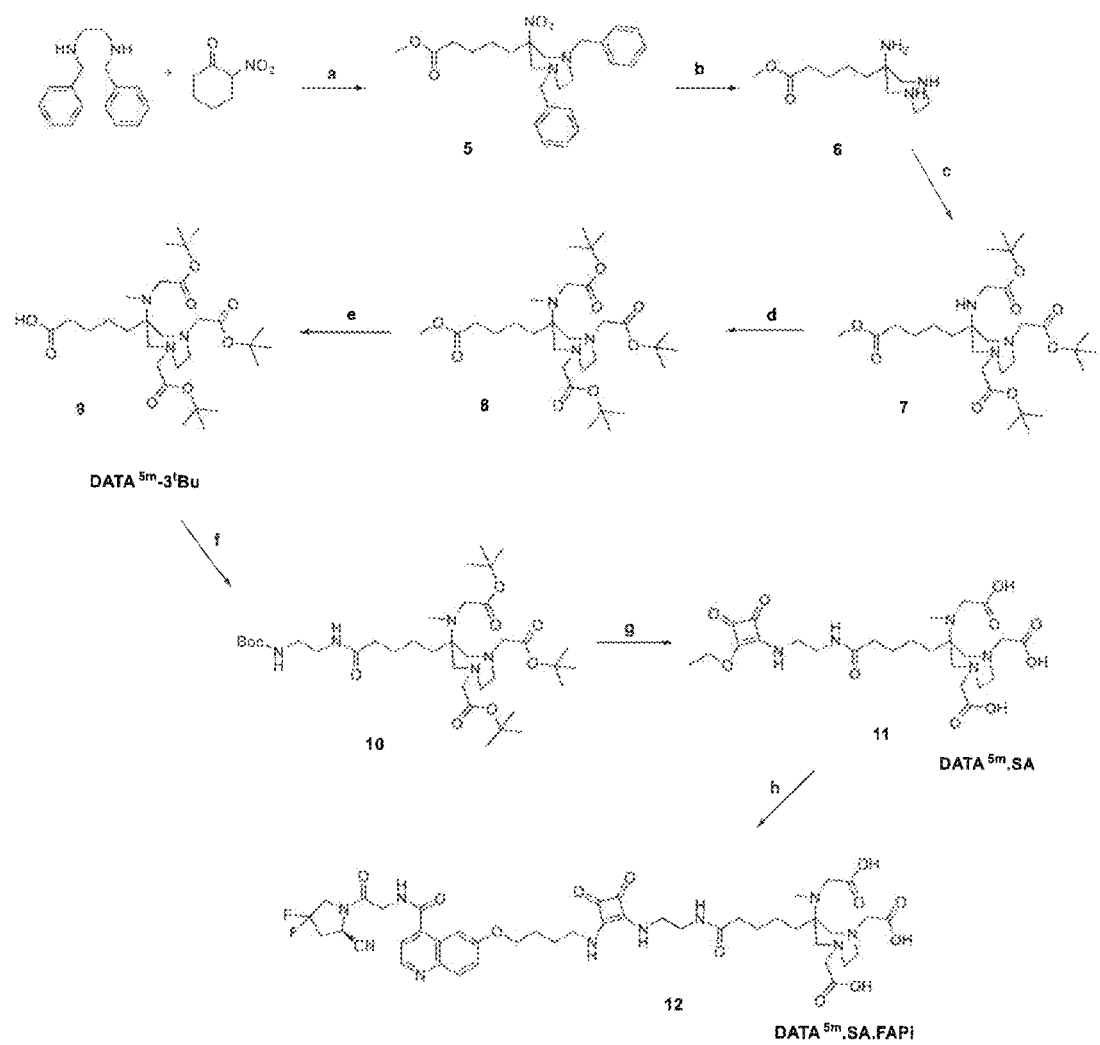
FIG. 51 illustrates a reaction synthesis of DATA$^{5m}$.SA.FAPi.

The synthesis of DOTA.QS.FAPi shown in FIG. 51 is carried out analogously to Example 6 and comprises the steps: (a) Paraformaldehyde, MeOH, Amberlyst A21; (b) Pd/C, CH$_3$COOH, abs. EtOH, K$_2$CO$_3$; (c) tert-butyl bromoacetate, MeCN, K$_2$CO$_3$; (d) formalin (37 wt %), CH$_3$COOH, NaBH$_4$, MeCN; (e) 1 M LiOH, 1,4-dioxane/H$_2$O (2:1); (f) N-boc-Ethylenediamine, HATU, HOBt, DIPEA, MeCN; (g) (i) 80% TFA in DCM, (ii) 3,4-diethoxycyclobut-3-ene-1,2-dione, phosphate buffer pH 7, 1 M NaOH; (h) 3, phosphate buffer pH 9, 1 M NaOH.

(FIG. 51: Synthesis DATA.QS.FAPi)

Figure 52:
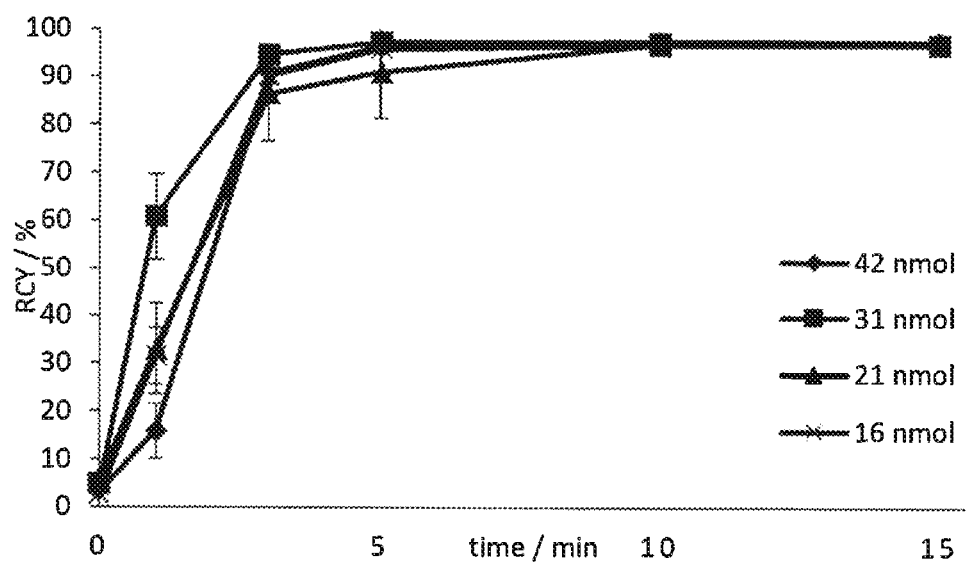
FIG. 52 is a graphical illustration of [$^{68}$Ga]Ga-DOTA.SA.FAPi labeling efficacy.
Figure 53:
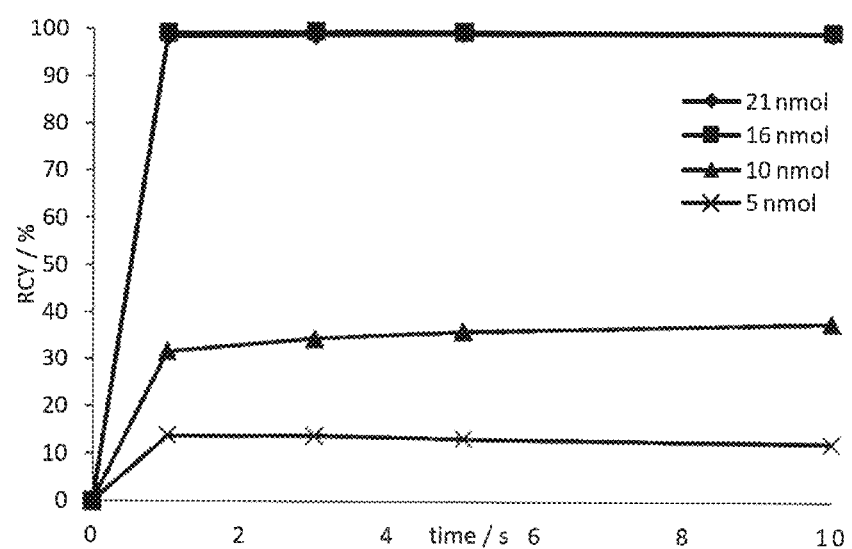
FIG. 53 is a graphical illustration of the radiolabeling kinetics [$^{68}$Ga]Ga-DOTA.SA.FAPi.

Labeling with $^{68}$Ga occurs rapidly and in high yield (FIGS. 52 and 53). The stability in human serum (HS) and NaCl solution is more than 98% over a period of 2 hours (Table 6).

TABLE 6

| Stability in HS, EtOH and NaCl | | | |
|---|---|---|---|
| | Medium | | |
| time/min | HS | EtOH | 0.9% NaCl |
| 15 | 99.7 ± 0.3 | 99.6 ± 0.1 | 99.6 ± 0.2 |
| 30 | 99.8 ± 0.1 | 99.9 ± 0.1 | 99.9 ± 0.0 |
| 45 | 99.6 ± 0.4 | 99.9 ± 0.1 | 99.9 ± 0.1 |
| 60 | 99.2 ± 0.2 | 99.6 ± 0.2 | 99.6 ± 0.2 |
| 90 | 98.3 ± 0.2 | 99.6 ± 0.1 | 99.3 ± 0.1 |
| 120 | 98.8 ± 0.6 | 100.0 ± 0.1 | 99.4 ± 0.3 |

The FAP IC$_{50}$ values were measured using Z-Gly-Pro-7-amino-4-methylcoumarin (AMC). The PREP IC$_{50}$ values were determined using N-succinyl-Gly-Pro-AMC. The selectivity indices are comparable with literature values (Jansen et al. J Med Chem, 2014, 7, 3053). The measured values are shown in Table 7.

TABLE 7

| IC$_{50}$ values and selectivity indices | | | |
|---|---|---|---|
| | IC$_{50}$ FAP (nM)* | IC$_{50}$ PREP (µM) | Selectivity index (FAP/PREP) |
| DOTA.QS.FAPi - uncomplexed | 0.9 ± 0.1 | 5.4 ± 0.3 | 6000 |
| DOTA.QS.FAPi - natGa | 1.4 ± 0.2 | 8.7 ± 0.9 | 6214 |
| DOTA.QS.FAPi - natLu | 0.8 ± 0.2 | 2.5 ± 0.4 | 3125 |
| DATA$^{5m}$.QS.FAPi - uncomplexed | 0.8 ± 0.2 | 1.69 ± 0.09 | 2113 |
| DATA5m.QS.FAPi - natGa | 0.7 ± 0.1 | 4.7 ± 0.3 | 6714 |

Figure 54:
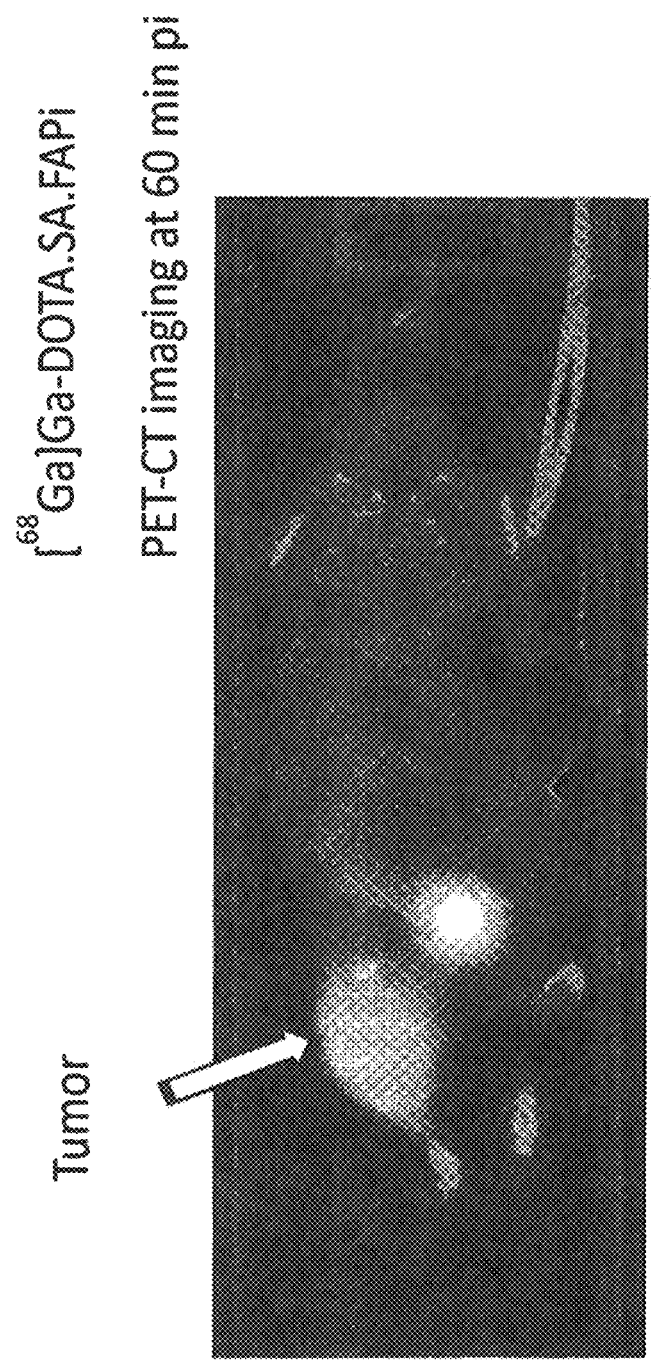
FIG. 54 reproduces an image of in vivo investigation with [$^{68}$Ga]Ga-DOTA.SA.FAPi.
Figure 55:
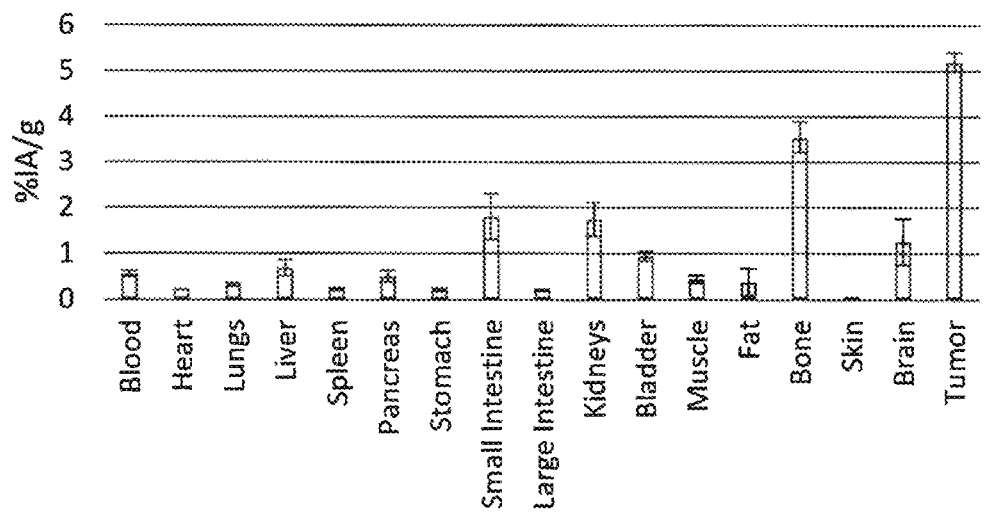
FIG. 55 graphically illustrates the ex vivo results of [$^{68}$Ga]Ga-DOTA.SA.FAPi.

In vivo as well as ex vivo examinations with [$^{68}$Ga]Ga-DOTA.QS.FAPi in mice bearing colon cancer (HT29) show a high concentration in the tumor tissue (FIGS. 54 and 55).

That which is claimed:

1. A labeling precursor for a radiopharmaceutical whose structure (A) comprises:

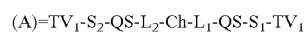
(A)=TV$_1$-S$_2$-QS-L$_2$-Ch-L$_1$-QS-S$_1$-TV$_1$ wherein Ch is a chelator, TV$_1$ is a targeting vector, QS is a squaric acid residue, L$_1$ and L$_2$ are linkers, and S$_1$ and S$_2$ are spacers;

the chelator is formed from a compound of formula (B);

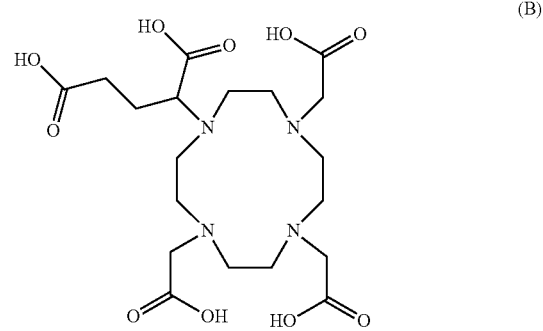 [SMILES: O=C(O)CCC(C(=O)O)N1CCN(CC(=O)O)CCN(CC(=O)O)CCN(CC(=O)O)CC1]

the targeting vector is a fibroblast activation protein inhibitor (FAPi);

QS is a squaric acid residue;

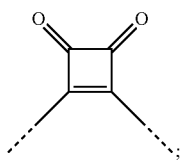

$L_1$ forms an amide residue;

$L_2$ is —$(CH_2)_m$NH— with m=1 through 10; and $S_1$ and $S_2$ are independently selected from —$(CH_2)_n$NH— with n=3 through 10.

2. The labeling precursor according to claim 1, wherein $S_1$ and $S_2$ are both —$(CH_2)_n$NH— with n=4.

3. The labeling precursor according to claim 1, wherein $L_1$ is —NH $(CH_2)_m$ NH with m=2 and $L_2$ is —$(CH_2)_m$NH with m=2.

4. The labeling precursor according to claim 1, wherein the chelator has been modified to form a compound of formula (C):

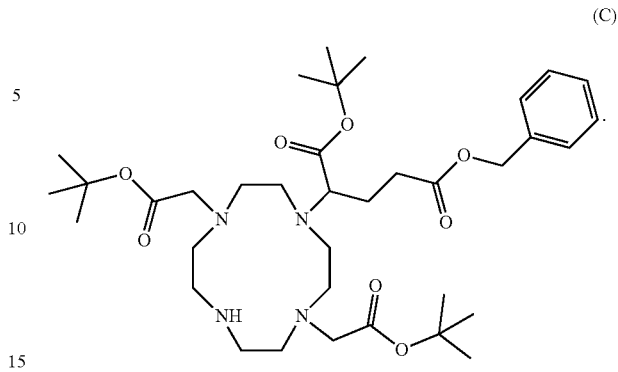

5. The labeling precursor according to claim 1, wherein the FAPi is a residue of the compound (D):

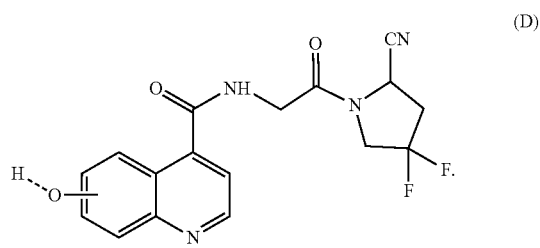

6. The labeling precursor according to claim 1, wherein the squaric acid residue is a squaric acid diester residue.

7. The labeling precursor according to claim 1, wherein the labeling precursor is a compound of the formula (E):

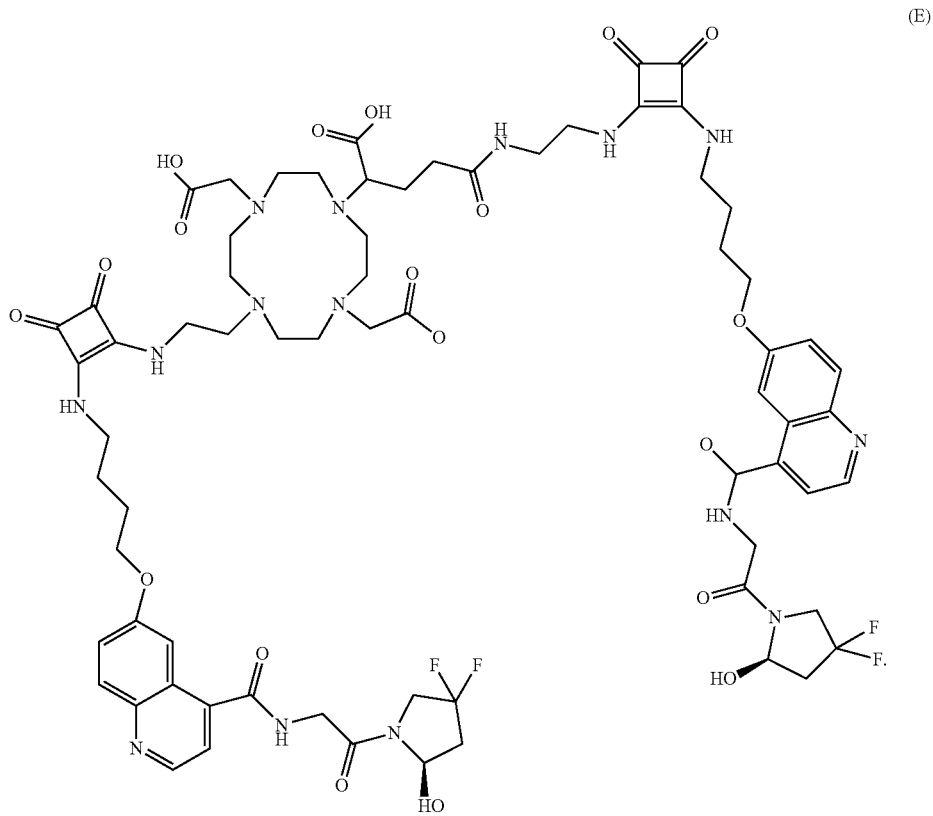 [SMILES: O=C(O)CN1CCN(CCNc2c(NCCCCOc3ccc4nccc(C(=O)NCC(=O)N5CC(F)(F)C[C@H]5O)c4c3)c(=O)c2=O)CCN(CC(=O)O)CCN(C(CCC(=O)NCCNc2c(NCCCCOc3ccc4nccc(C(O)NCC(=O)N5CC(F)(F)C[C@H]5O)c4c3)c(=O)c2=O)C(=O)O)CC1]

8. The labeling precursor according to claim 7, wherein the precursor further comprises a radioactive isotope.

9. The labeling precursor according to claim 8, wherein the radioactive isotope is selected from $^{44}$Sc, $^{47}$Sc, $^{55}$Co, $^{62}$Cu, $^{64}$Cu, $^{67}$Cu, $^{66}$Ga, $^{67}$Ga, $^{68}$Ga, $^{89}$Zr, $^{86}$Y, $^{90}$Y, $^{90}$Nb, $^{99m}$Tc, $^{111}$In, $^{135}$Sm, $^{140}$Pr, $^{159}$Gd, $^{149}$Tb, $^{160}$Tb, $^{161}$Tb, $^{165}$Er, $^{166}$Dy, $^{166}$Ho, $^{175}$Yb, $^{177}$Lu, $^{186}$Re, $^{188}$Re, $^{213}$Bi and $^{225}$Ac.

10. The labeling precursor according to claim 8, wherein the radioactive isotope is $^{68}$Ga or $^{177}$Lu.

11. A method for preparing a labeling precursor for a radiopharmaceutical comprising the steps of (a) providing a compound of formula (I):

(I)

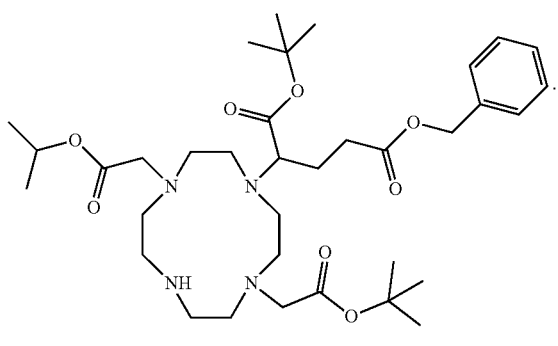

(b) adding a first linking group to the compound of formula (I) by reacting the compound of formula (I) with a compound of formula (II):

(II)

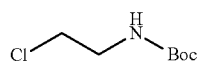

(c) deprotecting the pentane dioic acid group of the compound formed in step (b) to form a compound of formula (III):

(III)

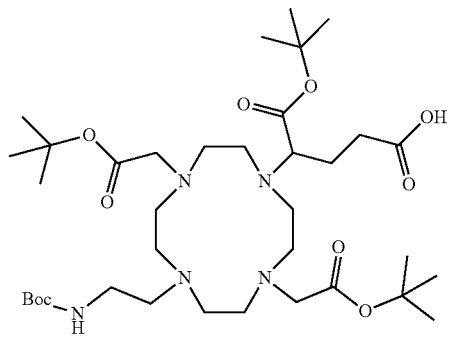

(d) adding a second linking group to the deprotected compound of formula (III) by reacting the deprotected compound of formula (III) with ethylenediamine to form a bi-linked compound of formula (IV):

(IV)

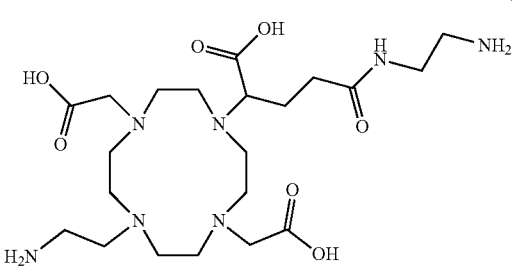

(e) deprotecting the bi-linked compound of formula (IV) to form the bi-linked chelator of formula (V):

(V)

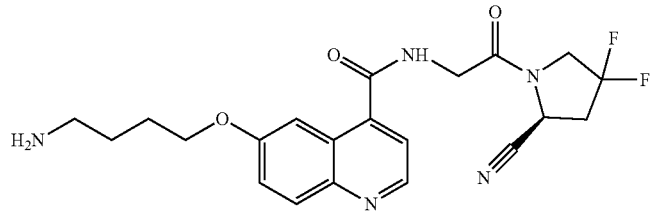

(f) reacting a butyl amine spaced targeting vector of the formula (VI) with squaric acid to form a compound of the formula (VII):

(VI)

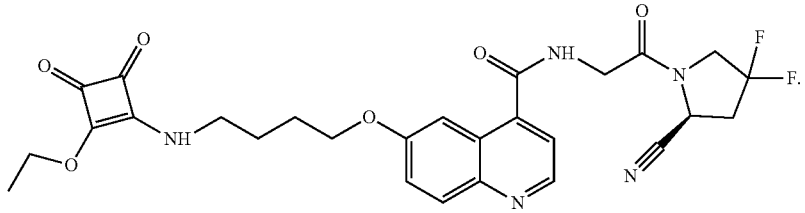

(g) reacting the squaric acid-modified targeting vector of formula (VII) with the bi-linked chelator of formula (V) to form the labeling precursor of formula (E):

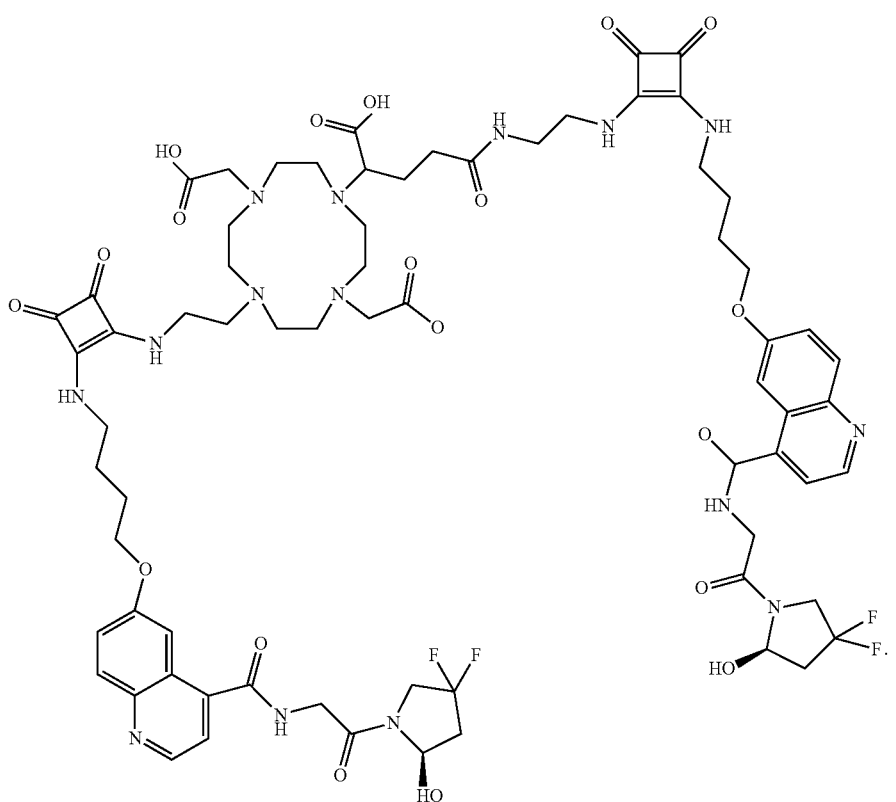

12. A method of diagnosing and/or treating cancer comprising administering a radiopharmaceutical comprising a radioactive isotope and a compound of formula (E) to diagnose and/or treat cancer expressing FAP (I)

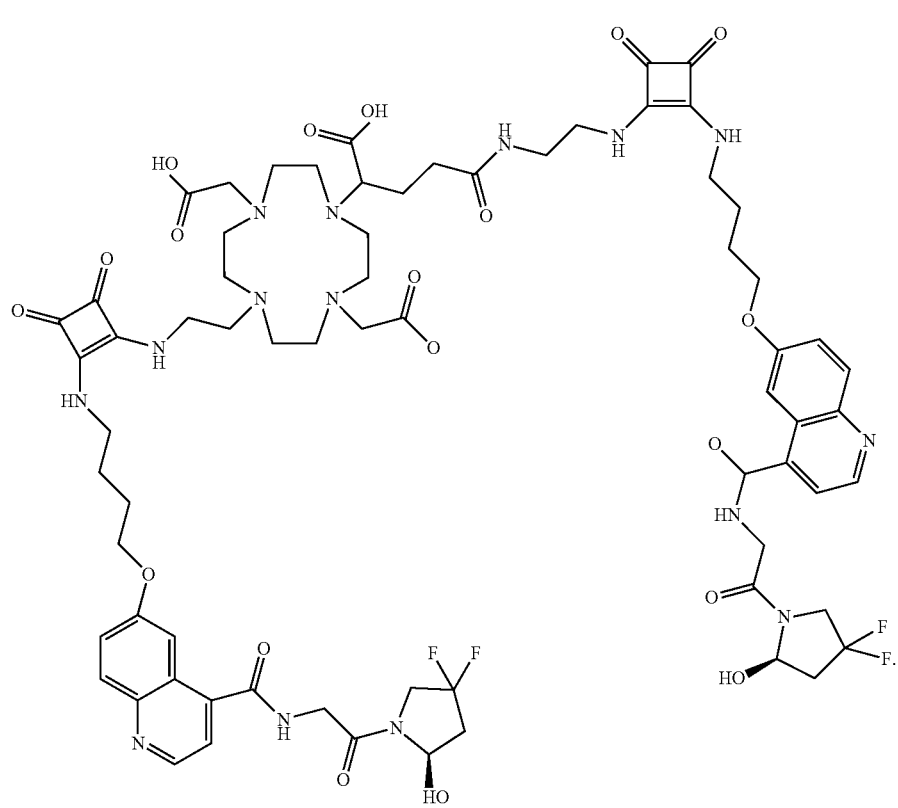

13. The method of diagnosing and/or treating cancer according to claim 12, wherein the radioactive isotope is selected from $^{44}$Sc, $^{47}$Sc, $^{55}$Co, $^{62}$Cu, $^{64}$Cu, $^{67}$Cu, $^{66}$Ga, $^{67}$Ga, $^{68}$Ga, $^{89}$Zr, $^{86}$Y, $^{90}$Y, $^{90}$Nb, $^{99m}$Tc, $^{111}$In, $^{135}$Sm, $^{140}$Pr, $^{159}$Gd, $^{149}$Tb, $^{160}$Tb, $^{161}$Tb, $^{165}$Er, $^{166}$Dy, $^{166}$Ho, $^{175}$Yb, $^{177}$Lu, $^{186}$Re, $^{188}$Re, $^{213}$Bi and $^{225}$Ac.

14. The method of diagnosing and/or treating cancer according to claim 12, wherein the method is a method of diagnosing the radioactive isotope is $^{68}$Ga or the method is a method of treatment and the radioactive isotope is $^{177}$Lu.

15. The labeling precursor according to claim 1, wherein the targeting vector is connected to $S_1$ and $S_2$ via ether linkages.

* * * * *

UNITED STATES PATENT AND TRADEMARK OFFICE
CERTIFICATE OF CORRECTION

| | | |
|---|---|---|
| PATENT NO. | : 11,833,229 B2 | Page 1 of 1 |
| APPLICATION NO. | : 17/745100 | |
| DATED | : December 5, 2023 | |
| INVENTOR(S) | : Rösch et al. | |

It is certified that error appears in the above-identified patent and that said Letters Patent is hereby corrected as shown below:

In the Claims

Column 43, Line 20, Claim 11 formula (I):

The portion of the formula reading "  "

Should read --  --

Signed and Sealed this
Twenty-seventh Day of February, 2024

Katherine Kelly Vidal
*Director of the United States Patent and Trademark Office*